US012741022B2

(12) United States Patent
Martin et al.

(10) Patent No.: US 12,741,022 B2
(45) Date of Patent: Sep. 22, 2026

(54) VACCINES, VACCINE PRIMING, AND ANTIGEN DOSE SPARING

(71) Applicant: ADJUVANCE TECHNOLOGIES, INC., Lincoln, NE (US)

(72) Inventors: J. Tyler Martin, Roca, NE (US); Eric Jon Farris, Lincoln, NE (US); Anna Therese Lampe, Lincoln, NE (US)

(73) Assignee: ADJUVANCE TECHNOLOGIES, INC., Lincoln, NE (US)

( * ) Notice: Subject to any disclaimer, the term of this patent is extended or adjusted under 35 U.S.C. 154(b) by 731 days.

(21) Appl. No.: 18/011,064

(22) PCT Filed: Jun. 17, 2021

(86) PCT No.: PCT/US2021/037907

§ 371 (c)(1),
(2) Date: Dec. 16, 2022

(87) PCT Pub. No.: WO2021/257884

PCT Pub. Date: Dec. 23, 2021

(65) Prior Publication Data

US 2023/0263886 A1 Aug. 24, 2023

Related U.S. Application Data

(60) Provisional application No. 63/072,872, filed on Aug. 31, 2020, provisional application No. 63/058,874, filed on Jul. 30, 2020, provisional application No. 63/041,035, filed on Jun. 18, 2020.

(51) Int. Cl.

| | |
|---|---|
| ***A61K 39/39*** | (2006.01) |
| ***A61K 39/00*** | (2006.01) |
| ***A61K 39/145*** | (2006.01) |
| ***A61K 39/215*** | (2006.01) |
| ***A61K 39/25*** | (2006.01) |
| ***A61P 31/14*** | (2006.01) |
| ***A61P 31/16*** | (2006.01) |
| ***A61P 31/22*** | (2006.01) |

(52) U.S. Cl.

CPC ............ *A61K 39/39* (2013.01); *A61K 39/145* (2013.01); *A61K 39/215* (2013.01); *A61K 39/25* (2013.01); *A61P 31/14* (2018.01); *A61P 31/16* (2018.01); *A61P 31/22* (2018.01); *A61K 2039/545* (2013.01); *A61K 2039/55511* (2013.01); *A61K 2039/70* (2013.01)

(58) Field of Classification Search

CPC .................. A61K 39/39; A61K 31/704; A61K 2039/55583; A61K 2039/545; A61K 39/12

See application file for complete search history.

(56) References Cited

U.S. PATENT DOCUMENTS

| | | | |
|---|---|---|---|
| 3,985,615 | A | 10/1976 | Kubo |
| 4,684,479 | A | 8/1987 | D'Arrigo |
| 5,215,680 | A | 6/1993 | D'Arrigo |
| 5,874,104 | A | 2/1999 | Adler-Moore et al. |
| 5,916,588 | A | 6/1999 | Popescu et al. |
| 5,965,156 | A | 10/1999 | Proffitt et al. |
| 6,008,203 | A | 12/1999 | Magnani et al. |
| 6,043,094 | A | 3/2000 | Martin et al. |
| 6,056,973 | A | 5/2000 | Allen et al. |
| 6,080,725 | A | 6/2000 | Marciani et al. |
| 6,126,966 | A | 10/2000 | Abra et al. |
| 6,262,029 | B1 | 7/2001 | Press et al. |
| 6,294,191 | B1 | 9/2001 | Meers et al. |
| 6,316,024 | B1 | 11/2001 | Allen et al. |
| 6,352,716 | B1 | 3/2002 | Janoff et al. |
| 6,406,713 | B1 | 6/2002 | Janoff et al. |
| 6,759,057 | B1 | 7/2004 | Weiner et al. |
| 8,283,456 | B2 | 10/2012 | Gin et al. |
| 8,889,842 | B2 | 11/2014 | Gin et al. |
| 9,718,850 | B2 | 8/2017 | Gin et al. |
| 11,324,821 | B2 | 5/2022 | Martin et al. |
| 2003/0095974 | A1 | 5/2003 | Garcon et al. |
| 2004/0208921 | A1 | 10/2004 | Ho et al. |
| 2009/0035360 | A1 | 2/2009 | Lemoine |
| 2009/0047306 | A1 | 2/2009 | Nash et al. |
| 2010/0272745 | A1 | 10/2010 | Lemoine et al. |
| 2010/0322958 | A1 | 12/2010 | Bardotti et al. |
| 2011/0104260 | A1 | 5/2011 | Hanon et al. |
| 2011/0206758 | A1 | 8/2011 | Vandepapeliere |
| 2012/0087976 | A1 | 4/2012 | Henderickx et al. |
| 2012/0164178 | A1 | 6/2012 | Ballou, Jr. et al. |
| 2013/0011421 | A1 | 1/2013 | Gin et al. |
| 2013/0309273 | A1 | 11/2013 | Hassett et al. |

(Continued)

FOREIGN PATENT DOCUMENTS

| | | | |
|---|---|---|---|
| CL | 2011003113 | A1 | 8/2012 |
| CL | 2012000585 | A1 | 9/2012 |

(Continued)

OTHER PUBLICATIONS

Abbas Vafai, "Antibody-binding sites on truncated forms of varicella-zoster virus gpI(gE) glycoprotein", Vaccine, vol. 12, No. 14 (1994), pp. 1265-1269.
Adams et al., "Design and Synthesis of Potent Quillaja Saponin Vaccine Adjuvants", J Am Chem Soc. 1939(2010), vol. 132 (6), pp. 1-16.
Adams, "Synthesis of Saponin Immunoadjuvants", University of Illinois at Urbana-Champaign, Ph.D. Dissertation 2009 [retrieved on Jul. 18, 2018). Retrieved from the Internet: <URL: https://search.proquest.com/docview/304896057>. See Abstract, pp. 45-47.

(Continued)

*Primary Examiner* — Barry A Chestnut
(74) *Attorney, Agent, or Firm* — Paul D. Strain, Esq.; Strain & Strain PLLC

(57) ABSTRACT

The present application relates to new vaccines, improved vaccine priming, and antigen dose sparing in connection with triterpene glycoside saponin-derived adjuvants, salt forms thereof, and pharmaceutical compositions, as well as related methods.

7 Claims, 27 Drawing Sheets

(56) References Cited

U.S. PATENT DOCUMENTS

| | | | |
|---|---|---|---|
| 2014/0072622 | A1 | 3/2014 | Denoel et al. |
| 2014/0228286 | A1 | 8/2014 | Luippold et al. |
| 2015/0037374 | A1 | 2/2015 | Bazmorelli et al. |
| 2015/0086585 | A1 | 3/2015 | Gin et al. |
| 2017/0014507 | A1 | 1/2017 | Bazmorelli et al. |
| 2017/0065715 | A1 | 3/2017 | Vandepapeliere |
| 2017/0096444 | A1 | 4/2017 | Gin et al. |
| 2018/0008700 | A1 | 1/2018 | Heineman et al. |
| 2018/0327436 | A1 | 11/2018 | Gin et al. |
| 2019/0275135 | A1 | 9/2019 | Poolman |
| 2020/0164065 | A1 | 5/2020 | Gardner et al. |
| 2020/0239509 | A1 | 7/2020 | Gin et al. |
| 2020/0261571 | A1 | 8/2020 | Martin et al. |
| 2020/0276299 | A1 | 9/2020 | Fox et al. |
| 2021/0002316 | A1 | 1/2021 | Gin et al. |
| 2021/0283248 | A1 | 9/2021 | Livingston et al. |
| 2022/0184207 | A1 | 6/2022 | Martin et al. |
| 2022/0409721 | A1 | 12/2022 | Martin et al. |
| 2023/0128815 | A1 | 4/2023 | Martin et al. |
| 2023/0219991 | A1 | 7/2023 | Gin et al. |
| 2023/0357300 | A1 | 11/2023 | Chan et al. |

FOREIGN PATENT DOCUMENTS

| | | | |
|---|---|---|---|
| EP | 0 192 902 | A2 | 9/1986 |
| JP | 2011-516566 | A | 5/2011 |
| WO | WO 93/05789 | A1 | 4/1993 |
| WO | WO 94/02596 | A1 | 2/1994 |
| WO | WO 96/33739 | A1 | 10/1996 |
| WO | WO 2001/015727 | A2 | 3/2001 |
| WO | WO 2006/094756 | A2 | 9/2006 |
| WO | WO 2009/080715 | A2 | 7/2009 |
| WO | WO 2009/126737 | A2 | 10/2009 |
| WO | WO 2010/142685 | A1 | 12/2010 |
| WO | WO 2011/027222 | A2 | 3/2011 |
| WO | WO 2012/158978 | A1 | 11/2012 |
| WO | WO 2015/148648 | A1 | 10/2015 |
| WO | WO 2015/184451 | A1 | 12/2015 |
| WO | WO 2017/079582 | A1 | 5/2017 |
| WO | WO 2017/106836 | A1 | 6/2017 |
| WO | WO 2018/114892 | A1 | 6/2018 |
| WO | WO 2018/191598 | A1 | 10/2018 |
| WO | WO 2018/198085 | A1 | 11/2018 |
| WO | WO 2018/200645 | A1 | 11/2018 |
| WO | WO 2018/200656 | A1 | 11/2018 |
| WO | WO 2019/079160 | A1 | 4/2019 |
| WO | WO 2021/091997 | A1 | 5/2021 |
| WO | WO 2021/195024 | A1 | 9/2021 |
| WO | WO 2021/257884 | A1 | 12/2021 |
| WO | WO 2022/221393 | A1 | 10/2022 |

OTHER PUBLICATIONS

Arbeter et al., "Live attenuated varicella vaccine: Immunization of healthy children with the OKA strain", The Journal of Pediatrics, vol. 100, No. 6 (1982), pp. 886-893.

Arvin et al., "Equivalent recognition of a varicella-zoster virus immediate early protein (IE62) and glycoprotein I by cytotoxic T lymphocytes of either CD4+ or CD8+ phenotype", J Immunol, vol. 146 (1991), pp. 257-264.

Arvin et al., "Memory Cytotoxic T Cell Responses to Viral Tegument and Regulatory Proteins Encoded by Open Reading Frames 4, 10, 29, and 62 of Varicella-Zoster Virus", Viral Immunology, vol. 15, No. 3 (2002), pp. 507-516.

Balsevich et al., "Analysis of bisdesmosidic saponins in *Saponaria vaccaria* L. by HPLC-PAD-MS: identification of new quillaic acid and gypsogenin 3-O-Trisaccharides." Phytochemical analysis, vol. 17, No. 6, pp. 414-423 (Oct. 18, 2006) (https://doi.org/10.1002/pca.943).

Carcaboso et al., Potent, long lasting systematic antibody levels and mixed Th1/Th2 immune response after nasal immunization with malaria antigen loaded PLGA microparticles, Vaccine (2004), vol. 22, (11-12), pp. 1423-1432.

Chea etal., "Synthesis and Preclinical Evaluation of QS-21 Variants Leading to Simplified Vaccine Adjuvants and Mechanistic Probes", J Am Chem Soc. vol. 134, No. 32 (2012), 26 pgs.

Coccia et al., "Cellular and molecular synergy in AS01-adjuvanted vaccines results in an early IFNγ response promoting vaccine immunogenicity", npj Vaccines, vol. 2 (2018), pp. 1-14.

Coplan et al., "Development of a Measure of the Burden of Pain Due to Herpes Zoster and Postherpetic Neuralgia for Prevention Trials: Adaptation of the Brief Pain Inventory", The Journal of Pain, vol. 5, No. 6 (2004), pp. 344-356.

Debrus et al., "Varicella-Zoster Virus Gene 63 Encodes an Immediate-Early Protein That Is Abundantly Expressed during Latency", Journal of Virology, vol. 69, No. 5 (1995), pp. 3240-3245.

Evans et al., "QS-21 promotes an adjuvant effect allowing for reduced antigen dose during HIV-1 envelope subunit immunization in humans", Vaccine (2001), vol. 19, pp. 2080-2091.

Fernandez-Tejada et al., "Development of a minimal saponin vaccine adjuvant based on QS-21", Published in final edited form as: Nat Chem. vol. 6, No. 7 (2014), pp. 635-643.

Fernández-Tejada et al., "Development of Improved Vaccine Adjuvants Based on the Saponin Natural Product QS-21 through Chemical Synthesis", Accounts of Chemical Research (2016), vol. 49, pp. 1741-1756.

Fernández-Tejada et al., "Semisynthesis of Analogues of the Saponin Immunoadjuvant QS-21", Methods in Molecular Biology (2016), vol. 1494, pp. 45-71.

Fernández-Tejada et al., "Versatile Strategy for the Divergent Synthesis of Linear Oligosaccharide Domain Variants of Quillaja Saponin Vaccine Adjuvants", Chem Commun (2015), vol. 51 (73), pp. 13949-13952.

Fernandez-Tejada et al; "Design, synthesis, and immunologic evaluation of vaccine adjuvant conjugates based on QS-21 and tucaresol" Bioorganic & Medicinal Chemistry, vol. 22, No. 21 (2014), pp. 5917-5923.

Fernandez-Tejada et al; "Development of a Minimal Saponin Vaccine Adjuvant based on QS-21", Supplementary Information, Nature Chemistry, vol. 6 (2014), pp. S1-S135.

Fleck et al., "Saponins from Quillaja saponaria and Quillaja brasiliensis: Particular Chemical Characteristics and Biological Activities", Molecules (2019), vol. 24, No. 171, pp. 1-29.

Gilden et al., "Neurologic Complications of the Reactivation of Varicella-Zoster Virus", Engl J Med., vol. 342, No. 9 (2000), pp. 635-645.

Gin et al., "Enhancing Immunogenicity of Cancer Vaccines: QS-21 as an Immune Adjuvant", Curr Drug ther. (2011), vol. 6 (3), pp. 207-212.

Guo et al., "Triterpenoid Saponins From Quillaja Saponaria" Phytochemistry, vol. 48, No. 1, pp. 175-180 (1998).

Harlow and Lane, "Antibodies: A Laboratory Manual", Cold Spring Harbor Laboratory (1988), pp. 726, Biochemical Education, vol. 17, No. 4 (1989).

Haumont et al., "Purification, characterization and immunogenicity of recombinant varicella-zoster virus glycoprotein gE secreted by Chinese hamster ovary cells", Virus Research, vol. 40 (1996), pp. 199-204.

Huang et al., "Specific Lysis of Targets Expressing Varicella-Zoster Virus gpl or gplV by CD4+ Human T-Cell Clones", J. Virol., Vo. 66, No. 5 (1992), pp. 2664-2669.

International Search Report, PCT/US2021/037907, Oct. 1, 2021, 1 pg.

Kashala et al., "Safety, tolerability and immunogenicity of new formulations of the Plasmodium falciparum malaria peptide vaccine SPf66 combined with the immunological adjuvant QS-21", Vaccine (2002), vol. 20, pp. 2263-2277.

Kensil et al., "Separation and characterization of saponins with adjuvant activity from Quillaja saponaria Molina cortex", Journal of Immunology (1991), vol. 146 (2), pp. 431-437.

Kensil, "Saponins as Vaccine Adjuvants", Critical Reviews in Therapeutic Drug Carrier Systems (1996), vol. 13 (1&2), pp. 1-55.

Kim et al., "Comparison of the effect of different immunological adjuvants on the antibody and T-cell response to Immunization with MUC1-KLH and GD3-KLH conjugate cancer vaccines", Vaccine (2000), vol. 18, pp. 597-603.

(56) References Cited

OTHER PUBLICATIONS

Livingston et al., "Cancer vaccines targeting carbohydrate antigens", Human Vaccines (May-Jun. 2006), vol. 2 (3), pp. 137-143.
Marin et al., "Prevention of Varicella: Recommendations of the Advisory Committee on Immunization Practices (ACIP)", MMWR Recomm Rep., vol. 56, No. RR-4 (2007); pp. 1-40.
Newman et al., "Saponin adjuvant induction of ovalbumin-specific CD8+ cytotoxic T lymphocyte responses", Journal of Immunology (1992), vol. 148, pp. 2357-2362.
Ragupathi et al., "Natural and synthetic saponin adjuvant QS-21 for vaccines against cancer", Expert Rev Vaccines (2011), vol. 10 (4), pp. 463-470.
Ragupathi et al., "Preclinical Evaluation of the Synthetic Adjuvant SQS-21 and its Constituent Isomeric Saponins", Vaccine (2010), vol. 28 (26), pp. 4260-4267.
Rodriguez-Diaz et al., "Topical anti-inflammatory activity of quillaic acid from *Quillaja saponaria* Mol. and some derivatives", Journal of Pharmacy and Pharmacology (2011), vol. 63, pp. 718-724.
Sabella et al., "Immunization with the Immediate-Early Tegument Protein (Open Reading Frame 62) of Varicella-Zoster Virus Protects Guinea Pigs against Virus Challenge", Journal of Virology, vol. 67, No. 12 (1993), pp. 7673-7676.
Sasaki et al., "Induction of systemic and mucosal immune responses to human immunodeficiency virus type 1 by a DNA vaccine formulated with QS-21 saponin adjuvant via intramuscular and intranasal routes", Journal of Virology (Jun. 1998), vol. 72 (6), pp. 4931-4939.
Sawyer et al., "Detection of Varicella-Zoster Virus DNA in Air Samples from Hospital Rooms", J Infect Dis., vol. 169 (1994), pp. 91-94.
Senders et al., "1236. Safety and Immunogenicity of a 20-Valent Pneumococcal Conjugate Vaccine (PCV20) in Healthy Infants in the United States", Open Forum Infectious Diseases (Oct. 2020), vol. 7 (Suppl 1), p. S637.
Sharp et al., "Kinetics and Viral Protein Specificity of the Cytotoxic T Lymphocyte Response in Healthy Adults Immunized with Live Attenuated Varicella Vaccine", JID, vol. 165 (1992), pp. 852-858.
Soltysik et al., "Structure/function studies of QS-21 adjuvant: assessment of triterpene aldehyde and glucuronic acid roles in adjuvant function", Vaccine (1995), vol. 13 (15), pp. 1403-1410.
Van Setten et al., "Glycosyl compositions and structural characteristics of the potential immunoadjuvant active saponins in the Quillaja saponaria Mollina extract Quil A", Rapid Communications in Mass Spectrometry (1995), vol. 9, pp. 660-666.
Walkowicz et al., "Quillaja saponin variants with central glycosidic linkage modifications exhibit distinct conformations and adjuvant activities", Chem. Sci. (2016), vol. 7, pp. 2371-2380.
Abstract of Slingluff et al, Journal for Immuno Therapy of Cancer (Nov. 6, 2014), vol. 2, Suppl. 3, Abstract No. P60. 2 pgs.
Alving et al., "Liposomal adjuvants for human vaccines", Expert Opinion on Drug Delivery (2016), vol. 13, No. 6, pp. 807-816.
Bautz, "OGEN: COVID-19 Vaccine Candidate Exhibits Protective Immunity in Mice . . . ", Zacks Small-Cap Research (Apr. 9, 2021), pp. 1-7.
Berge et al., "Pharmaceutical Salts", Journal of Pharmaceutical Sciences, vol. 66, No. 1 (1977), pp. 1-19.
Brichard, "Development of cancer vaccines with the MAGE-3 protein", Cancer Immunity (2005), vol. 5, Suppl. 1, p. 16.
Cibulski et al., "Novel ISCOMs from Quillaja brasiliensis saponins induce mucosal and systemic antibody production, T-cell responses and improved antigen uptake", Vaccine, vol. 34 (2016), pp. 1162-1171.
Didierlaurent et al., "Adjuvant system AS01: helping to overcome the challenges of modern vaccines", Expert Review of Vaccines (2017), vol. 16, No. 1, pp. 55-63.
Fox, "Squalene Emulsions for Parenteral Vaccine and Drug Delivery", Molecules (2009), vol. 14, pp. 3286-3312.
Garcon et al., "Understanding Modern Vaccines: Perspectives in Vaccinology", Vaccine Adjuvants (2011), vol. 1, No. 1, pp. 89-113.
Kensil et al., "QS-21: a water-soluble triterpene glycoside adjuvant", Expert Opinion on Investigational Drugs (1998), vol. 7, No. 9, pp. 1475-1482.
Liu et al., "Prednisolone-Glucose Derivative Conjugate: Synthesis, Biodistribution and Pharmacodynamics Evaluation", Arch. Pharm. Chem. Life Sci. (2012), vol. 345, pp. 925-933.
Patra et al., "Alga-Produced Malaria 'Transmission-Blocking Vaccine Candidate Pfs25 Formulated with a Human Use-Compatible Potent Adjuvant Induces High-Affinity Antibodies' That Block Plasmodium falciparum Infection of Mosquitoes", Infection and Immunity (2015), vol. 83, No. 5, pp. 1799-1808.
Scott et al., "Mitsunobu Inversion of a Secondary Alcohol with Diphenylphosphoryl azide. Application to the Enantioselective Multikilogram Synthesis of a HCV Polymerase Inhibitor", Organic Process Research and Development (2011), vol. 15, pp. 1116-1123.
Slingluff et al., "A randomized pilot trial testing the safety and immunologic effects of a MAGE-A3 protein plus AS15 immunostimulant administered into muscle or into dermal/subcutaneous sites", Cancer Immunol Immunother (2016), vol. 65, pp. 25-36.
Squarcia et al., "Glycal-mediated syntheses of enantiomerically pure polyhydroxylated γ- and δ-lactams", Tetrahedron Letters (2002), vol. 43, pp. 4653-4655.
Toussi et al., "Immune Adjuvant Effect of Molecularly-defined Toll-Like Receptor Ligands", Vaccines (2014), vol. 2, pp. 323-353.
Wang, "Natural and Synthetic Saponins as Vaccine Adjuvants", Vaccines, vol. 9, No. 222 (2021), pp. 1-18.
Wojtczak, "Glossary of Medical Education Terms", Medical Teacher, vol. 24 (2002), pp. 1-24.
Wui et al., "Efficient induction of cell-mediated immunity to varicella-zoster virus glycoprotein E co-lyophilized with cationic liposome-based adjuvant in mice", Vaccine (2019), vol. 37, pp. 2131-2141.
Wuts et al.; "Chapter 2: Protection for the Hydroxyl Group, Including 1,2- and 1,3-Diols", Greene's Protective Groups in Organic Synthesis, 4th Ed. (Dec. 31, 2006), 351 pgs.

| Grp | Mice | Antigen | Adjuvant Formulation | Administration route | Dosing Day | Serology |
|---|---|---|---|---|---|---|
| 1 | 10 | 4.5 µg FluBlok | --- | Subcutaneous | D0, D14 | D0, D14, D28 |
| 2 | 10 | 1.125 µg FluBlok | --- | Subcutaneous | D0, D14 | D0, D14, D28 |
| 3 | 10 | 1.125 µg FluBlok | 30 µg 1055 Choline Salt | Subcutaneous | D0, D14 | D0, D14, D28 |
| 4 | 10 | 0.56 µg FluBlok | 30 µg 1055 Choline Salt | Subcutaneous | D0, D14 | D0, D14, D28 |
| 5 | 10 | 0.28 µg FluBlok | 30 µg 1055 Choline Salt | Subcutaneous | D0, D14 | D0, D14, D28 |
| 6 | 10 | 0.14 µg FluBlok | 30 µg 1055 Choline Salt | Subcutaneous | D0, D14 | D0, D14, D28 |

FIG. 1

Post dose 1 (D14) anti-B/Phuket IgG Endpoint Titers

Post dose 2 (D28) anti-B/Phuket IgG Endpoint Titers

Post dose 2 (D28) B/Phuket Hemagglutination Inhibition (HI) Titers

Low dose FluBlok + 30 μg 1055 salt induces significantly higher anti-H3N2 IgG titers after 1 dose compared to high dose FluBlok alone after 2 doses

Low dose FluBlok + 30 µg 1055 salt induces similar anti-H1N1 IgG titers after 1 dose compared to high dose FluBlok alone after 2 doses

Low dose FluBlok + 30 µg 1055 salt induces similar anti-B/Phuket IgG titers after 1 dose compared to high dose FluBlok alone after 2 doses

Anti-SARS-CoV-2 Fl-S Total IgG
Post Dose 1
FL-S 0.3 μg dose groups

VACCINES, VACCINE PRIMING, AND ANTIGEN DOSE SPARING

CROSS-REFERENCE TO RELATED PATENT APPLICATIONS

This application is a National Stage of International Application No. PCT/US2021/037907, filed Jun. 17, 2021, which is based upon and claims the benefit of priority under 35 U.S.C. § 119(e) to U.S. Provisional Applications No. 63/041,035 filed Jun. 18, 2020, No. 63/072,872 filed Aug. 31, 2020, and No. 63/058,874 filed Jul. 30, 2020, the entire contents of all of which are incorporated herein by reference in their entirety.

FIELD OF THE INVENTION

The present application relates to new vaccines, improved vaccine priming, and antigen dose sparing in connection with triterpene glycoside saponin-derived adjuvants, salt forms thereof, and pharmaceutical compositions, as well as related methods.

BACKGROUND

Vaccines continue to improve public health across the world. As exemplified by the recent development of several vaccines against SARS-CoV-2, an effective vaccine can require more than a single administration of a vaccine composition for an individual to be effectively inoculated. In particular, vaccine regimens often follow a priming-boosting approach whereby an initial vaccine dose is administered to prime the immune system to respond to the antigen and one or more second vaccine doses are administered to boost the immune response to the antigen and achieve effective inoculation against the antigen-presenting pathogen, e.g. a virus, bacterium, etc. Such approach, however, has drawbacks, including requiring greater vaccine antigen quantities to achieve effective inoculation and delaying the onset of effective inoculation.

Furthermore, in the case of novel pathogens, including pandemic pathogens like H5N1 (avian influenza or Bird Flu), SARS-CoV-1 (SARS) and SARS-CoV-2 (COVID-19), the immune system typically does not produce a strong response when initially challenged with a pathogen or a pathogen-associated antigen. This is especially true in the case of subunit antigens, which are becoming more and more common. In such circumstances, a priming-boosting approach is required, delaying the onset of inoculation and requiring more vaccine antigen to be produced. In a practical sense, this approach substantially extends the time required for a population to develop herd immunity and/or the time to reduce the effective R0 to a level where the pandemic begins to decline. Indeed, it was reported neutralizing antibodies developed in patients exposed to SARS-CoV-1 were relatively short-lived. See, e.g. Wu et al., Duration of Antibody Responses after Severe Acute Respiratory Syndrome, Emerg Infect Dis. 2007 October; 13(10): 1562-1564. doi: 10.3201/eid1310.070576. A preprint publication suggested antibodies developed in patients exposed to SARS CoV-2 were even more short lived, potentially lasting as few as several months. See Liu et al., Prevalence of IgG antibodies to SARS-CoV-2 in Wuhan. Studies are currently ongoing to assess the duration of protection afforded by the vaccines currently authorized under Emergency Use Authorization authority in the United States (and under similar authority elsewhere).

Furthermore, the time and cost associated with vaccine antigen development, production, and storage continues to present significant risks to global public health. Where only a limited supply of vaccine antigen is maintained, for example in the case of national vaccine stockpiles, or where vaccine antigen is particularly difficult to manufacture, only a portion of the affected population may be able to receive a vaccine when needed. In the case of an epidemic, pandemic, or other health emergency requiring rapid development or production of a novel vaccine, vaccine antigen may not be able to be produced quickly enough to meet demand, thus prolonging the emergency. Where vaccine antigen is expensive to manufacture, vaccines may not be sufficiently available if patients are unable to economically offset antigen manufacturing costs.

It would therefore be advantageous in developing vaccines against pandemic pathogens like SARS-CoV-2 for a vaccine to induce a strong priming response after the initial dose using as little antigen as possible such that (a) no boosting dose is required, (b) fewer boosting doses are required, (c) a boosting dose is administered later than otherwise required, and/or (d) a boosting dose does not require as much vaccine antigen to achieve the same immunological effect (dose sparing).

Antigen dose sparing seeks to address these problems by reducing the amount of antigen required per dose of vaccine. Several approaches are typical for investigating antigen dose sparing, including investigating antigen re-design, dose-response optimization, fractional dosing, route of administration, and adjuvant systems.

Furthermore, it would be advantageous in developing vaccines if certain antigens could be combined in one combination vaccine to protect individuals against a number of pathogens.

SUMMARY

The present application encompasses the recognition improved vaccine priming and antigen dose sparing is needed to address multiple needs, including the need for an efficient and effective vaccine against COVID-19. The present application also encompasses the recognition improved combination vaccines against SARS-CoV-2 and Influenza would improve public health. The inventors of the present application have discovered certain synthetic saponin molecules, including TQL-1055, as well as pharmaceutically acceptable salt forms thereof, enable substantially improved vaccine priming and dose sparing in comparison with prior techniques. The inventors of the present application have also discovered combination vaccines against SARS-CoV-2 and Influenza.

In particular, the inventors of the present application have found TQL-1055 can support at least 32× dose sparing for vaccine antigens, including a recombinant influenza antigen. The inventors of the present application have also found a single dose of a vaccine adjuvanted with TQL-1055 and containing a vaccine antigen diluted 32× produces a similar immune response as two doses of unadjuvanted, undiluted antigen alone. Thus, the inventors of the present application have found TQL-1055 exhibits both substantial priming and antigen sparing effects, which are critical in pandemic situations (e.g. SARS-CoV-2 vaccinations), as well as non-pandemic situations (e.g. high volume yearly seasonal influenza vaccinations).

The present application also provides vaccine formulations that incorporate antigens associated with a plurality of pathogens. In this way, the vaccine formulations can leverage one or more of the foregoing effects to provide effective and efficient inoculation against multiple pathogens at the same time. For example. The present application provides a highly effective influenza/COVID-19 combination vaccine.

Thus, in one aspect, the present application provides TQL-1055:

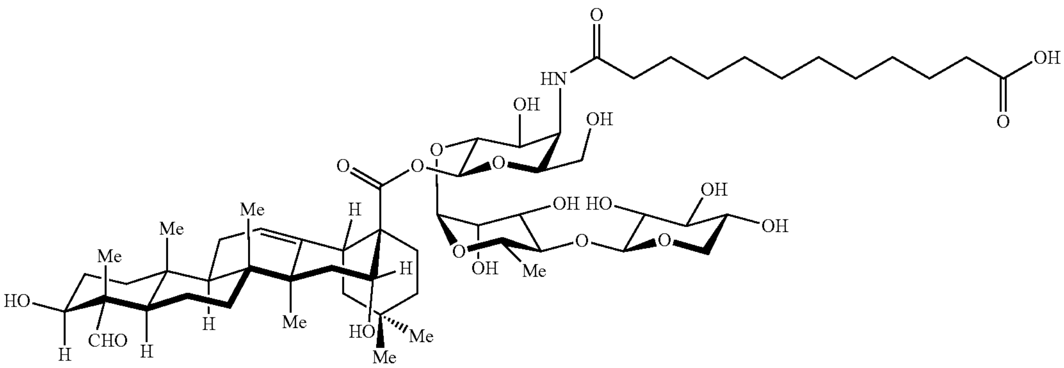

In another aspect, the present application provides stable crystalline salt forms of TQL-1055.

In another aspect, the present application provides compounds of Formula I:

(I)

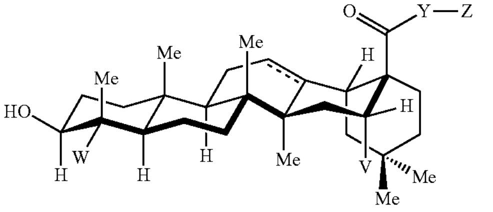

or a pharmaceutically acceptable salt thereof, wherein

⎓ is a single or double bond;

W is-CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

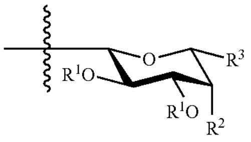

or

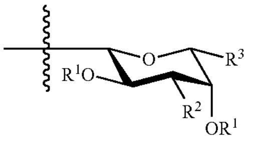

wherein each occurrence of $R^1$ is $R^x$ or a carbohydrate domain having the structure:

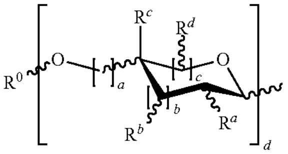

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, NHC (O)$R^4$, NRC(O)$R^4$, NHC(O)O$R^4$, NHC(O)NH$R^4$, NHC(O)NR$R^4$, NH$R^4$, N$(R^4)_2$, NH$R^4$, NR$R^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

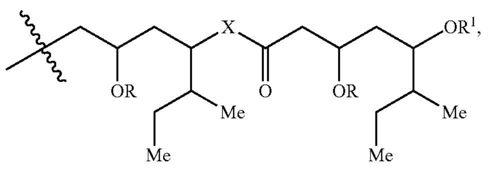

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —O$R^x$, —O$R^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula II:

(II)

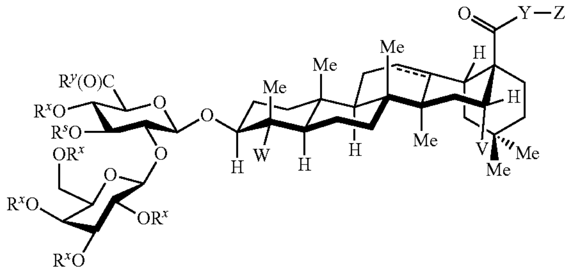

or a pharmaceutically acceptable salt thereof, wherein

⎓ is a single or double bond;

W is Me, —CHO, or

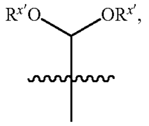

V is hydrogen or O$R^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

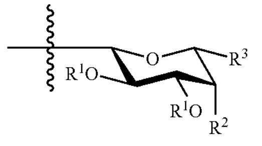

or

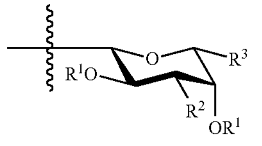

wherein each occurrence of $R^1$ is $R^x$ or a carbohydrate domain having the structure:

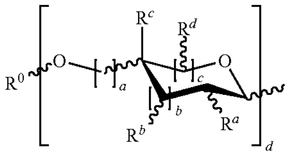

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

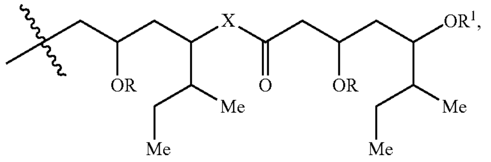

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

$R^y$ is —OH, —OR, or a carboxyl protecting group selected from the group consisting of ester, amides, and hydrazides;

$R^s$ is

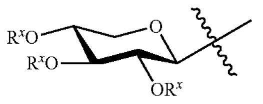

or

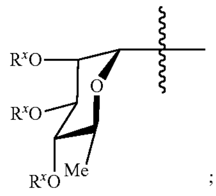

;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

It will be appreciated by one of ordinary skill in the art that the compounds of the present application include, but are not necessarily limited to, those compounds encompassed in the genus set forth herein. The compounds encompassed by this application include at least all of the compounds disclosed in the entire specification as a whole, including all individual species within each genus.

According to another aspect of the present subject matter, the compounds disclosed in this application have been shown to be useful as adjuvants. In another aspect, the present application provides a method for preparing compounds according to the embodiments of this application. In another aspect, the present invention provides a method of potentiating an immune response to an antigen, comprising administering to a subject a provided vaccine in an effective amount to potentiate the immune response of said subject to said antigen.

In another aspect, the present invention provides methods of vaccinating a subject, comprising administering a provided vaccine to said subject. In some embodiments, the subject is human. In some embodiments, the vaccine is administered as an injectable.

In another aspect, the invention provides pharmaceutical compositions comprising compounds of the invention and pharmaceutically acceptable excipients. In certain embodiments, the pharmaceutical composition is a vaccine comprising an antigen and an inventive adjuvant.

In another aspect, the invention provides kits comprising pharmaceutical compositions of inventive compounds. In some embodiments, the kits comprise prescribing information. In some embodiments, such kits include the combination of an inventive adjuvant compound and another immunotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. In certain embodiments, the kit includes one cycle of immunotherapy. In certain embodiments, the kit includes a sufficient quantity of a pharmaceutical composition to immunize a subject against an antigen long term.

In another aspect, the application provides formulations of compositions according to the present application in an adjuvant system. In some embodiments, the adjuvant system utilizes a carrier. In some embodiments, the carrier is a particulate carrier such as metallic salt particles, emulsions, polymers, liposomes, or immune stimulating complexes (ISCOMs). In some embodiments, the adjuvant system includes GLA, MPL, 3D-MPL, LPS, cholesterol, CpG (e.g. CpG 7907 or CpG 1018), PolyIC:LC, aluminum hydroxide, aluminum phosphate, tocopherol, acylated monosaccharides, other saponin derivatives (e.g. Quil-A, ISCOM, QS-21, ASO2 and ASO1), soluble triterpene glycosides, Toll-like receptor 4 (TLR4) agonists, Toll-like receptor 3 (TLR3) agonists, montanides (ISA51, ISA720), immunostimulatory oligonucleotides, and imidazoquinolines. In some embodiments, the adjuvant system includes known immunostimulants. In some embodiments, the adjuvant system utilizes common adjuvants such as alum, Freund's adjuvant (an oil-in-water emulsion with dead mycobacteria), Freund's adjuvant with MDP (an oil-in-water emulsion with muramyl dipeptide, MDP, a constituent of mycobacteria), alum plus *Bordetella pertussis* (aluminum hydroxide gel with killed *B. pertussis*), enterobacteria, FU glycosides, synthetic or derived outer membrane vesicles, chitosan microparticles and microcarrier parties, or other known adjuvants.

As used herein, the following definitions shall apply unless otherwise indicated.

"Liposomes" as used herein refer to closed bilayer membranes containing an entrapped aqueous volume. Liposomes may also be uni-lamellar vesicles possessing a single membrane bilayer or multi-lamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. Liposomes, as they are ordinarily used, consist of smectic mesophases, and can consist of either phospholipid or non-phospholipid smectic mesophases. Smectic mesophase is most accurately described by Small, HANDBOOK OF LIPID RESEARCH, Vol. 4, Plenum, NY, 1986, pp. 49-50. According to Small, "[w]hen a given molecule is heated, instead of melting directly into an isotropic liquid, it may instead pass through intermediate states called mesophases or liquid crystals, characterized by residual order in some directions but by lack of order in others. In general, the molecules of liquid crystals are somewhat longer than they are wide and have a polar or aromatic part somewhere along the length of the molecule. The molecular shape and the polar-polar, or aromatic, interaction permit the molecules to align in partially ordered arrays. These structures characteristically occur in molecules that possess a polar group at one end. Liquid crystals with long-range order in the direction of the long axis of the molecule are called smectic, layered, or lamellar liquid crystals. In the smectic states the molecules may be in single or double layers, normal or tilted to the plane of the layer, and with frozen or melted aliphatic chains."

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent $C_{1-12}$ (or $C_{1-26}$, $C_{1-16}$, $C_{1-8}$) or saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)n$-, wherein n is a positive integer, preferably from 1 to 30, from 1 to 28, from 1 to 26, from 1 to 24, from 1 to 22, from 1 to 20, from 1 to 18, from 1 to 16, from 1 to 14, from 1 to 12, from 1 to 10, from 1 to 8, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid.

The term "halogen" means F, Cl, Br, or I.

The terms "aralkyl" and "arylalkyl" are used interchangeably and refer to alkyl groups in which a hydrogen atom has been replaced with an aryl group. Such groups include, without limitation, benzyl, cinnamyl, and dihyrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present invention, "aryl" refers to an aromatic ring system which includes, but not limited to, phenyl, biphenyl, naphthyl, anthracyl and the like, which may bear one or more substituents. Also, included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration by injection.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be “acceptable” in the sense of being compatible with the other ingredients of the formulation and not injurious to the patient.

Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; pH buffered solutions; polyesters, polycarbonates and/or polyanhydrides; and other non-toxic compatible substances employed in pharmaceutical formulations.

As used herein, the term “pharmaceutically acceptable salt” refers to those salts which are, within the scope of sound medical judgment, suitable for use in contact with the tissues of humans and lower animals without undue toxicity, irritation, allergic response and the like, and are commensurate with a reasonable benefit/risk ratio.

Unless otherwise stated, structures depicted herein are also meant to include all isomeric (e.g., enantiomeric, diastereomeric, and geometric (or conformational)) forms of the structure; for example, the R and S configurations for each stereocenter; Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided compounds may comprise one or more saccharide moieties. Unless otherwise specified, both D- and L-configurations, and mixtures thereof, are within the scope of the invention. Unless otherwise specified, both α- and β-linked embodiments, and mixtures thereof, are contemplated by the present invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers.

Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13-C- or 14C-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups. By the term “protecting group,” as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6- trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)-amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N',N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, -amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide, (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilyiethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^o$; $—(CH_2)_{0-4}OR^o$; $—O(CH_2)_{0-4}R^o$, $—O—(CH_2)_{0-4}C(O)OR^o$; $—(CH_2)_{0-4}CH(OR^o)_2$; $—(CH_2)_{0-4}SR^o$; $—(CH_2)_{0-4}Ph$, which may be substituted with $R^o$; $—(CH_2)_{0-40}(CH_2)_{0-1}Ph$, which may be substituted with $R^o$; $—CH{=}CHPh$, which may be substituted with $R^o$; $—(CH_2)_{0-4}O(CH_2)_{0-1}$-pyridyl which may be substituted with $R^o$; $—NO_2$; $—CN$; $—N_3$; $—(CH_2)_{0-4}N(R^o)_2$; $—(CH_2)_{0-4}N(R^o)C(O)R^o$; $—N(R^o)C(S)R^o$; $—(CH_2)_{0-4}N(R^o)C(O)NR^o_2$; $—N(R^o)C(S)NR^o_2$; $—(CH_2)_{0-4}N(R^o)C(O)OR^o$; $—N(R^o)N(R^o)C(O)R^o$; $—N(R^o)N(R^o)C(O)NR^o_2$; $—N(R^o)N(R^o)C(O)OR^o$; $—(CH_2)_{0-4}C(O)R^o$; $—C(S)R^o$; $—(CH_2)_{0-4}C(O)OR^o$; $—(CH_2)_{0-4}C(O)SR^o$; $—(CH_2)_{0-4}C(O)OSiR^o_3$; $—(CH_2)_{0-4}OC(O)R^o$; $—OC(O)(CH_2)_{0-4}SR$, $—SC(S)SR^o$; $—(CH_2)_{0-4}SC(O)R^o$; $—(CH_2)_{0-4}C(O)NR^o_2$; $—C(S)NR^o_2$; $—C(S)SR^o$; $—SC(S)SR^o$, $—(CH_2)_{0-4}OC(O)NR^o_2$; $—C(O)N(OR^o)R^o$; $—C(O)C(O)R^o$; $—C(O)CH_2C(O)R^o$; $—C(NOR^o)R^o$; $—(CH_2)_{0-4}SSR^o$; $—(CH_2)_{0-4}S(O)_2R^o$; $—(CH_2)_{0-4}S(O)_{20}R^o$; $—(CH_2)_{0-40}S(O)_2R^o$; $—S(O)_2NR^o_2$; $—(CH_2)_{0-4}S(O)R^o$; $—N(R^o)S(O)_2NR^o_2$; $—N(R^o)S(O)_2R^o$; $—N(OR^o)R^o$; $—C(NH)NR^o_2$; $—P(O)_2R^o$; $—P(O)R^o_2$; $—OP(O)R^o_2$; $—OP(O)(OR^o)_2$; $SiR^o3$; $—(C_{1-4}$ straight or branched)alkylene)O—$N(R^o)_2$; or $—(C_{1-4}$ straight or branched)alkylene)C(O)O—$N(R^o)_2$, wherein each $R^o$ may be substituted as defined below and is independently hydrogen, $C_{1-6}$ aliphatic, $—CH_2Ph$, $—O(CH_2)_{0-1}Ph$, $—CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^o$ (or the ring formed by taking two independent occurrences of $R^o$ together with their intervening atoms), are independently halogen, $—(CH_2)_{0-2}R^\Delta$, -(halo$R^\Delta$), $—(CH_2)_{0-2}OH$, $—(CH_2)_{0-2}OR^\Delta$, $—(CH_2)_{0-2}CH(OR^\Delta)_2$; —O(halo$R^\Delta$), $—CN$, $—N_3$, $—(CH_2)_{0-2}C(O)R^\Delta$, $—(CH_2)_{0-2}C(O)OH$, $—(CH_2)_{0-2}C(O)OR^\Delta$, $—(CH_2)_{0-2}SR^\Delta$, $—(CH_2)_{0-2}SH$, $—(CH_2)_{0-2}NH_2$, $—(CH_2)_{0-2}NHR^\Delta$, $—(CH_2)_{0-2}NR^\Delta_2$, $—NO_2$, $—SiR^\Delta_3$, $—OSiR^\Delta_3$, $—C(O)SR^\Delta_3$, $—(C_{1-4}$ straight or branched alkylene)C(O)$OR^\Delta$, or —SSR. wherein each $R^\Delta$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include =O and =S.

Suitable divalent substituents on a saturated carbon atom of an "optionally substituted" group include the following: =O, =S, =NNR*2, =NNHC(O)R*, =NNHC(O)OR*, $=NNHS(O)_2R^*$, =NR*, =NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $—R^\Delta$, -(halo$R^\Delta$), —OH, $—OR^\Delta$, —O(halo$R^\Delta$), —CN, —C(O)OH, $—C(O)OR^\Delta$, $—NH_2$, $—NHR^\Delta$, $—NR^\Delta_2$, or $—NO_2$, wherein each $R^\Delta$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\backslash_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\backslash_2$, or $—N(R^\backslash)S(O)_2R^\backslash$; wherein each $R^\backslash$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of $R^{\backslash}$ are independently halogen, $—R^{\Delta}$, $-(haloR^{\Delta})$, —OH, $—OR^{\Delta}$, $—O(haloR^{\Delta})$, —CN, —C(O)OH, $—C(O)OR^{\Delta}$, $—NH_2$, $—NHR^{\Delta}$, $—NR^{\Delta}_2$, or $—NO_2$, wherein each $R^{\Delta}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "enriched" as used herein refers to a mixture having an increased proportion of one or more species. In some embodiments, the mixture is "enriched" following a process that increases the proportion of one or more desired species in the mixture. In some embodiments, the desired species comprise(s) greater than 10% of the mixture. In some embodiments, the desired species comprise(s) greater than 25% of the mixture. In some embodiments, the desired species comprise(s) greater than 40% of the mixture. In some embodiments, the desired species comprise(s) greater than 60% of the mixture. In some embodiments, the desired species comprise(s) greater than 75% of the mixture. In some embodiments, the desired species comprise(s) greater than 85% of the mixture. In some embodiments, the desired species comprise(s) greater than 90% of the mixture. In some embodiments, the desired species comprise(s) greater than 95% of the mixture. Such proportions can be measured any number of ways, for example, as a molar ratio, volume to volume, or weight to weight.

The term "pure" refers to compounds that are substantially free of compounds of related non-target structure or chemical precursors (when chemically synthesized). This quality may be measured or expressed as "purity." In some embodiments, a target compound has less than about 30%, 20%, 10%, 5%, 2%, 1%, 0.5%, and 0.1% of non-target structures or chemical precursors. In certain embodiments, a pure compound of present invention is only one prosapogenin compound (i.e., separation of target prosapogenin from other prosapogenins).

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

In another aspect, the present application includes antigens associated with pathogens. In a preferred embodiment, the antigen is associated with the SARS-CoV-2 virus. In another preferred embodiment, the antigen is associated with influenza.

Further objects, features, and advantages of the present application will become apparent form the detailed which is set forth below when considered together with the figures of drawing.

BRIEF DESCRIPTION OF THE DRAWINGS

FIG. 1 depicts the characteristics of a murine study conducted to evaluate the immunological response generated in the various groups shown in the figure. Further information regarding this study is presented in Example 1 of this application.

DETAILED DESCRIPTION OF CERTAIN EMBODIMENTS

Figure 2:
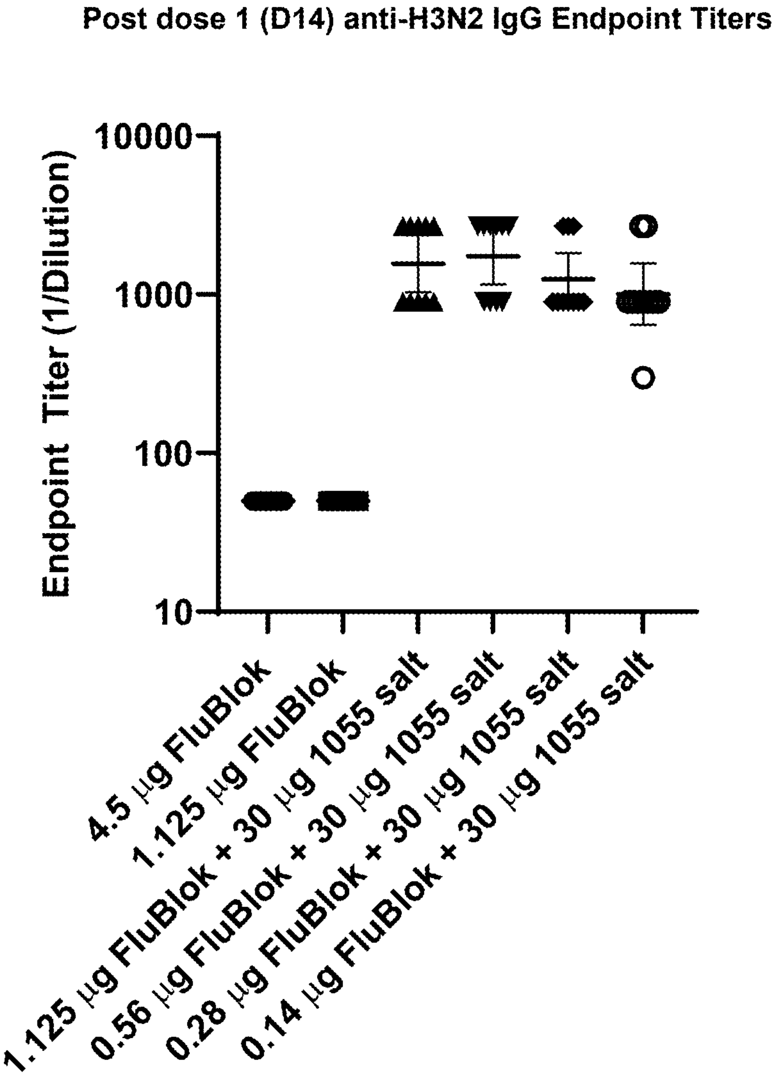
FIG. 2 depicts a chart showing post dose 1 (day 14) anti-H3N2 IgG titers for each group shown in FIG. 1. The data corresponding to this chart are presented in Example 1 of this application.

Compounds Compounds of this invention include those described generally above, and are further illustrated by the classes, subclasses, and species disclosed herein. In some embodiments, provided compounds are analogs of naturally occurring triterpene glycoside saponins and intermediates thereto. For purposes of this invention, the chemical elements are identified in accordance with the Periodic Table of the Elements, CAS version, Handbook of Chemistry and Physics, 75th Ed. Additionally, general principles of organic chemistry are described in Organic Chemistry, Thomas Sorrell, University Science Books, Sausalito: 1999, and March's Advanced Organic Chemistry, 5th Ed., Ed.: Smith, M. B. and March, J., John Wiley & Sons, New York: 2001, the entire contents of which are hereby incorporated by reference.

In some embodiments, provided compounds are analogs of Quillaja saponins. In some embodiments, provided compounds are prosapogenins. In certain embodiments, provided compounds are analogs of QS-7 and QS-21 and possess potent adjuvant activity.

In one aspect, the present application provides compounds of Formula I:

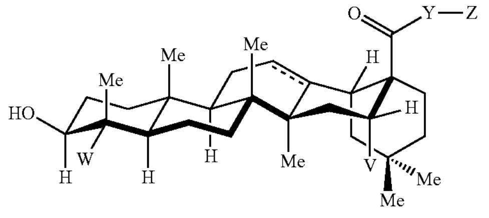
(I)

or a pharmaceutically acceptable salt thereof, wherein

⎓ is a single or double bond;

W is —CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

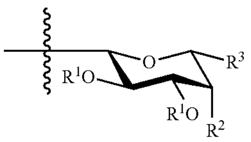

or

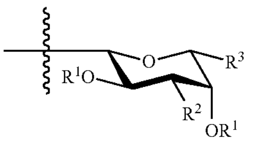

wherein each occurrence of $R^1$ is $R^x$ or a carbohydrate domain having the structure:

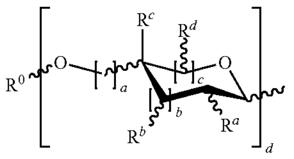

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

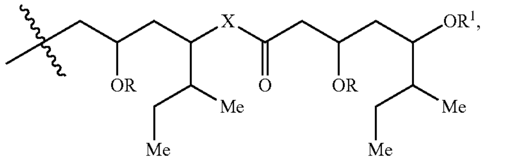

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula II:

(II)

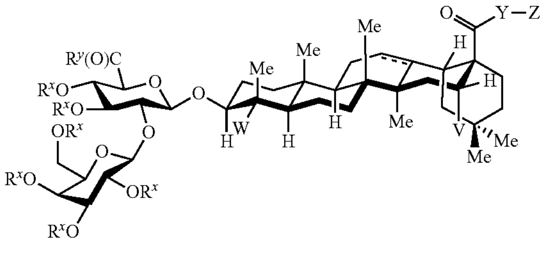

or a pharmaceutically acceptable salt thereof, wherein

⎓ is a single or double bond;

W is Me, —CHO, or

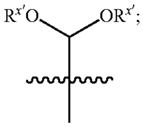

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

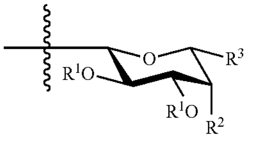
or
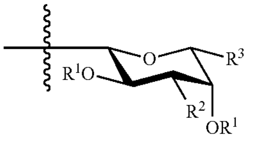

wherein each occurrence of $R^1$ is $R^x$ or a carbohydrate domain having the structure:

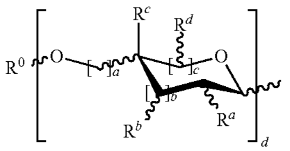

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^C$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

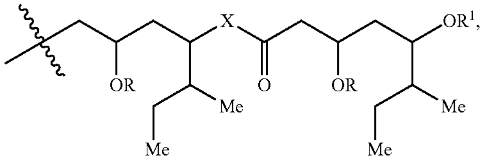

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

$R^y$ is —OH, —OR, or a carboxyl protecting group selected from the group consisting of ester, amides, and hydrazides;

$R^s$ is

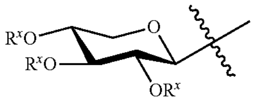
or
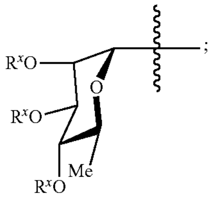
;

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula I:

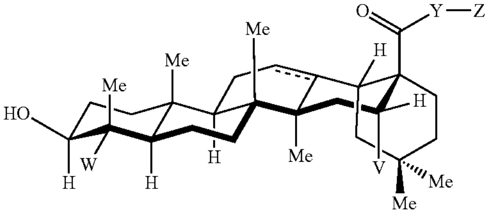

(I)

or a pharmaceutically acceptable salt thereof, wherein

⎓ is a single or double bond;

W is —CHO;

V is —OH;

Y is —O—;

wherein Z is a carbohydrate domain having the structure:

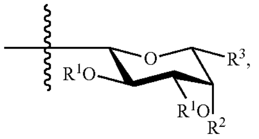

wherein:

$R^1$ is independently H or

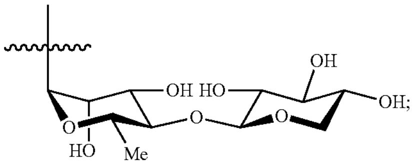

$R^2$ is $NHR^4$;

$R^3$ is $CH_2OH$; and $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

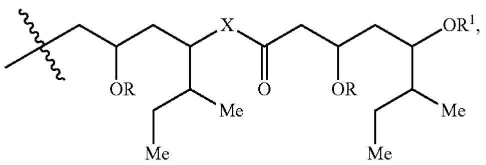

wherein:

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur.

It will be appreciated by one of ordinary skill in the art that the compounds of the present application include but are not necessarily limited to those compounds encompassed in the genus definitions set forth as part of the present section. The compounds encompassed by this application include at least all of the compounds disclosed in the entire specification as a whole, including all individual species within each genus.

In certain embodiments, V is $OR^x$. In certain embodiments V is OH. In certain embodiments, V is H.

In certain embodiments, Y is —O—. In certain embodiments, Y is —NH—. In certain embodiments, Y is —NR—. In certain embodiments, Y is $CH_2$.

In certain embodiments, Z is hydrogen. In certain embodiments, Z is a cyclic or acyclic, optionally substituted moiety. In certain embodiments, Z is an acyl. In certain embodiments, Z is an aliphatic. In certain embodiments, Z is a heteroaliphatic.

In certain embodiments, Z is aryl. In certain embodiments Z is arylalkyl. In certain embodiments, Z is heteroacyl. In certain embodiments, Z is heteroaryl. In certain embodiments, Z is a carbohydrate domain having the structure:

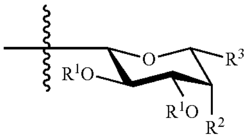

or

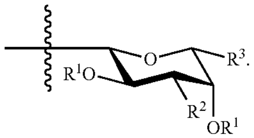

In some embodiments Z is a carbohydrate domain having the structure:

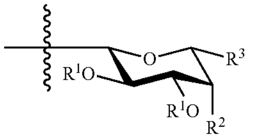

wherein:

$R^1$ is independently H or

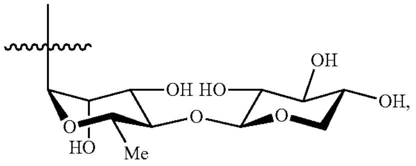

$R^2$ is $NHR^4$, $R^3$ is $CH_2OH$, and $R^4$ is selected from:

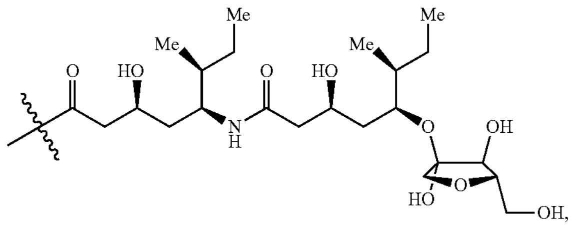

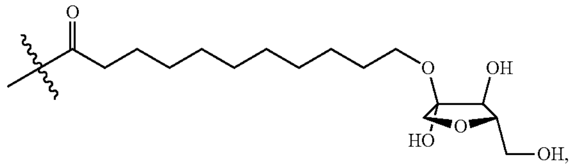

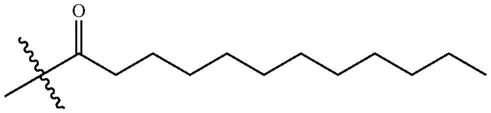
,

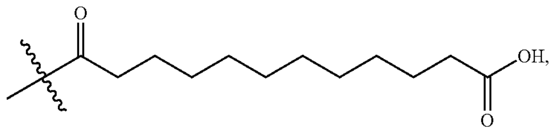

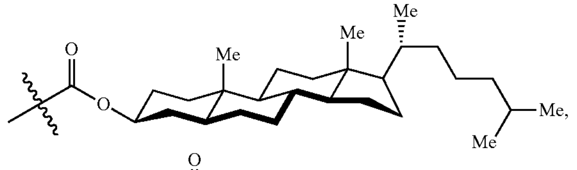

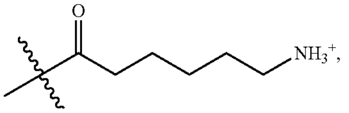

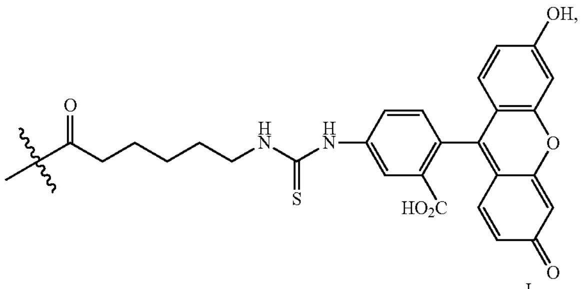

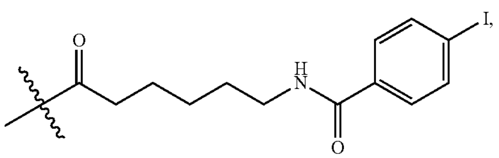

-continued

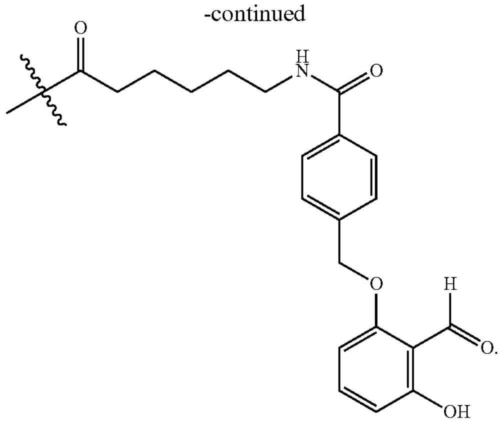

In some embodiments, $R^1$ is $R^x$. In other embodiments, $R^1$ a carbohydrate domain having the structure:

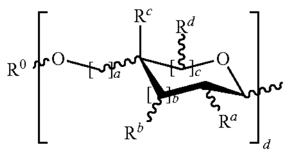

In some aspects, each occurrence of a, b, and c is independently 0, 1, or 2. In some embodiments, d is an integer from 1-5. In some embodiments, each d bracketed structure may be the same. In some embodiments, each d bracketed structure may be different. In some embodiments, the d bracketed structure represents a furanose or a pyranose moiety. In some embodiments, and the sum of b and c is 1 or 2.

In some embodiments, $R^0$ is hydrogen. In some embodiments, $R^0$ is an oxygen protecting group selected from the group. In some embodiments, $R^0$ is an alkyl ether. In some embodiments, $R^0$ is a benzyl ether. In some embodiments, $R^0$ is a silyl ether. In some embodiments, $R^0$ is an acetal. In some embodiments, $R^0$ is ketal. In some embodiments, $R^0$ is an ester. In some embodiments, $R^0$ is a carbamate. In some embodiments, $R^0$ is a carbonate. In some embodiments, $R^0$ is an optionally substituted moiety. In some embodiments, $R^0$ is an acyl. In some embodiments, $R^0$ is a $C_{1-10}$ aliphatic. In some embodiments, $R^0$ is a $C_{1-6}$ heteroaliphatic. In some embodiments, $R^0$ is a 6-10-membered aryl. In some embodiments, $R^0$ is an arylalkyl. In some embodiments, $R^0$ is a 5-10 membered heteroaryl having 1-4 heteroatoms independently selected from nitrogen, oxygen, or sulfur. In some embodiments, $R^0$ is a 4-7 membered heterocyclyl having 1-2 heteroatoms independently selected from the group consisting of nitrogen, oxygen, and sulfur.

In some embodiments, $R^a$ is hydrogen. In some embodiments, $R^a$ is a halogen. In some embodiments, $R^a$ is OH. In some embodiments, $R^a$ is OR. In some embodiments, $R^a$ is $OR^x$. In some embodiments, $R^a$ is $NR_2$. In some embodiments, $R^a$ is NHCOR. In some embodiments, $R^a$ an acyl. In some embodiments, $R^a$ is $C_{1-10}$ aliphatic. In some embodiments, $R^a$ is $C_{1-6}$ heteroaliphatic. In some embodiments, $R^a$ is 6-10-membered aryl. In some embodiments, $R^a$ is arylalkyl. In some embodiments, $R^a$ is 5-10-membered heteroaryl having 1-4 heteroatoms independently selected from nitrogen, oxygen, sulfur. In some embodiments, $R^a$ is 4-7- membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^o$ is hydrogen. In some embodiments, $R^c$ is a halogen.

In some embodiments, $R^c$ is OH. In some embodiments, $R^o$ is OR. In some embodiments, $R^o$ is $OR^x$. In some embodiments, $R^o$ is $NR_2$. In some embodiments, $R^c$ is NHCOR. In some embodiments, $R^C$ an acyl. In some embodiments, $R^o$ is $C_{1-10}$ aliphatic. In some embodiments, $R^o$ is $C_{1-6}$ heteroaliphatic. In some embodiments, $R^o$ is 6-10-membered aryl. In some embodiments, $R^o$ is arylalkyl. In some embodiments, $R^o$ is 5-10-membered heteroaryl having 1-4 heteroatoms independently selected from nitrogen, oxygen, sulfur. In some embodiments, $R^o$ is 4-7-membered heterocyclyl having 1-2 heteroatoms independently selected from the group consisting of nitrogen, oxygen, and sulfur.

In some embodiments, $R^d$ is hydrogen. In some embodiments, $R^d$ is a halogen. In some embodiments, $R^d$ is OH. In some embodiments, $R^d$ is OR. In some embodiments, $R^d$ is $OR^x$. In some embodiments, $R^d$ is $NR_2$. In some embodiments, $R^d$ is NHCOR. In some embodiments, $R^d$ an acyl. In some embodiments, $R^d$ is $C_{1-10}$ aliphatic. In some embodiments, $R^d$ is $C_{1-6}$ heteroaliphatic. In some embodiments, $R^d$ is 6-10-membered aryl. In some embodiments, $R^d$ is arylalkyl. In some embodiments, $R^d$ is 5-10-membered heteroaryl having 1-4 heteroatoms independently selected from nitrogen, oxygen, sulfur. In some embodiments, $R^d$ is 4-7-membered heterocyclyl having 1-2 heteroatoms independently selected from the group consisting of nitrogen, oxygen, and sulfur.

In some embodiments, $R^2$ is hydrogen. In some embodiments, $R^2$ is a halogen. In some embodiments, $R^2$ is OH. In some embodiments, $R^2$ is OR. In some embodiments, $R^2$ is $OC(O)R^4$. In some embodiments, $R^2$ is $OC(O)OR^4$. In some embodiments, $R^2$ is $OC(O)NHR^4$. In some embodiments, $R^2$ is $OC(O)NRR^4$. In some embodiments, $R^2$ is $OC(O)SR^4$. In some embodiments, $R^2$ is $NHC(O)R^4$. In some embodiments, $R^2$ is $NRC(O)R^4$. In some embodiments, $R^2$ is $NHC(O)OR^4$. In some embodiments, $R^2$ is $NHC(O)NHR^4$. In some embodiments, $R^2$ is $NHC(O)NRR^4$. In some embodiments, $R^2$ is $NHR^4$. In some embodiments, $R^2$ is $N(R^4)_2$. In some embodiments, $R^2$ is $NHR^4$—In some embodiments, $R^2$ is $NRR^4$. In some embodiments, $R^2$ is $N_3$. In some embodiments, $R^2$ is $C_{1-10}$ aliphatic. In some embodiments, $R^2$ is $C_1$-6 heteroaliphatic. In some embodiments, $R^2$ is 6-10-membered aryl. In some embodiments, $R^2$ is arylalkyl. In some embodiments, $R^2$ is 5-10 membered heteroaryl having 1-4 heteroatoms independently selected from the group consisting of nitrogen, oxygen, and sulfur. In some embodiments, $R^2$ is 4-7-membered heterocyclyl having 1-2 heteroatoms independently selected from the group consisting of nitrogen, oxygen, and sulfur.

In some embodiments, $R^3$ is hydrogen. In some embodiments, $R^3$ is a halogen. In some embodiments, $R^3$ is $CH_2OR^1$. In some embodiments, $R^3$ is an acyl. In some embodiments, $R^3$ is $C_{1-10}$ aliphatic. In some embodiments, $R^3$ is $C_{1-6}$ heteroaliphatic. In some embodiments, $R^3$ is 6-10-membered aryl. In some embodiments, $R^3$ is arylalkyl. In some embodiments, $R^3$ is 5-10-membered heteroaryl having 1-4 heteroatoms independently selected from the group consisting of nitrogen, oxygen, and sulfur. In some embodiments, $R^3$ is 4-7-membered heterocyclyl having 1-2 heteroatoms independently selected from the group consisting of nitrogen, oxygen, and sulfur.

In some embodiments, $R^4$ is $-T-R^z$. In some embodiments, $R^4$ is $—C(O)-T-R^z$. In some embodiments, $R^4$ is $—NH-T-R^z$. In some embodiments, $R^4$ is $—O-T-R^z$. In some embodiments, $R^4$ is $—S-T-R^z$. In some embodiments, $R^4$ is $—C(O)NH-T-R^z$. In some embodiments, $R^4$ is $C(O)O-T-R^z$. In some embodiments, $R^4$ is $C(O)S-T-R^z$. In some embodiments, $R^4$ is $C(O)NH-T-O-T-R^z$. In some embodiments, $R^4$ is $—O-T-R^z$. In some embodiments, $R^4$ is $-T-O-T-R^z$. In some embodiments, $R^4$ is $-T-S-T-R^z$. In some embodiments, $R^4$ is

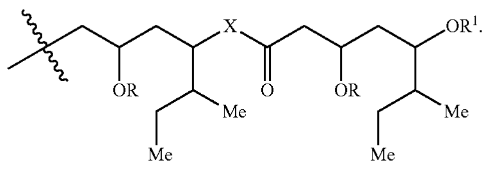

In some embodiments, X is —O—. In some embodiments, X is —NR—. In some embodiments, X is $T-R^z$.

In some embodiments, T is a covalent bond or a bivalent $C_{1-26}$ saturated or unsaturated, straight or branched, aliphatic or heteroaliphatic chain.

In some embodiments, $R^z$ is hydrogen. In some embodiments, $R^z$ is a halogen. In some embodiments, $R^z$ is —OR. In some embodiments, $R^z$ is $—OR^x$. In some embodiments, $R^z$ is $—OR^1$. In some embodiments, $R^z$ is $—OR^{1''}$. In some embodiments, $R^z$ is —SR. In some embodiments, $R^z$ is $NR_2$. In some embodiments, $R^z$ is —C(O)OR. In some embodiments, $R^z$ is —C(O)R. In some embodiments, $R^z$ is —NHC(O)R. Insome embodiments, $R^z$ is —NHC(O)OR. In some embodiments, $R^z$ is NC(O)OR. In some embodiments, $R^z$ is an acyl. In some embodiments, $R^z$ is arylalkyl. In some embodiments, $R^z$ is heteroarylalkyl. In some embodiments, $R^z$ is $C_{1-6}$ aliphatic. In some embodiments, $R^z$ is 6-10-membered aryl. In some embodiments, $R^z$ is 5-10-membered heteroaryl having 1-4 heteroatoms independently selected from nitrogen, oxygen, or sulfur. In some embodiments, $R^z$ is 4-7-membered heterocyclyl having 1-2 heteroatoms independently selected from the group consisting of nitrogen, oxygen, and sulfur.

In some embodiments, $R^x$ is hydrogen. In some embodiments, $R^x$ is an oxygen protecting group. In some embodiments, $R^x$ is an alkyl ether. In some embodiments, $R^x$ is a benzyl ether. In some embodiments, $R^x$ is silyl ether. In some embodiments, $R^x$ is an acetal. In some embodiments, $R^x$ is ketal. In some embodiments, $R^x$ is ester. In some embodiments, $R^x$ is carbamate. In some embodiments, $R^x$ is carbonate.

In some embodiments, $R^y$ is —OH. In some embodiments, $R^y$ is —OR. In some embodiments, $R^y$ is a carboxyl protecting group. In some embodiments, $R^y$ is an ester. In some embodiments, $R^Y$ is an amide. In some embodiments, $R^y$ is a hydrazide.

In some embodiments, $R^s$ is

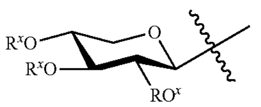

or

-continued

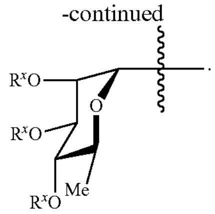

In some embodiments, $R^{x'}$ is optionally substituted 6-10-membered aryl. In some embodiments, $R^{x'}$ is optionally substituted $C_{1-6}$ aliphatic. In some embodiments, $R^{x'}$ is optionally substituted or $C_{1-6}$ heteroaliphatic having 1-2 heteroatoms independently selected from the group consisting of nitrogen, oxygen, and sulfur. In some embodiments, two $R^{x'}$ are taken together to form a 5-7-membered heterocyclic ring having 1-2 heteroatoms independently selected from the group consisting of nitrogen, oxygen, and sulfur.

In some embodiments, R is hydrogen. In some embodiments, R is an acyl. In some embodiments, R is arylalkyl. In some embodiments, R is 6-10-membered aryl. In some embodiments, R is $C_{1-6}$ aliphatic. In some embodiments, R is $C_{1-6}$ heteroaliphatic having 1-2 heteroatoms independently selected from the group consisting of nitrogen, oxygen, and sulfur. In some embodiments, two R on the same nitrogen atom are taken with the nitrogen atom to form a 4-7-membered heterocyclic ring having 1-2 heteroatoms independently selected from the group consisting of nitrogen, oxygen, and sulfur.

In some embodiments, $R^{1''}$ has the same embodiments as $R^1$.

Exemplary compounds of Formula I are set forth in Table 1 below:

TABLE 1

| EXEMPLARY COMPOUNDS OF FORMULA I | |
|---|---|
| 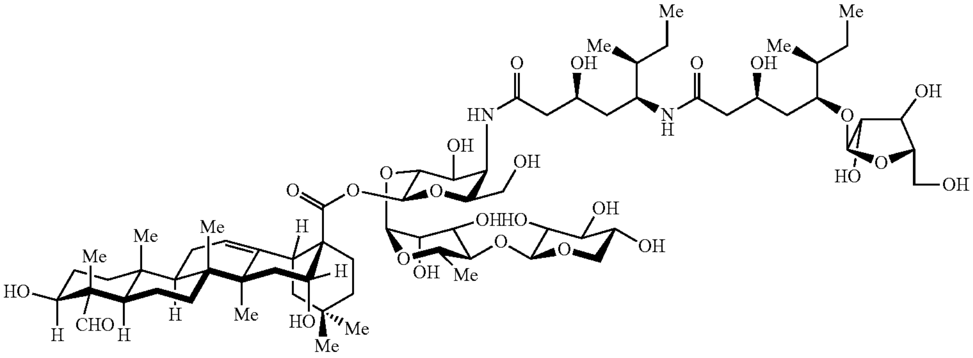 | I-1 |
| 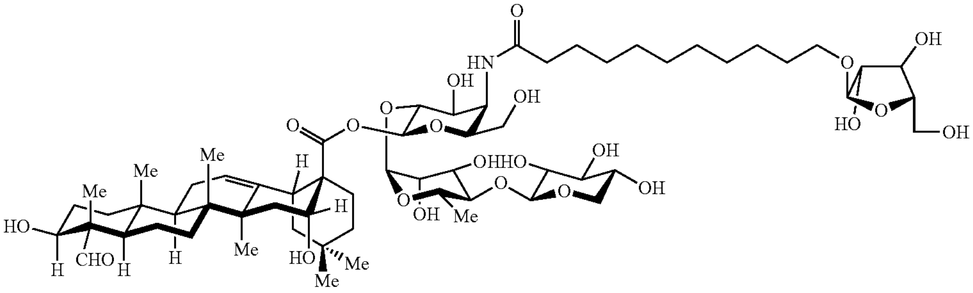 | I-2 |

TABLE 1-continued
| EXEMPLARY COMPOUNDS OF FORMULA I |
| --- |
| 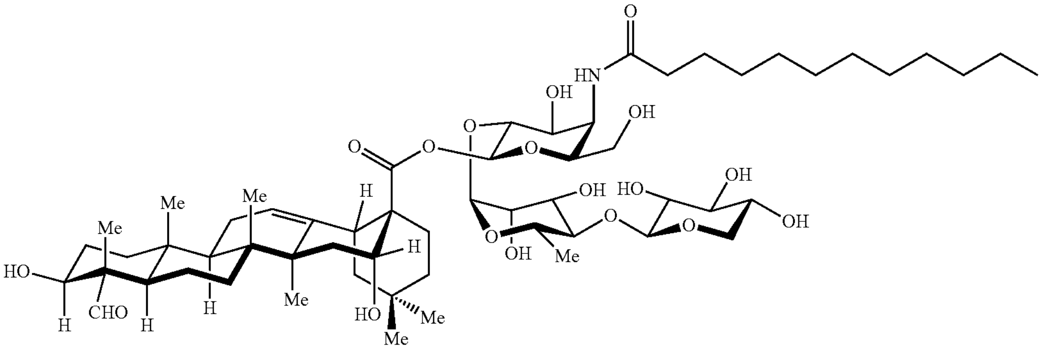 I-3 |
| 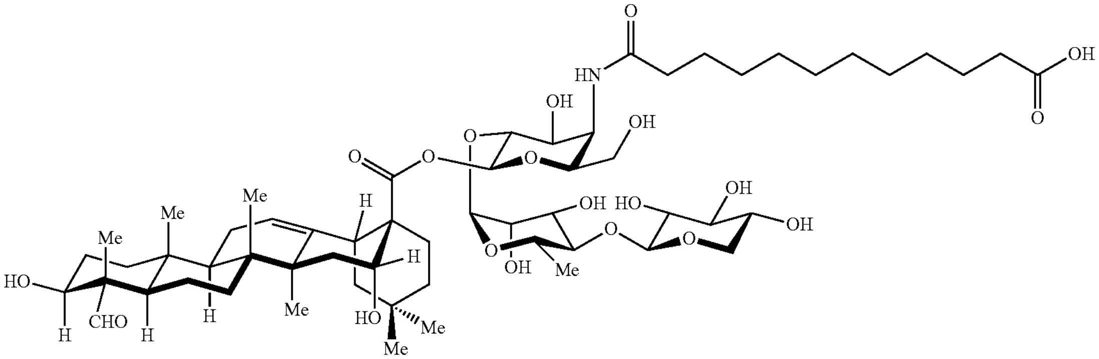 I-4 |
| 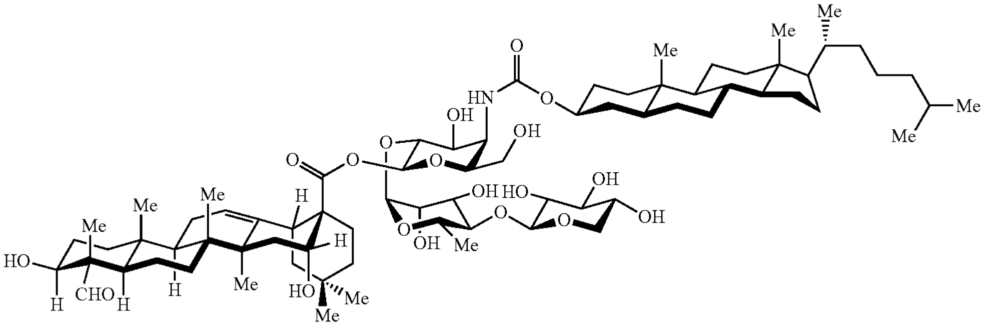 I-5 |
| 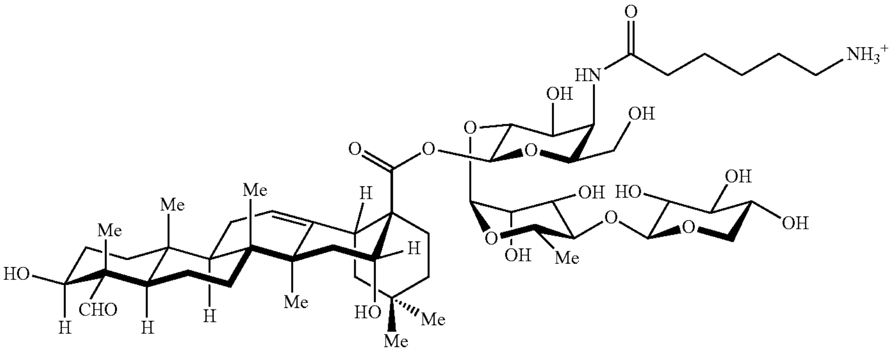 I-6 |

TABLE 1-continued
EXEMPLARY COMPOUNDS OF FORMULA I
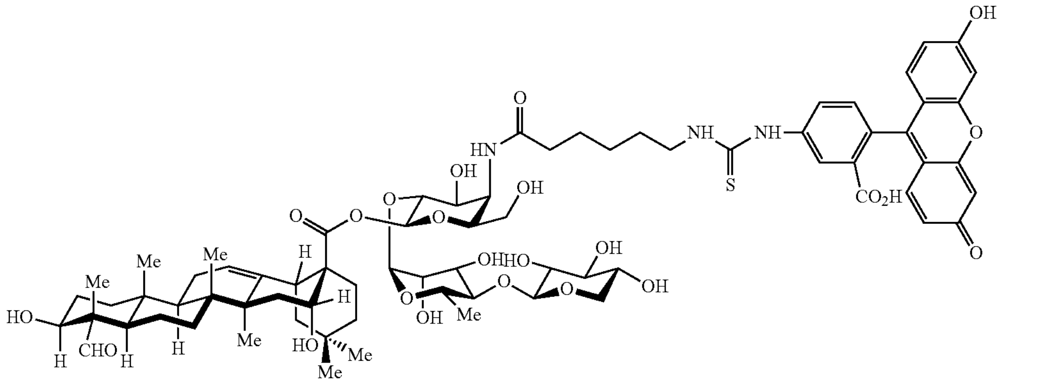
I-7
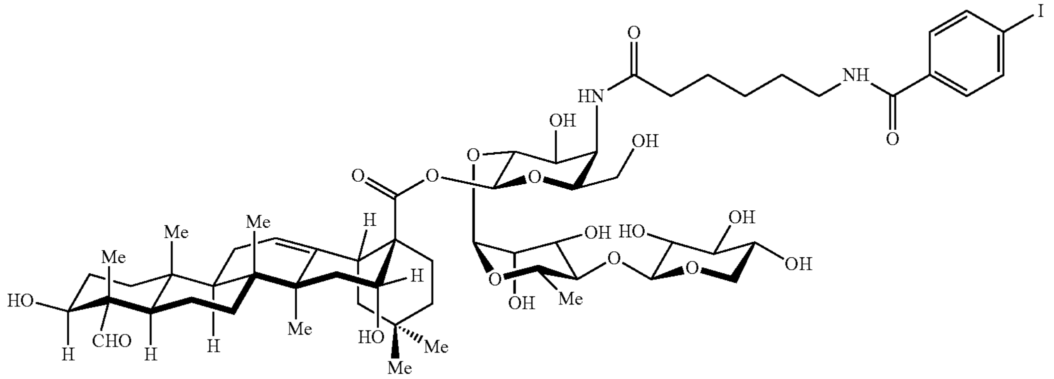
I-8
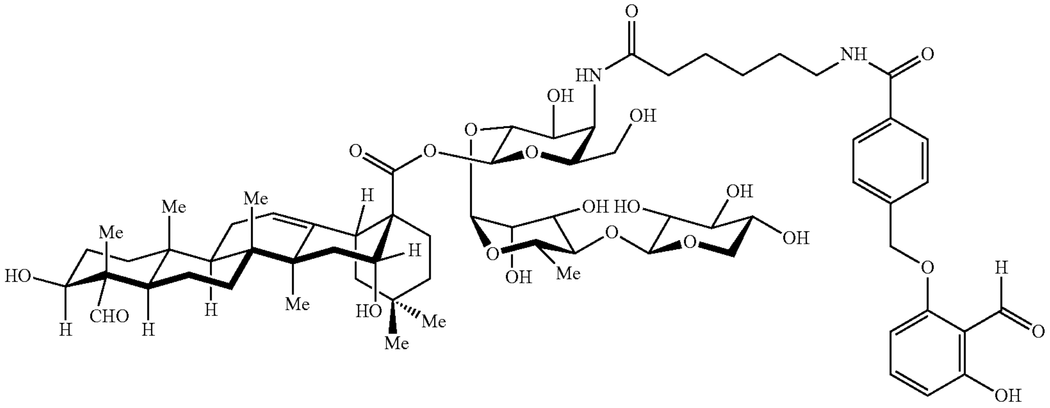
I-9
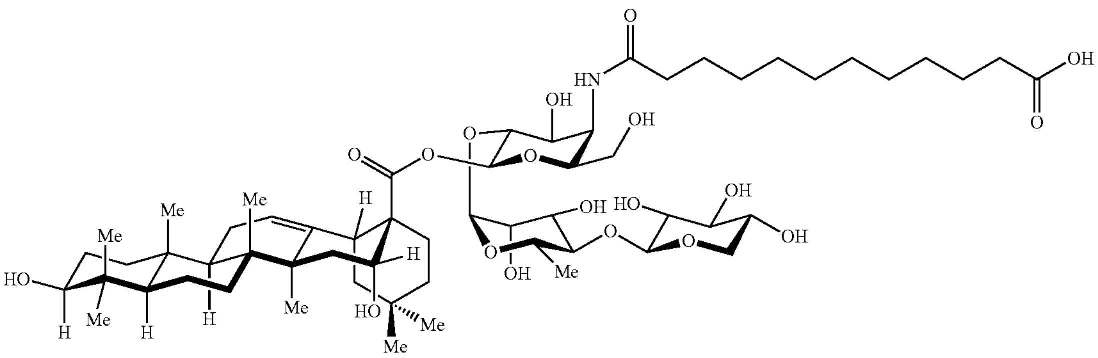
I-10
It will be appreciated that it is not an object of the present subject matter to claim compounds disclosed in the prior art that are the result of isolation or degradation studies on naturally occurring prosapogenins or saponins.

Synthesis

The compounds of the present application may be synthesized as provided in PCT/US2009/039954, PCT/US2015/33567, PCT/US2016/67530, PCT/US2016/60564, and/or PCT/US2018/027462.

Adjuvants

The present application encompasses the recognition that synthetic access to and structural modification of QS-21 and related Quillaja saponins may afford compounds with high adjuvant potency and low toxicity, as well as having more stability and. being more cost effective. Accordingly, compounds of the present application, including TQL-1055, have industrial applicability and are useful as adjuvants, in free form acid or base form or in pharmaceutically acceptable salt form.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically-acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and $N+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Representative organic amines useful for the formation of base addition salts include ethylamine, diethylamine, ethylenediamine, ethanolamine, diethanolamine, piperazine and the like.

Further pharmaceutically acceptable salts include, when appropriate, choline, L-lysine, magnesium, meglumine, potassium, sodium, and TEA.

Certain embodiments of the present application include salt forms of synthetic saponin-derived adjuvants. In some embodiments, the adjuvants are compounds of Formula I as described herein. In some embodiments, the adjuvant is the compound TQL-1055.

Vaccines

Compositions in this application and their pharmaceutically acceptable salts are useful as vaccines to induce active immunity towards antigens in subjects. Any animal that may experience the beneficial effects of the compositions of the present application is within the scope of subjects that may be treated. In some embodiments, the subjects are mammals. In some embodiments, the subjects are humans.

The vaccines of the present application may be used to confer resistance to infection by either passive or active immunization. When the vaccines of the present application are used to confer resistance through active immunization, a vaccine of the present application is administered to an animal to elicit a protective immune response which either prevents or attenuates a proliferative or infectious disease. When the vaccines of the present application are used to confer resistance to infection through passive immunization, the vaccine is provided to a host animal (e.g., human, dog, or mouse), and the antisera elicited by this vaccine is recovered and directly provided to a recipient suspected of having an infection or disease or exposed to a causative organism.

The present application thus concerns and provides a means for preventing or attenuating a proliferative disease resulting from organisms which have antigens that are recognized and bound by antisera produced in response to the immunogenic antigens included in vaccines of the present application. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of proliferative disease. The prophylactic administration of the vaccine(s) serves to prevent or attenuate any subsequent presentation of the disease. When provided therapeutically, the vaccine(s) is provided upon or after the detection of symptoms which indicate that an animal may be infected with a pathogen. The therapeutic administration of the vaccine(s) serves to attenuate any actual disease presentation. Thus, the vaccines may be provided either prior to the onset of disease proliferation (so as to prevent or attenuate an anticipated infection) or after the initiation of an actual proliferation.

One of ordinary skill in the art will appreciate that vaccines may optionally include a pharmaceutically acceptable excipient or carrier. Thus, according to another aspect, provided vaccines may comprise one or more antigens that are optionally conjugated to a pharmaceutically acceptable excipient or carrier. In some embodiments, said one or more antigens are conjugated covalently to a pharmaceutically acceptable excipient. In other embodiments, said one or more antigens are non-covalently associated with a pharmaceutically acceptable excipient.

As described above, adjuvants may be used to increase the immune response to an antigen. According to the present application, provided vaccines may be used to invoke an immune response when administered to a subject. In certain embodiments, an immune response to an antigen may be potentiated by administering to a subject a provided vaccine in an effective amount to potentiate the immune response of said subject to said antigen.

Formulations

The compounds of the present application and/or their salts may be combined with a pharmaceutically acceptable excipient to form a pharmaceutical composition. In certain embodiments, formulations of the present application include injectable formulations. In certain embodiments, the pharmaceutical composition includes a pharmaceutically acceptable amount of a compound of the present application. In certain embodiments, the compounds of the application and an antigen form an active ingredient. In certain embodiments, the compound of the present application alone forms an active ingredient. The amount of active ingredient(s) which can be combined with a carrier material to produce a single dosage form will vary depending upon the host being treated, and the particular mode of administration. The amount of active ingredient(s) that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%, or from about 1% to 99%, preferably from 10% to 90%, 20% to 80%, 30% to 70%, 40% to 60%, 45% to 55%, or about 50%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Thus, in one aspect the present application provides formulations comprising a liposome formulation of MPL and Compound 1-4. In another aspect the present application provides formulations comprising MPL, Compound 1-4, and a squalene emulsion. In another aspect the present application provides formulations comprising MPL, Compound 1-4, and CpG 7909 or CpG 1018. MPL is a heterogeneous mixture of molecules from a biological source including both agonists and antagonists for TLR4. CpG 7909 is an immunomodulating synthetic oligonucleotide designed to specifically agonise the Toll-like receptor 9 (TLR9).

Liposomal formulations of MPL and naturally occurring QS-21 are formulated, for example, by first producing liposomes by mixing methanol and a cholesterol. Liposomes are closed bilayer membranes containing an entrapped aqueous volume. Liposomes may also be uni-lamellar vesicles possessing a single membrane bilayer or multi-lamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose, hydroxyethylcellulose, polyethyleneglycol, polyaspartamide and hydrophilic peptide sequences as described in U.S. Pat. Nos. 6,316,024; 6,126,966; 6,056,973; and 6,043,094. Liposomes can be made without hydrophilic polymers. Therefore, liposome formulations may or may not contain hydrophilic polymers.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatide acid, phosphatidylserine, phosphatidylglycerol, phosphatidylinositol, and sphingomyelin as disclosed in U.S. Pat. Nos. 6,056,973 and 5,874,104.

The vesicle-forming lipids may also be glycolipids, cerebrosides, or cationic lipids, such as 1,2-dioleyloxy-3-(trimethylamino)propane (DOTAP); N—[I-(2,3-ditetradecyloxy)propyl]-N,N-dimethyl-N-hydroxyethylammonium bromide (DMRIE); N—[I [(2,3-dioleyloxy)propyl]-N,N-dimethyl-N-hydroxy ethylammonium bromide (DORIE); N—[I-(2,3-dioleyloxy)propyl]-N,N,N-trimethylammonium chloride (DOTMA); 3 [N—(N',N'-dimethylaminoethane) carbamoly]cholesterol (DCChol); or dimethyldioctadecylammonium (DDAB) also as disclosed in U.S. Pat. No. 6,056,973. Cholesterol may also be present in the proper range to impart stability to the liposome vesicle, as disclosed in U.S. Pat. Nos. 5,916,588 and 5,874,104. Additional liposomal technologies are described in U.S. Pat. Nos. 6,759,057; 6,406,713; 6,352,716; 6,316,024; 6,294,191; 6,126,966; 6,056,973; 6,043,094; 5,965,156; 5,916,588; 5,874,104; 5,215,680; and 4,684,479. These described liposomes and lipid-coated microbubbles, and methods for their manufacture. Thus, one skilled in the art, considering both the present disclosure and the disclosures of these other patents could produce a liposome for the purposes of the present embodiments. Liposomes may comprise phospholipid or nonphospholipid bilayers.

Phospholipid bilayers may comprise hydrocarbon chains, optionally having a melting temperature in water of at least 23° C. Such phospholipids may comprise, for example, dimyristoyl phosphatidylcholine (DMPC), dimyristoyl phosphatidylglycerol (DMPG), cholesterol (Chol), or similar molecules, and mixtures thereof. The liposome may optionally comprise a neutral lipid that is non-crystalline at room temperature, such as dioleoyl phosphatidylcholine or similar compounds. See U.S. Published Patent Application No. 201 1/0206758.

During manufacture of liposomal formulations containing, for example, QS-21, small unicellular liposomal vesicles (SUV) are first created. The SUV is then added to an aqueous environment having QS-21 or another saponin and the SUV takes up QS-21 or the saponin from the aqueous environment. The liposomal composition also may have certain optional ingredients, such as for example MPL, synthetic MPL such as MPLA, CpG 7909 or CpG 1018, or similar substances.

However, formulation of liposomal formulations containing other saponin derivatives such as Compound 1-4 surprisingly cannot be accomplished using procedures known in the art, because the SUV or liposomal formulations do not take up such saponin derivatives, resulting in SUV or liposomes without the saponin derivative molecule. Thus, another aspect of the present application provides a novel method of producing liposomal formulations of saponin derivates that cannot be formulated using traditional methods. In such a method, the SUVs or liposomes are first formulated with the presence of a saponin derivative such as Compound 1-4. For example, the SUV may be formulated by combining a lipid such as a cholesterol and methanol in the presence of Compound 1-4. The SUV may also be formulated according to the traditional method as set forth above; however, the SUV is formulated in the presence of a saponin derivative such as QS-21. These SUV or liposomes form with Compound 1-4 incorporated therein. Such SUV or liposomes are then added to an aqueous environment having, for example, MPL or other compositions as set forth above.

Non-limiting examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Non-limiting examples of suitable aqueous and nonaqueous carriers, which may be employed in the pharmaceutical compositions of the present application include water, alcohols (including but not limited to methanol, ethanol, butanol, etc.), polyols (including but not limited to glycerol, propylene glycol, polyethylene glycol, etc.), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain additives such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a formulation, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form.

Regardless of the route of administration selected, the compounds of the present application, which may be used in a suitable hydrated form, and/or the pharmaceutical compositions of the present application, are formulated into pharmaceutically-acceptable dosage forms by conventional methods known to those of skill in the art.

Actual dosage levels of the active ingredients in the pharmaceutical compositions of the present application may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present application employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the present application employed in the pharmaceutical composition at levels lower than that required to achieve the desired therapeutic effect and then gradually increasing the dosage until the desired effect is achieved.

In some embodiments, a compound or pharmaceutical composition of the present application is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the present application repeatedly over the life of the subject. Preferred chronic treatments involve regular administrations, for example one or more times a day, one or more times a week, or one or more times a month. In general, a suitable dose, such as a daily dose of a compound of the present application, will be that amount of the compound that is the lowest dose effective to produce a therapeutic effect. Such an effective dose will generally depend upon the factors described above.

Generally, doses of the compounds of the present application for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, provided adjuvant compounds of the present application are administered as pharmaceutical compositions or vaccines. In certain embodiments, it is contemplated that the amount of adjuvant compound administered will be 1-2000 μg. In certain embodiments, it is contemplated that the amount of adjuvant compound administered will be 1-1000 μg. In certain embodiments, it is contemplated that the amount of adjuvant compound administered will be 1-500 μg. In certain embodiments, it is contemplated that the amount of adjuvant compound administered will be 1-250 μg. In certain embodiments, it is contemplated that the amount of adjuvant compound administered will be 100-1000 μg. In certain embodiments, it is contemplated that the amount of adjuvant compound administered will be 100-500 μg. In certain embodiments, it is contemplated that the amount of adjuvant compound administered will be 100-200 μg. In certain embodiments, it is contemplated that the amount of adjuvant compound administered will be 250-500 μg. In certain embodiments, it is contemplated that the amount of adjuvant compound administered will be 10-1000 μg. In certain embodiments, it is contemplated that the amount of adjuvant compound administered will be 500-1000 μg. In certain embodiments, it is contemplated that the amount of adjuvant compound administered will be 50-250 μg. In certain embodiments, it is contemplated that the amount of adjuvant compound administered will be 50-500 μg.

In some embodiments, provided adjuvant compounds of the present application are administered as pharmaceutical compositions or vaccines. In certain embodiments, it is contemplated that the amount of adjuvant compound administered will be 1-2000 mg. In certain embodiments, it is contemplated that the amount of adjuvant compound administered will be 1-1000 mg. In certain embodiments, it is contemplated that the amount of adjuvant compound administered will be 1-500 mg. In certain embodiments, it is contemplated that the amount of adjuvant compound administered will be 1-250 mg. In certain embodiments, it is contemplated that the amount of adjuvant compound administered will be 100-1000 mg. In certain embodiments, it is contemplated that the amount of adjuvant compound administered will be 100-500 mg. In certain embodiments, it is contemplated that the amount of adjuvant compound administered will be 100-200 mg. In certain embodiments, it is contemplated that the amount of adjuvant compound administered will be 250-500 mg. In certain embodiments, it is contemplated that the amount of adjuvant compound administered will be 10-1000 mg. In certain embodiments, it is contemplated that the amount of adjuvant compound administered will be 500-1000 mg. In certain embodiments, it is contemplated that the amount of adjuvant compound administered will be 50-250 mg. In certain embodiments, it is contemplated that the amount of adjuvant compound administered will be 50-500 mg. In certain embodiments, it is contemplated that the amount of adjuvant compound administered will be 0.01-215.4 mg.

In certain embodiments, it is contemplated that the amount of adjuvant administered will be 1000-5000 μg/kg. In certain embodiments, it is contemplated that the amount of adjuvant administered will be 1000-4000 μg/kg. In certain embodiments, it is contemplated that the amount of adjuvant administered will be 1000-3000 μg/kg. In certain embodiments, it is contemplated that the amount of adjuvant administered will be 1000-2000 μg/kg. In certain embodiments, it is contemplated that the amount of adjuvant administered will be 2000-5000 μg/kg. In certain embodiments, it is contemplated that the amount of adjuvant administered will be 2000-4000 μg/kg. In certain embodiments, it is contemplated that the amount of adjuvant administered will be 2000-3000 μg/kg. In certain embodiments, it is contemplated that the amount of adjuvant administered will be 3000-5000 μg/kg. In certain embodiments, it is contemplated that the amount of adjuvant administered will be 3000-4000 μg/kg. In certain embodiments, it is contemplated that the amount of adjuvant administered will be 4000-5000 μg/kg. In certain embodiments, it is contemplated that the amount of adjuvant administered will be 1-500 μg/kg. In certain embodiments, it is contemplated that the amount of adjuvant administered will be 500-1000 μg/kg. In certain embodiments, it is contemplated that the amount of adjuvant administered will be 1000-1500 μg/kg. In certain embodiments, it is contemplated that the amount of adjuvant administered will be 1 mg/kg. In certain embodiments, it is contemplated that the amount of adjuvant administered will be 2 mg/kg. In certain embodiments, it is contemplated that the amount of adjuvant administered will be 3 mg/kg. In certain embodiments, it is contemplated that the amount of adjuvant administered will be 4 mg/kg. In certain embodiments, it is contemplated that the amount of adjuvant administered will be 5 mg/kg. In certain embodiments, it is contemplated that the amount of adjuvant administered will be 0.0029-5 mg/kg. In certain embodiments, the amount of adjuvant administered in females is less than the amount of adjuvant administered in males. In certain embodiments, the amount of adjuvant administered to infants is less than the amount of adjuvant administered to adults. In certain embodiments, the amount of adjuvant administered to pediatric recipients is less than the amount of adjuvant administered to adults. In certain embodiments, the amount of adjuvant administered to immunocompromised recipients is more than the amount of adjuvant administered to healthy recipients. In certain embodiments, the amount of adjuvant administered to elderly recipients is more than the amount of adjuvant administered to non-elderly recipients.

If desired, the effective dose of the active compound may be administered as two, three, four, five, six or more sub-doses administered separately at appropriate intervals throughout the day, optionally, in unit dosage forms.

While it is possible for a compound of the present application to be administered alone, in certain embodiments the compound is administered as a pharmaceutical formulation or composition as described above.

The compounds according to the present application may be formulated for administration in any convenient way for use in human or veterinary medicine, by analogy with other pharmaceuticals.

The present application provides kits comprising pharmaceutical formulations or compositions of a compound of the present application. In certain embodiments, such kits include the combination of a compound of formulae I and/or II and an antigen.

The agents may be packaged separately or together. The kit optionally includes instructions for prescribing the medication. In certain embodiments, the kit includes multiple doses of each agent. The kit may include sufficient quantities of each component to treat one or more subject for a week, two weeks, three weeks, four weeks, or multiple months. The kit may include a full cycle of immunotherapy. In some embodiments, the kit includes a vaccine comprising one or more bacterial or viral-associated antigens, and one or more provided compounds.

Antigen Dose-Sparing

The present application also provides pharmaceutical compositions that demonstrate an antigen dose-sparing effect. Such pharmaceutical compositions may include the compounds or compositions of the present application in combination with an antigen. Preferably, the pharmaceutical compositions include TQL-1055:

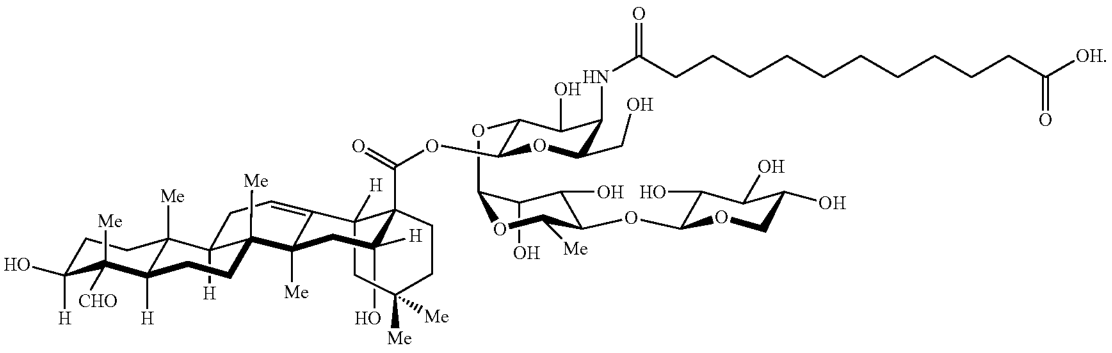

In some embodiments, the amount of antigen provided is less than the amount of antigen required in the absence of the compound of Formula I. In some embodiments, the amount of antigen provided is about 95%, 90%, 85%, 80%, 75%, 70%, 67%, 65%, 60%, 55%, 50%, 45%, 40%, 35%, 33%, 30%, 25%, 20%, 15%, 10%, 9%, 8%, 7%, 6%, 5%, 4%, 3%, 2%, 1%, 0.5%, or 0.1% the amount of antigen required in the absence of the compound of Formula I.

In some embodiments, the antigen is associated with a bacteria or virus. In some embodiments, the antigen is associated with influenza. In some embodiments, the antigen is associated with SARS-CoV-2 virus. In some embodiments, the antigen is associated with Varicella Zoster.

In some embodiments, the antigen associated with influenza is associated with influenza A. In some embodiments, the antigen associated with influenza is associated with influenza B. In some embodiments, the antigen associated with influenza is associated with influenza C. In some embodiments, the antigen associated with influenza is associated with influenza D. In some embodiments, the antigen associated with influenza is associated with any one of the 18 different hemagglutinin subtypes (H1 through H18). In some embodiments, the antigen associated with influenza is associated with any one of the 11 different neuraminidase subtypes ($N_1$ through $N_{11}$). In some embodiments, the antigen associated with influenza is associated with H3N2. In some embodiments, the antigen associated with influenza is associated with H1N1. In some embodiments, the antigen associated with influenza is associated with B/Phuket. In some embodiments, the antigen associated with influenza is associated with B/Victoria. In some embodiments, the antigen associated with influenza is associated with B/Yamagata. In some embodiments, the antigen associated with influenza is associated with the 6B.1, 3C.2, 3C.3a, V1A, Y1, Y2, or Y3 clades.

In some embodiments, the antigen associated with SARS-CoV-2 is associated with the SARS-CoV-2 spike protein. In some embodiments, the antigen associated with SARS-CoV-2 is associated with the SARS-CoV-2 nucleocapsid protein. In some embodiments, the antigen associated with SARS-CoV-2 is associated with the SARS-CoV-2 envelope protein. In some embodiments, the antigen associated with SARS-CoV-2 is associated with aSARS-CoV-2 non-structural protein, including the papain-like protease, the 3C-like proteinase, NSP1, NSP2, NSP3, NSP4, NSP5, NSP6, NSP7, NSP8, NSP9, NSP10, NSP11, NSP12, NSP13, NSP14, NSP15, and NSP16. In some embodiments, the antigen associated with SARS-CoV-2 is a recombinant SARS-CoV-2 protein, including a recombinant version of any of the foregoing. In some embodiments, the antigen associated with SARS-CoV-2 is an mRNA or DNA version of any of the foregoing. In some embodiments, the antigen associated with SARS-CoV-2 is viral vector incorporating the foregoing. In some embodiments, the antigen associated with SARS-CoV-2 is a live attenuated virus or an inactivated virus. In some embodiments, the vaccine comprises an antigen selected from the group consisting of mRNA-1273, Ad5-nCoV, INO-4800, LV-SMENP-DC, Pathogen-specific aAPC, AZD1222, VPM1002, NVX—CoV2373, and ChAdOx1 nCoV-19.

In some embodiments, vaccines of the present application includes a combination of two different antigens in one vaccine. Preferably, a vaccine of the present application includes a combination of an influenza antigen and a SARS-CoV-2 antigen together with TQL-1055.

Priming

The present application also provides pharmaceutical compositions that demonstrate a substantial priming effect. Such pharmaceutical compositions may include the compounds or compositions of the present application in combination with an antigen. Preferably, the pharmaceutical compositions include TQL-1055:

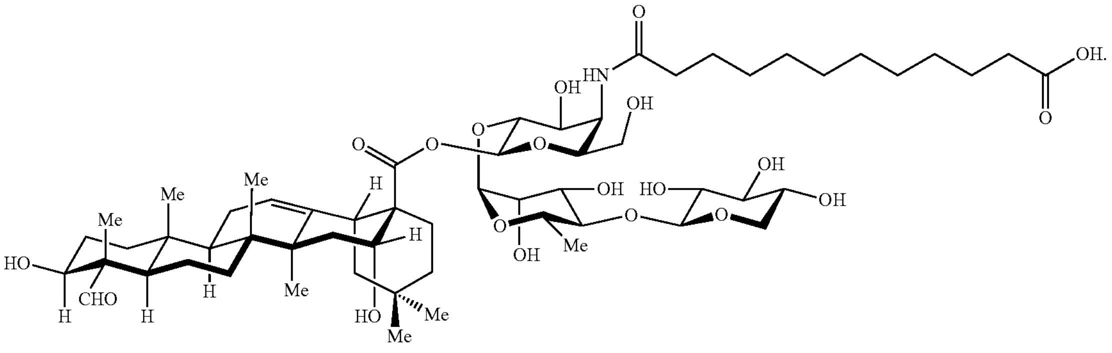

In some embodiments, the amount of antigen provided is less than the amount of antigen required in the absence of the compound of Formula I. In some embodiments, the amount of antigen provided is about 95%, 90%, 85%, 80%, 75%, 70%, 67%, 65%, 60%, 55%, 50%, 45%, 40%, 35%, 33%, 30%, 25%, 20%, 15%, 10%, 9%, 8%, 7%, 6%, 5%, 4%, 3%, 2%, 1%, 0.5%, or 0.1% the amount of antigen required in the absence of the compound of Formula I.

In some embodiments, the antigen is associated with a bacteria or virus. In some embodiments, the antigen is associated with influenza. In some embodiments, the antigen is associated with SARS-CoV-2 virus. In some embodiments, the antigen is associated with Varicella Zoster.

In some embodiments, the antigen associated with influenza is associated with influenza A. In some embodiments, the antigen associated with influenza is associated with influenza B. In some embodiments, the antigen associated with influenza is associated with influenza C. In some embodiments, the antigen associated with influenza is associated with influenza D. In some embodiments, the antigen associated with influenza is associated with any one of the 18 different hemagglutinin subtypes (H1 through H18). In some embodiments, the antigen associated with influenza is associated with any one of the 11 different neuraminidase subtypes ($N_1$ through $N_{11}$). In some embodiments, the antigen associated with influenza is associated with H3N2. In some embodiments, the antigen associated with influenza is associated with H1N1. In some embodiments, the antigen associated with influenza is associated with B/Phuket. In some embodiments, the antigen associated with influenza is associated with B/Victoria. In some embodiments, the antigen associated with influenza is associated with B/Yamagata. In some embodiments, the antigen associated with influenza is associated with the 6B.1, 3C.2, 3C.3a, V1A, Y1, Y2, or Y3 clades.

In some embodiments, the antigen associated with SARS-CoV-2 is associated with the SARS-CoV-2 spike protein. In some embodiments, the antigen associated with SARS-CoV-2 is associated with the SARS-CoV-2 nucleocapsid protein. In some embodiments, the antigen associated with SARS-CoV-2 is associated with the SARS-CoV-2 envelope protein. In some embodiments, the antigen associated with SARS-CoV-2 is associated with aSARS-CoV-2 non-structural protein, including the papain-like protease, the 3C-like proteinase, NSP1, NSP2, NSP3, NSP4, NSP5, NSP6, NSP7, NSP8, NSP9, NSP10, NSP11, NSP12, NSP13, NSP14, NSP15, and NSP16.

In some embodiments, the antigen associated with SARS-CoV-2 is a recombinant SARS-CoV-2 protein, including a recombinant version of any of the foregoing. In some embodiments, the antigen associated with SARS-CoV-2 is an mRNA or DNA version of any of the foregoing. In some embodiments, the antigen associated with SARS-CoV-2 is viral vector incorporating the foregoing. In some embodiments, the antigen associated with SARS-CoV-2 is a live attenuated virus or an inactivated virus. In some embodiments, the vaccine comprises an antigen selected from the group consisting of mRNA-1273, Ad5-nCoV, INO-4800, LV-SMENP-DC, Pathogen-specific aAPC, AZD1222, VPM1002, NVX—CoV2373, and ChAdOx1 nCoV-19.

In some embodiments, vaccines of the present application includes a combination of two different antigens in one vaccine. Preferably, a vaccine of the present application includes a combination of an influenza antigen and a SARS-CoV-2 antigen together with TQL-1055.

Methods

The present application also encompasses methods of conferring immune resistance to an individual. Such methods include administering to an individual a vaccine comprising a therapeutically effective amount of a compound of Formula I, in free form or in pharmaceutically acceptable salt form, together with an antigen or a combination of antigens. In particular, the compound of Formula I may be TQL-1055. In particular, the antigen(s) may be associated with influenza and/or SARS-CoV-2.

The present application also encompasses methods of providing antigen dose sparing effect. Such methods include providing an antigen and a compound of Formula I, wherein the amount of antigen provided is less than the amount of antigen required in the absence of the compound of Formula I.

The present application also encompasses methods of providing vaccine priming effect. Such methods include providing an antigen and a compound of Formula I, wherein the amount of antigen provided is less than the amount of antigen required in the absence of the compound of Formula I to generate the same priming effect.

In particular, the compound of Formula I may be TQL-1055.

The amount of antigen provided may be about 95%, 90%, 85%, 80%, 75%, 70%, 67%, 65%, 60%, 55%, 50%, 45%, 40%, 35%, 33%, 30%, 25%, 20%, 15%, 10%, 9%, 8%, 7%, 6%, 5%, 4%, 3%, 2%, 1%, 0.5%, or 0.1% the amount of antigen required in the absence of the compound of Formula I.

In some embodiments, the antigen is associated with a bacteria or virus. In some embodiments, the antigen is associated with influenza. In some embodiments, the antigen is associated with SARS-CoV-2 virus. In some embodiments, the antigen is associated with Varicella Zoster.

EXAMPLES

Example 1—Evaluation of Priming and Dose-Sparing Effect for Recombinant Influenza Vaccine (H3N2, H1N1, B/Phuket)

Vaccination against both seasonal and pandemic pathogens, e.g. SARS-CoV-2 and influenza, requires effective adjuvants to maximize the utility of limited antigen and to enhance immunogenicity in hyporesponsive at-risk populations. First-generation natural saponins are potent immunoenhancers but are reactogenic and have supply constraints. As part of a NIH-funded project, the novel semisynthetic saponin TQL-1055 was evaluated for its potential to augment the immunogenicity of influenza antigens.

Methods

Groups of 10 C57BL/6J mice were immunized subcutaneously (SC) with FLUBLOK® (H3N2 antigen, HBN antigen, B/Phuket antigen) alone at either a 4.5 mcg or 1.125 mcg dose, or with 30 mcg dose of TQL-1055 choline salt in combination with either a 1.125 mcg, 0.56 mcg, 0.28 mcg, or 0.14 mcg dose of FLUBLOK® on Days 0 and 21. Sera were analyzed at days 0,14, and 28 by ELISA for 1432-specific IgG titers and HI (hemagglutination inhibition) titers, H1N1-specific IgG titers and HI titers, and B/Phuket-specific IgG titers and HI titers. All mice were previously naïve to human influenza.

TABLE 1-1

| Grp | Mice | Antigen | Adjuvant Formulation | Administration Route | Dosing Day | Serology |
|---|---|---|---|---|---|---|
| 1 | 10 | 4.5 mcg FLUBLOK | — | Subcutaneous | D 0, D 14 | D 0, D 14, D 28 |
| 2 | 10 | 1.125 mcg FLUBLOK | — | Subcutaneous | D 0, D 14 | D 0, D 14, D 28 |
| 3 | 10 | 1.125 mcg FLUBLOK | 30 mcg TQL-1055 choline salt | Subcutaneous | D 0, D 14 | D 0, D 14, D 28 |
| 4 | 10 | 0.56 mcg FLUBLOK | 30 mcg TQL-1055 choline salt | Subcutaneous | D 0, D 14 | D 0, D 14, D 28 |
| 5 | 10 | 0.28 mcg FLUBLOK | 30 mcg TQL-1055 choline salt | Subcutaneous | D 0, D 14 | D 0, D 14, D 28 |
| 6 | 10 | 0.14 mcg FLUBLOK | 30 mcg TQL-1055 choline salt | Subcutaneous | D 0, D 14 | D 0, D 14, D 28 |

Results

H3N2

Figure 3:
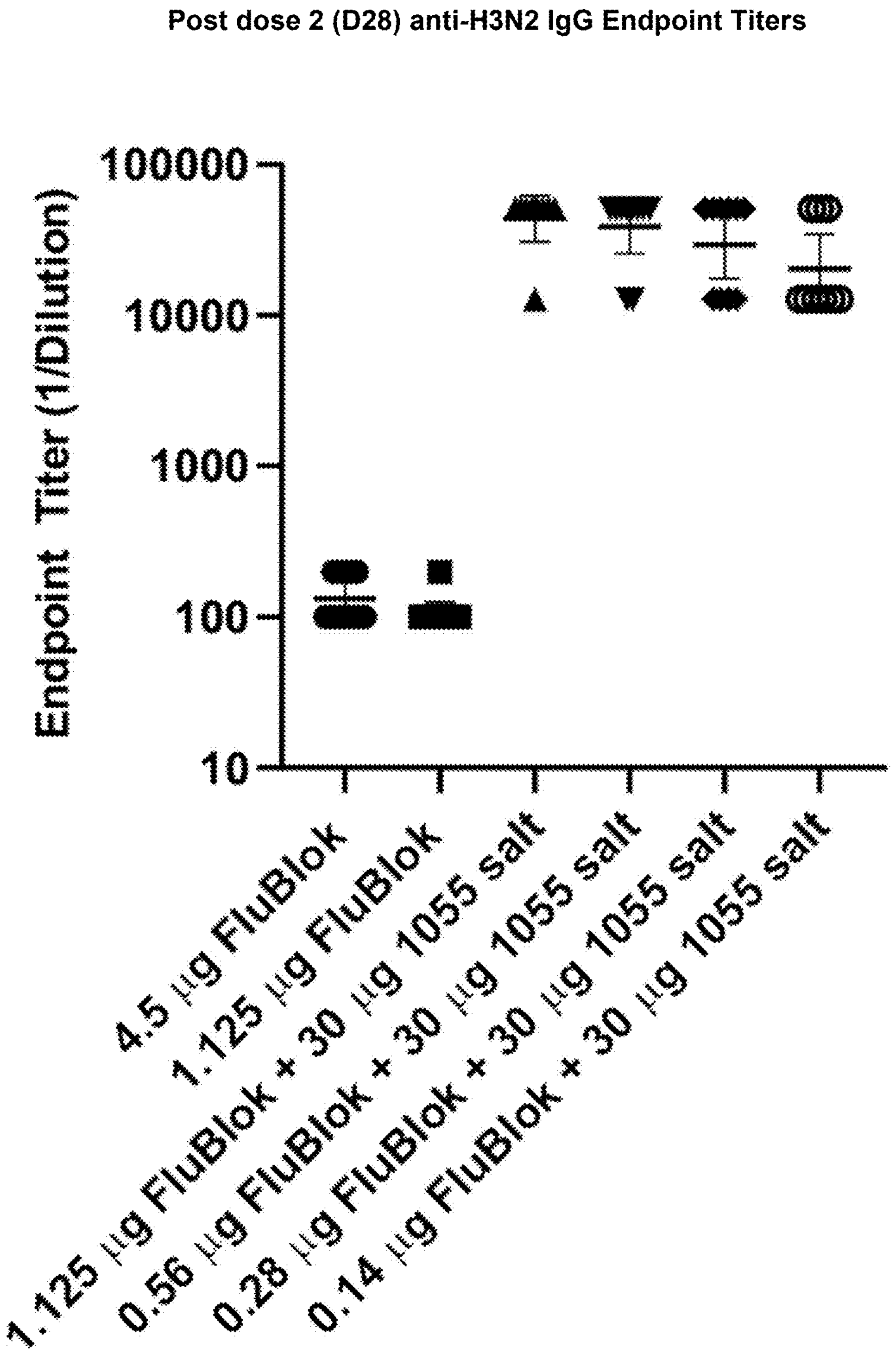
FIG. 3 depicts a chart showing post dose 2 (day 28) anti-H3N2 IgG titers for each group shown in FIG. 1. The data corresponding to this chart are presented in Example 1 of this application.

A 2-dose series of 1.125 mcg, 0.56 mcg, 0.28 mcg, and 0.14 mcg FLUBLOK® in combination with 30 mcg of TQL-1055 choline salt elicited anti-H3N2 antibodies in mice at greater levels than a 2-dose series of 4.5 mcg or 1.125 mcg FLUBLOK® alone. Additionally, a single dose of 1.125 mcg, 0.56 mcg, 0.28 mcg, and 0.14 mcg FLUBLOK® in combination with 30 mcg of TQL-1055 choline salt elicited anti-H3N2 antibodies in mice at greater levels than a 2-dose series of 4.5 mcg or 1.125 mcg FLUBLOK® alone. See FIGS. 2 and 3.

Figure 8:
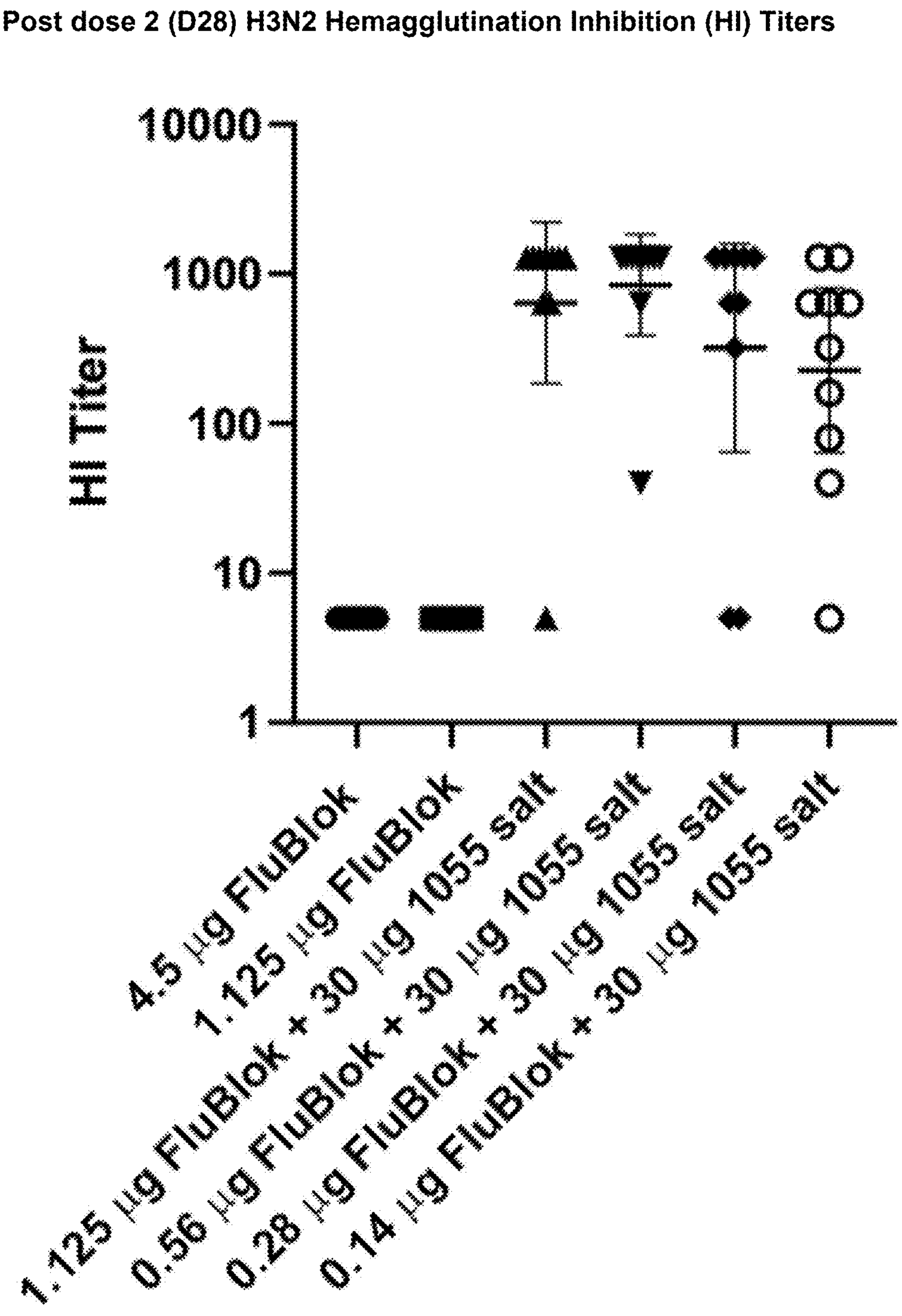
FIG. 8 depicts a chart showing post dose 2 (day 28) H3N2 Hemagglutination Inhibition (HI) titers for each group shown in FIG. 1. The data corresponding to this chart are presented in Example 1 of this application.

A 2-dose series of 1.125 mcg, 0.56 mcg, 0.28 mcg, and 0.14 mcg FLUBLOK® in combination with 30 mcg of TQL-1055 choline salt elicited H3N2 HI titers in mice at equal or greater levels than a 2-dose series of 4.5 mcg or 1.125 mcg FLUBLOK® alone. See FIG. 8.

Figure 11:
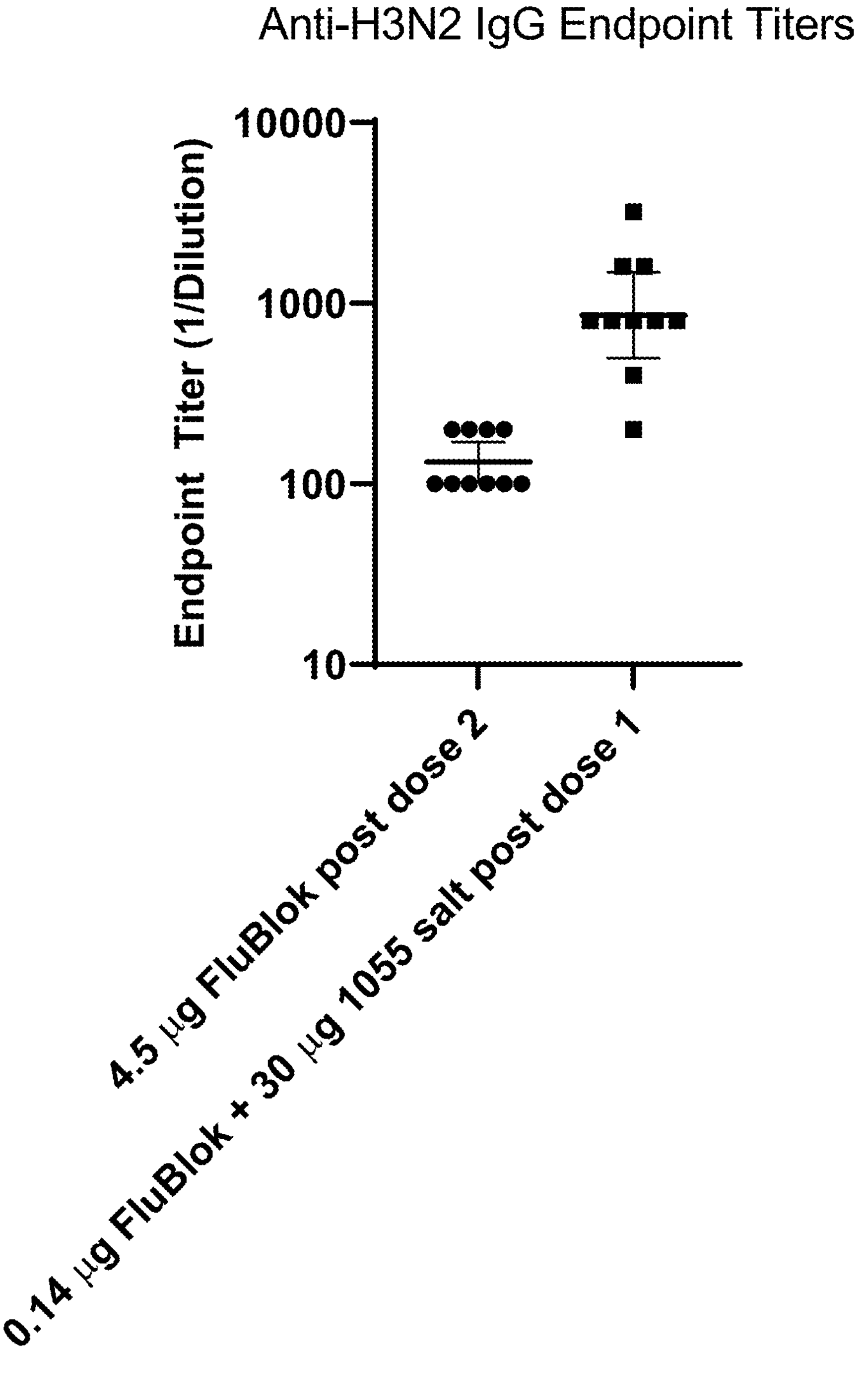
FIG. 11 depicts a chart showing low dose (0.14 mcg) FLUBLOK+30 mcg TQL-1055 choline salt induces significantly higher anti-H3N2 IgG titers after 1 dose compared to high dose (4.5 mcg) FLUBLOK alone after 2 doses. The data corresponding to this chart are presented in Example 1 of this application.

Low dose FLUBLOK (0.14 mcg)+30 mcg 1055 salt induces significantly higher anti-H3N2 IgG titers after 1 dose compared to high dose (4.5 mcg) FLUBLOK alone after 2 doses. See FIG. 11.

Statistical analysis of the post dose 1 (day 14) anti-H3N2 IgG titers demonstrates the following:

TABLE 1-2

| | 4.5 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|
| Geometric Mean | 50 | 1559 | 1740 | 1251 | 1005 |
| Geometric SD factor | 1 | 1.784 | 1.764 | 1.7 | 1.866 |

TABLE 1-3

| Welch's ANOVA with Dunnett's T3 multiple comparisons test | Adjusted P-Value |
|---|---|
| 4.5 mcg FLUBLOK vs. 1.125 mcg FLUBLOK | >0.9999 |
| 4.5 mcg FLUBLOK vs. 1.125 mcg FLUBLOK + 30 mcg TQL-1055 choline salt | <0.0001 |
| 4.5 mcg FLUBLOK vs. 0.56 mcg FLUBLOK + 30 mcg TQL-1055 choline salt | <0.0001 |
| 4.5 mcg FLUBLOK vs. 0.28 mcg FLUBLOK + 30 mcg TQL-1055 choline salt | <0.0001 |
| 4.5 mcg FLUBLOK vs. 0.14 mcg FLUBLOK + 30 mcg TQL-1055 choline salt | 0.0001 |
| 1.125 mcg FLUBLOK vs. 1.125 mcg FLUBLOK + 30 mcg TQL-1055 choline salt | <0.0001 |
| 1.125 mcg FLUBLOK vs. 0.56 mcg FLUBLOK + 30 mcg TQL-1055 choline salt | <0.0001 |
| 1.125 mcg FLUBLOK vs. 0.28 mcg FLUBLOK + 30 mcg TQL-1055 choline salt | <0.0001 |
| 1.125 mcg FLUBLOK vs. 0.14 mcg FLUBLOK + 30 mcg TQL-1055 choline salt | 0.0001 |
| 1.125 mcg FLUBLOK + 30 mcg TQL-1055 choline salt vs. 0.56 mcg FLUBLOK + 30 mcg TQL-1055 choline salt | 0.9532 |
| 1.125 mcg FLUBLOK + 30 mcg TQL-1055 choline salt vs. 0.28 mcg FLUBLOK + 30 mcg TQL-1055 choline salt | 0.978 |
| 1.125 mcg FLUBLOK + 30 mcg TQL-1055 choline salt vs. 0.14 mcg FLUBLOK + 30 mcg TQL-1055 choline salt | 0.2285 |
| 0.56 mcg FLUBLOK + 30 mcg TQL-1055 choline salt vs. 0.28 mcg FLUBLOK + 30 mcg TQL-1055 choline salt | >0.9999 |
| 0.56 mcg FLUBLOK + 30 mcg TQL-1055 choline salt vs. 0.14 mcg FLUBLOK + 30 mcg TQL-1055 choline salt | 0.7098 |
| 0.28 mcg FLUBLOK + 30 mcg TQL-1055 choline salt vs. 0.14 mcg FLUBLOK + 30 mcg TQL-1055 choline salt | 0.78 |

Statistical analysis of the post dose 2 (day 28) anti-H3N2 IgG titers demonstrates the following:

TABLE 1-4

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 10 | 10 | 9 | 10 | 10 | 9 |
| Geometric Mean | 132.0 | 107.2 | 43891 | 38802 | 29407 | 20319 |
| Geometric SD factor | 1.430 | 1.245 | 1.587 | 1.794 | 2.046 | 2.000 |
| Lower 95% CI of geo. mean | 102.1 | 91.62 | 30769 | 25543 | 17621 | 11926 |
| Upper 95% CI of geo. mean | 170.5 | 125.4 | 62609 | 58946 | 49074 | 34617 |

TABLE 1-5

| Welch's ANOVA with Dunnett's T3 multiple comparisons test | Adjusted P-Value |
|---|---|
| 4.5 mcg FLUBLOK vs. 1.125 mcg FLUBLOK | 0.8188 |
| 4.5 mcg FLUBLOK vs. 1.125 mcg FLUBLOK + 30 mcg TQL-1055 choline salt | <0.0001 |
| 4.5 mcg FLUBLOK vs. 0.56 mcg FLUBLOK + 30 mcg TQL-1055 choline salt | <0.0001 |
| 4.5 mcg FLUBLOK vs. 0.28 mcg FLUBLOK + 30 mcg TQL-1055 choline salt | <0.0001 |
| 4.5 mcg FLUBLOK vs. 0.14 mcg FLUBLOK + 30 mcg TQL-1055 choline salt | <0.0001 |
| 1.125 mcg FLUBLOK vs. 1.125 mcg FLUBLOK + 30 mcg TQL-1055 choline salt | <0.0001 |
| 1.125 mcg FLUBLOK vs. 0.56 mcg FLUBLOK + 30 mcg TQL-1055 choline salt | <0.0001 |
| 1.125 mcg FLUBLOK vs. 0.28 mcg FLUBLOK + 30 mcg TQL-1055 choline salt | <0.0001 |
| 1.125 mcg FLUBLOK vs. 0.14 mcg FLUBLOK + 30 mcg TQL-1055 choline salt | <0.0001 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | 0.8741 |
| 1.125 mcg FLUBLOK + 30 mcg TQL-1055 choline salt vs. 0.14 mcg FLUBLOK + 30 mcg TQL-1055 choline salt | 0.1692 |
| 0.56 mcg FLUBLOK + 30 mcg TQL-1055 choline salt vs. 0.28 mcg FLUBLOK + 30 mcg TQL-1055 choline salt | 0.9951 |
| 0.56 mcg FLUBLOK + 30 mcg TQL-1055 choline salt vs. 0.14 mcg FLUBLOK + 30 mcg TQL-1055 choline salt | 0.4187 |
| 0.28 mcg FLUBLOK + 30 mcg TQL-1055 choline salt vs. 0.14 mcg FLUBLOK + 30 mcg TQL-1055 choline salt | 0.976 |
| 4.5 mcg FLUBLOK post dose 2 vs 0.14 mcg FLUBLOK + 30 mcg TQL-1055 choline salt post dose 1 | <0.0001 |

Statistical analysis of the post dose 2 (day 28) H3N2 Hemagglutination Inhibition (HI) titers demonstrates the following:

TABLE 1-6

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 9 | 9 | 10 | 10 | 10 | 10 |
| Geometric Mean | 5.000 | 5.000 | 640.0 | 844.5 | 320.0 | 226.3 |
| Geometric SD factor | 1.000 | 1.000 | 5.653 | 2.985 | 9.394 | 5.854 |
| Lower 95% CI of geo. mean | 5.000 | 5.000 | 185.8 | 386.2 | 64.45 | 63.92 |
| Upper 95% CI of geo. mean | 5.000 | 5.000 | 2205 | 1846 | 1589 | 801.0 |

TABLE 1-7

| Welch's ANOVA with Dunnett's T3 multiple comparisons test | Adjusted P-Value |
|---|---|
| 4.5 mcg FLUBLOK vs. 1.125 mcg FLUBLOK | >0.9999 |
| 4.5 mcg FLUBLOK vs. 1.125 mcg FLUBLOK + 30 mcg TQL-1055 choline salt | 0.0008 |
| 4.5 mcg FLUBLOK vs. 0.56 mcg FLUBLOK + 30 mcg TQL-1055 choline salt | 0.0003 |
| 4.5 mcg FLUBLOK vs. 0.28 mcg FLUBLOK + 30 mcg TQL-1055 choline salt | 0.0203 |
| 4.5 mcg FLUBLOK vs. 0.14 mcg FLUBLOK + 30 mcg TQL-1055 choline salt | 0.1198 |
| 1.125 mcg FLUBLOK vs. 1.125 mcg FLUBLOK + 30 mcg TQL-1055 choline salt | 0.0008 |
| 1.125 mcg FLUBLOK vs. 0.56 mcg FLUBLOK + 30 mcg TQL-1055 choline salt | 0.0003 |
| 1.125 mcg FLUBLOK vs. 0.28 mcg FLUBLOK + 30 mcg TQL-1055 choline salt | 0.0203 |
| 1.125 mcg FLUBLOK vs. 0.14 mcg FLUBLOK + 30 mcg TQL-1055 choline salt | 0.1198 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | 0.9982 |
| 1.125 mcg FLUBLOK + 30 mcg TQL-1055 choline salt vs. 0.14 mcg FLUBLOK + 30 mcg TQL-1055 choline salt | 0.3175 |
| 0.56 mcg FLUBLOK + 30 mcg TQL-1055 choline salt vs. 0.28 mcg FLUBLOK + 30 mcg TQL-1055 choline salt | 0.9673 |
| 0.56 mcg FLUBLOK + 30 mcg TQL-1055 choline salt vs. 0.14 mcg FLUBLOK + 30 mcg TQL-1055 choline salt | 0.1556 |
| 0.28 mcg FLUBLOK + 30 mcg TQL-1055 choline salt vs. 0.14 mcg FLUBLOK + 30 mcg TQL-1055 choline salt | 0.9787 |

H1N1

Figure 4:
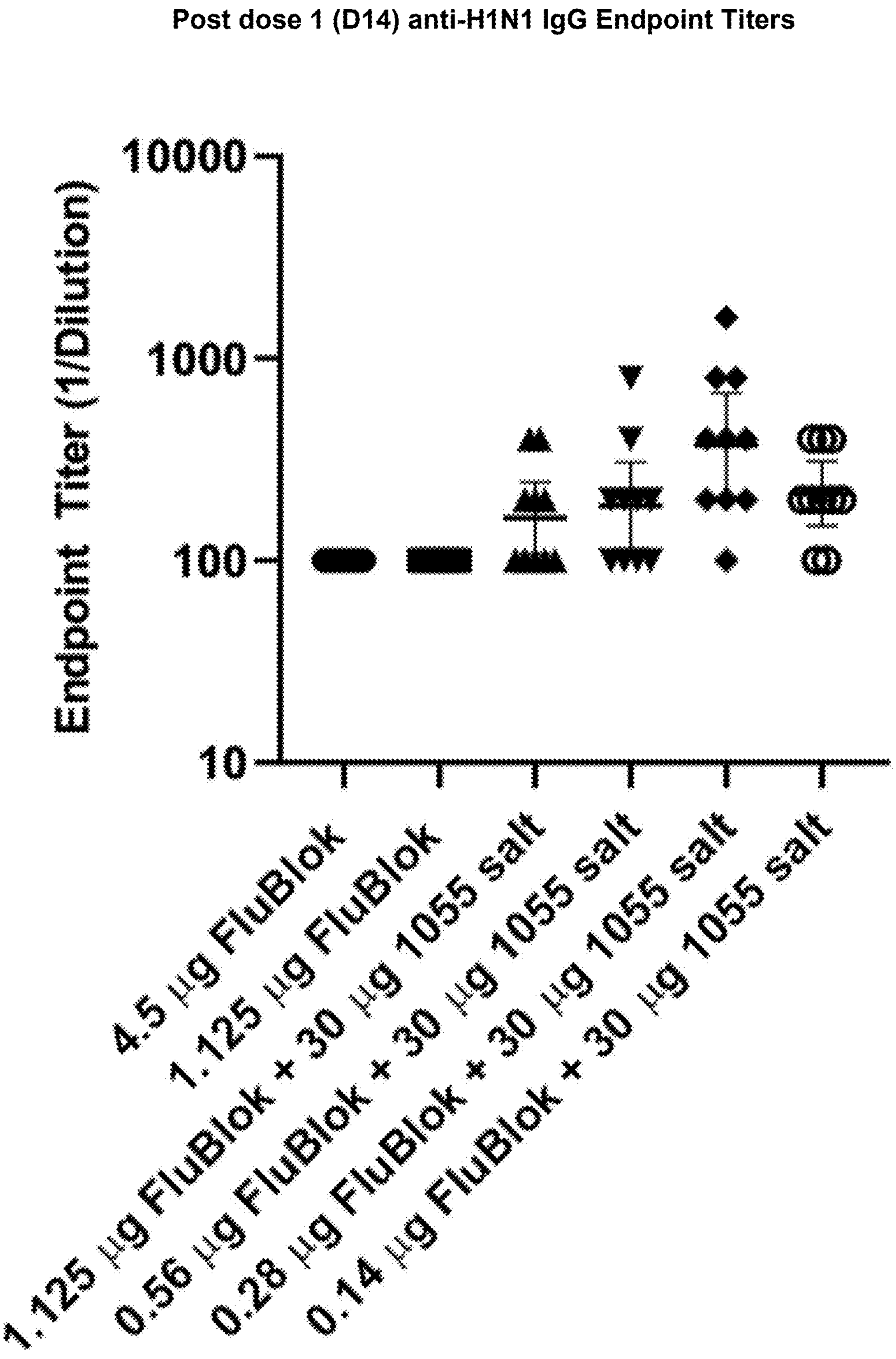
FIG. 4 depicts a chart showing post dose 1 (day 14) anti-H1N1 IgG titers for each group shown in FIG. 1. The data corresponding to this chart are presented in Example 1 of this application.
Figure 5:
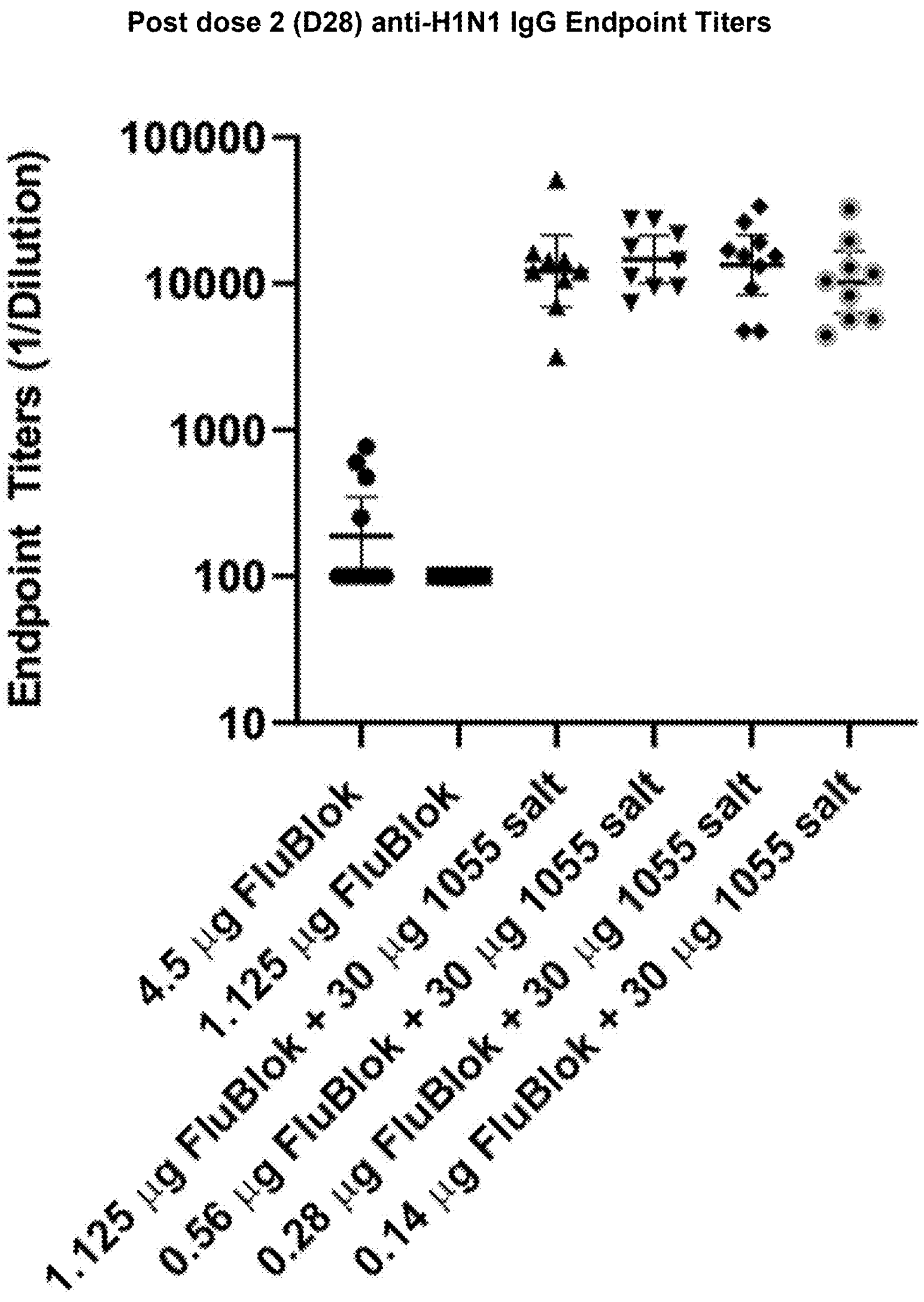
FIG. 5 depicts a chart showing post dose 2 (day 28) anti-H1N1 IgG titers for each group shown in FIG. 1. The data corresponding to this chart are presented in Example 1 of this application.

A 2-dose series of 1.125 mcg, 0.56 mcg, 0.28 mcg, and 0.14 mcg FLUBLOK® in combination with 30 mcg of TQL-1055 choline salt elicited anti-H1N1 antibodies in all mice at greater levels than a 2-dose series of 4.5 mcg or 1.125 mcg FLUBLOK® alone. Additionally, a single dose of 1.125 mcg, 0.56 mcg, 0.28 mcg, and 0.14 mcg FLUBLOK® in combination with 30 mcg of TQL-1055 choline salt elicited anti-H1N1 antibodies in all mice at equal or greater levels than a 2-dose series of 4.5 mcg or 1.125 mcg FLUBLOK® alone. FIGS. 4 and 5.

Figure 9:
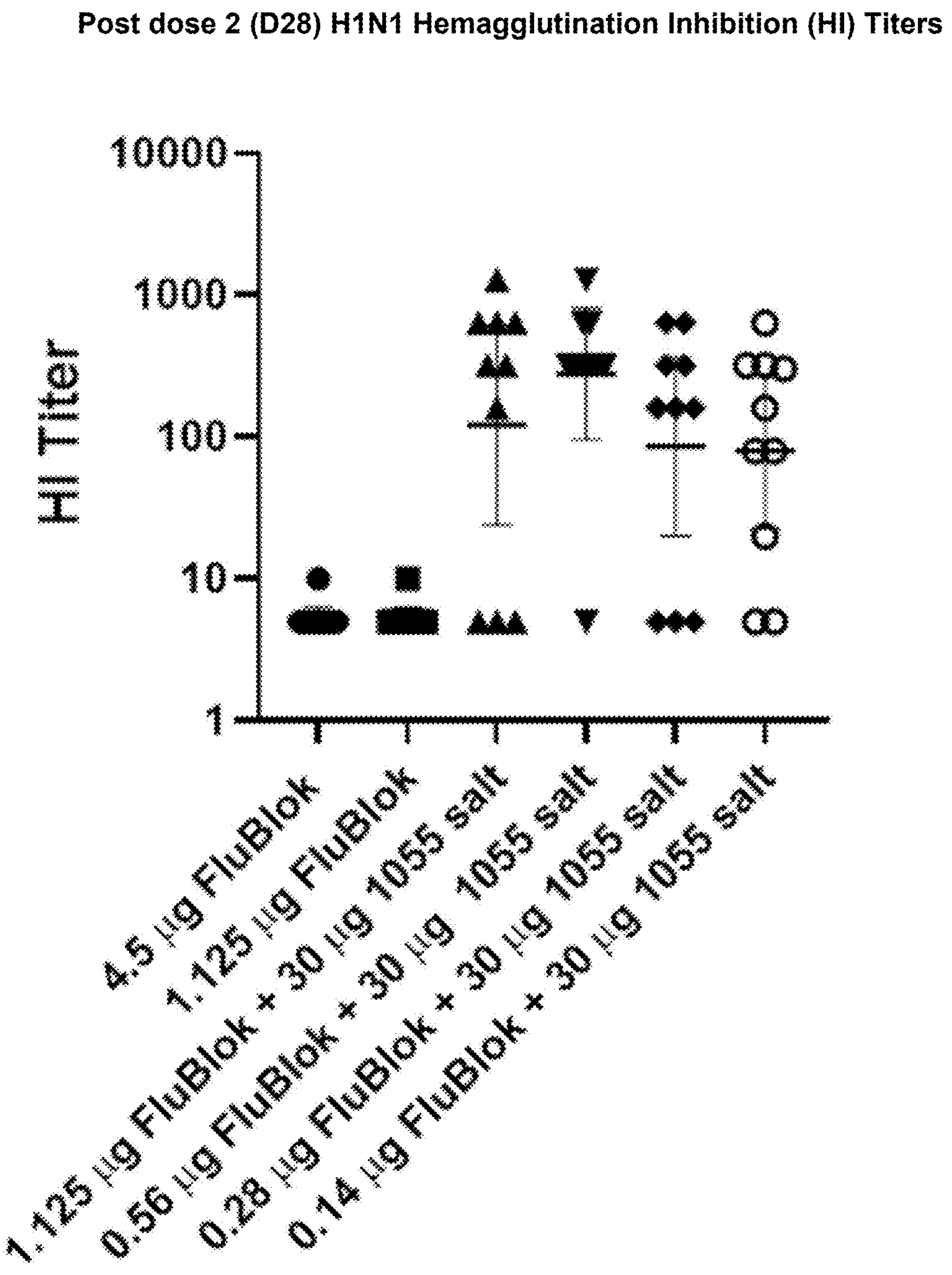
FIG. 9 depicts a chart showing post dose 2 (day 28) H1N1 Hemagglutination Inhibition (HI) titers for each group shown in FIG. 1. The data corresponding to this chart are presented in Example 1 of this application.

A 2-dose series of 1.125 mcg, 0.56 mcg, 0.28 mcg, and 0.14 mcg FLUBLOK® in combination with 30 mcg of TQL-1055 choline salt elicited H1N1 HI titers in all mice at equal or greater levels than a 2-dose series of 4.5 mcg or 1.125 mcg FLUBLOK alone. See FIG. 9.

Figure 12:
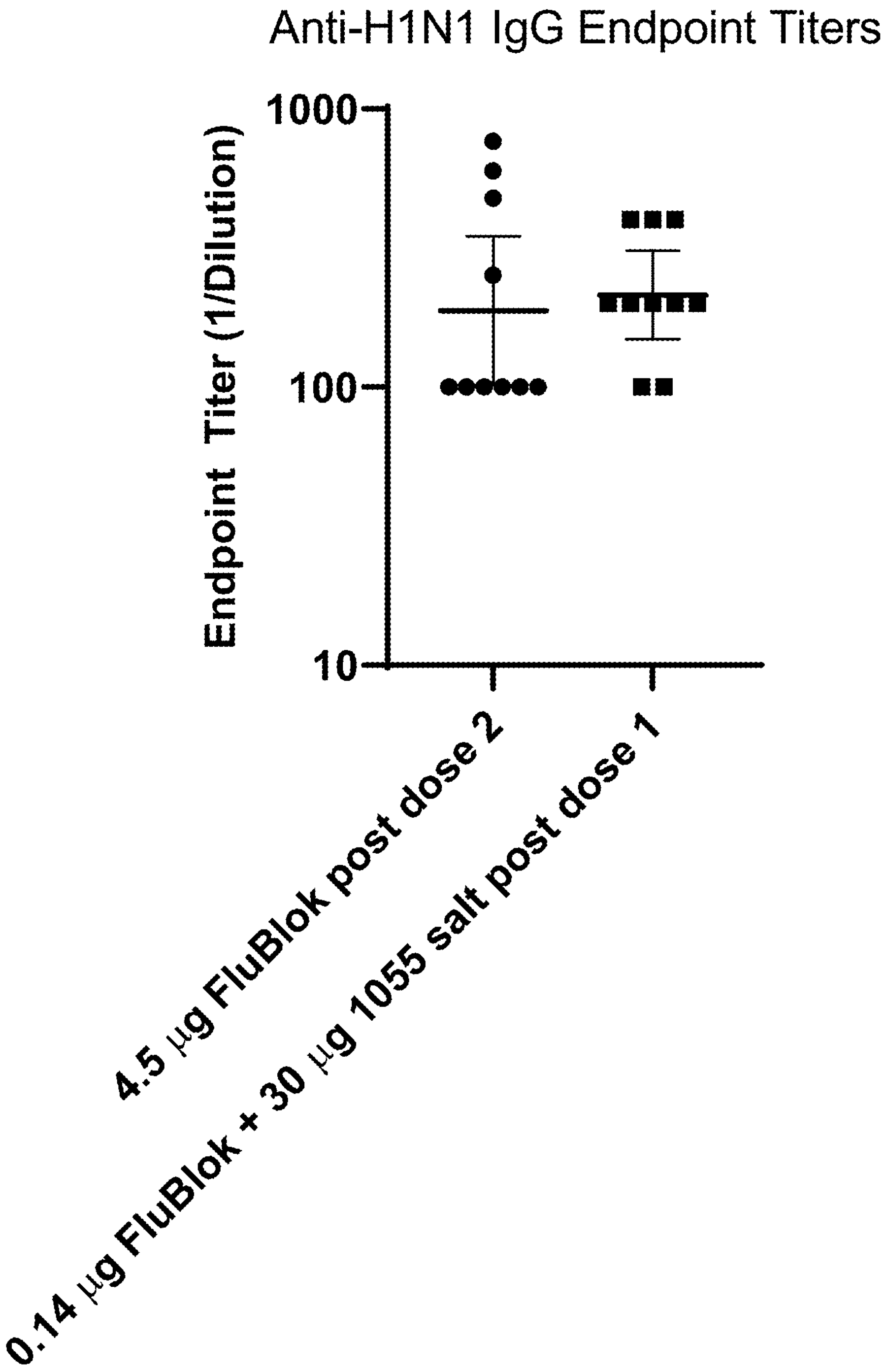
FIG. 12 depicts a chart showing low dose (0.14 mcg) FLUBLOK+30 mcg TQL-1055 choline salt induces similar anti-H1N1 IgG titers after 1 dose compared to high dose (4.5 mcg) FLUBLOK alone after 2 doses. The data corresponding to this chart are presented in Example 1 of this application.

Low dose FLUBLOK (0.14 mcg)+30 mcg TQL-1055 choline salt induces similar anti-H1N1 IgG titers after 1 dose compared to high dose (4.5 mcg) FLUBLOK alone after 2 doses. See FIG. 12.

Statistical analysis of the post dose 1 (day 14) ani-H1N1 IgG titers demonstrates the following:

TABLE 1-8

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 10 | 10 | 10 | 10 | 10 | 10 |
| Geometric Mean | 100.0 | 100.0 | 162.5 | 186.6 | 373.2 | 214.4 |
| Geometric SD factor | 1.000 | 1.000 | 1.769 | 1.992 | 2.293 | 1.668 |
| Lower 95% CI of geo. mean | 100.0 | 100.0 | 108.0 | 114.0 | 206.1 | 148.7 |
| Upper 95% CI of geo. mean | 100.0 | 100.0 | 244.3 | 305.5 | 675.7 | 309.0 |

TABLE 1-9

| Welch's ANOVA with Dunnett's T3 multiple comparisons test | Adjusted P-Value |
|---|---|
| 4.5 mcg FLUBLOK vs. 1.125 mcg FLUBLOK | >0.9999 |
| 4.5 mcg FLUBLOK vs. 1.125 mcg FLUBLOK + 30 mcg TQL-1055 choline salt | 0.219 |
| 4.5 mcg FLUBLOK vs. 0.56 mcg FLUBLOK + 30 mcg TQL-1055 choline salt | 0.1739 |
| 4.5 mcg FLUBLOK vs. 0.28 mcg FLUBLOK + 30 mcg TQL-1055 choline salt | 0.0084 |
| 4.5 mcg FLUBLOK vs. 0.14 mcg FLUBLOK + 30 mcg TQL-1055 choline salt | 0.0123 |
| 1.125 mcg FLUBLOK vs. 1.125 mcg FLUBLOK + 30 mcg TQL-1055 choline salt | 0.219 |
| 1.125 mcg FLUBLOK vs. 0.56 mcg FLUBLOK + 30 mcg TQL-1055 choline salt | 0.1739 |
| 1.125 mcg FLUBLOK vs. 0.28 mcg FLUBLOK + 30 mcg TQL-1055 choline salt | 0.0084 |
| 1.125 mcg FLUBLOK vs. 0.14 mcg FLUBLOK + 30 mcg TQL-1055 choline salt | 0.0123 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | 0.2123 |
| 1.125 mcg FLUBLOK + 30 mcg TQL-1055 choline salt vs. 0.14 mcg FLUBLOK + 30 mcg TQL-1055 choline salt | 0.9764 |
| 0.56 mcg FLUBLOK + 30 mcg TQL-1055 choline salt vs. 0.28 mcg FLUBLOK + 30 mcg TQL-1055 choline salt | 0.5145 |
| 0.56 mcg FLUBLOK + 30 mcg TQL-1055 choline salt vs. 0.14 mcg FLUBLOK + 30 mcg TQL-1055 choline salt | >0.9999 |
| 0.28 mcg FLUBLOK + 30 mcg TQL-1055 choline salt vs. 0.14 mcg FLUBLOK + 30 mcg TQL-1055 choline salt | 0.6739 |

Statistical analysis of the post dose 2 (day 38) anti-H1N1IgG titers demonstrates the following:

TABLE 1-10

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 10 | 10 | 9 | 9 | 10 | 9 |
| Geometric Mean | 188.2 | 99.90 | 12172 | 14678 | 13427 | 10224 |
| Geometric SD factor | 2.366 | 1.003 | 2.084 | 1.626 | 1.918 | 1.889 |
| Lower 95% CI of geo. mean | 101.6 | 99.67 | 6923 | 10100 | 8428 | 6271 |
| Upper 95% CI of geo. mean | 384.4 | 100.1 | 21401 | 21330 | 21393 | 16668 |

TABLE 1-11

| Welch's ANOVA with Dunnett's T3 multiple comparisons test | Adjusted P-Value |
|---|---|
| 4.5 mcg FLUBLOK vs. 1.125 mcg FLUBLOK | 0.4812 |
| 4.5 mcg FLUBLOK vs. 1.125 mcg FLUBLOK + 30 mcg TQL-1055 choline salt | 0.1066 |
| 4.5 mcg FLUBLOK vs. 0.56 mcg FLUBLOK + 30 mcg TQL-1055 choline salt | 0.0032 |
| 4.5 mcg FLUBLOK vs. 0.28 mcg FLUBLOK + 30 mcg TQL-1055 choline salt | 0.0050 |
| 4.5 mcg FLUBLOK vs. 0.14 mcg FLUBLOK + 30 mcg TQL-1055 choline salt | 0.0382 |
| 1.125 mcg FLUBLOK vs. 1.125 mcg FLUBLOK + 30 mcg TQL-1055 choline salt | 0.1014 |
| 1.125 mcg FLUBLOK vs. 0.56 mcg FLUBLOK + 30 mcg TQL-1055 choline salt | 0.0029 |
| 1.125 mcg FLUBLOK vs. 0.28 mcg FLUBLOK + 30 mcg TQL-1055 choline salt | 0.0046 |
| 1.125 mcg FLUBLOK vs. 0.14 mcg FLUBLOK + 30 mcg TQL-1055 choline salt | 0.0353 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | >0.9999 |
| 1.125 mcg FLUBLOK + 30 mcg TQL-1055 choline salt vs. 0.14 mcg FLUBLOK + 30 mcg TQL-1055 choline salt | >0.9999 |
| 0.56 mcg FLUBLOK + 30 mcg TQL-1055 choline salt vs. 0.28 mcg FLUBLOK + 30 mcg TQL-1055 choline salt | >0.9999 |
| 0.56 mcg FLUBLOK + 30 mcg TQL-1055 choline salt vs. 0.14 mcg FLUBLOK + 30 mcg TQL-1055 choline salt | 0.9921 |
| 0.28 mcg FLUBLOK + 30 mcg TQL-1055 choline salt vs. 0.14 mcg FLUBLOK + 30 mcg TQL-1055 choline salt | 0.9981 |
| 4.5 mcg FLUBLOK post dose 2 vs 0.14 mcg FLUBLOK + 30 mcg TQL-1055 choline salt post dose 1 | 0.7404 |

Statistical analysis of the post dose 2 (day 28) H1N1 Hemagglutination Inhibition (HI) titers demonstrates the following:

TABLE 1-12

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 10 | 10 | 10 | 10 | 10 | 10 |
| Geometric Mean | 5.359 | 5.359 | 121.3 | 278.6 | 85.74 | 79.54 |
| Geometric SD factor | 1.245 | 1.245 | 9.665 | 4.438 | 7.585 | 5.781 |
| Lower 95% CI of geo. mean | 4.581 | 4.581 | 23.93 | 95.93 | 20.12 | 22.67 |
| Upper 95% CI of geo. mean | 6.269 | 6.269 | 614.4 | 808.9 | 365.3 | 279.1 |

TABLE 1-13

| Welch's ANOVA with Dunnett's T3 multiple comparisons test | Adjusted P-Value |
|---|---|
| 4.5 mcg FLUBLOK vs. 1.125 mcg FLUBLOK | >0.9999 |
| 4.5 mcg FLUBLOK vs. 1.125 mcg FLUBLOK + 30 mcg TQL-1055 choline salt | 0.1701 |
| 4.5 mcg FLUBLOK vs. 0.56 mcg FLUBLOK + 30 mcg TQL-1055 choline salt | 0.0415 |
| 4.5 mcg FLUBLOK vs. 0.28 mcg FLUBLOK + 30 mcg TQL-1055 choline salt | 0.1632 |
| 4.5 mcg FLUBLOK vs. 0.14 mcg FLUBLOK + 30 mcg TQL-1055 choline salt | 0.2188 |
| 1.125 mcg FLUBLOK vs. 1.125 mcg FLUBLOK + 30 mcg TQL-1055 choline salt | 0.1701 |
| 1.125 mcg FLUBLOK vs. 0.56 mcg FLUBLOK + 30 mcg TQL-1055 choline salt | 0.0415 |
| 1.125 mcg FLUBLOK vs. 0.28 mcg FLUBLOK + 30 mcg TQL-1055 choline salt | 0.1632 |
| 1.125 mcg FLUBLOK vs. 0.14 mcg FLUBLOK + 30 mcg TQL-1055 choline salt | 0.2188 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | 0.9954 |
| 1.125 mcg FLUBLOK + 30 mcg TQL-1055 choline salt vs. 0.14 mcg FLUBLOK + 30 mcg TQL-1055 choline salt | 0.9298 |
| 0.56 mcg FLUBLOK + 30 mcg TQL-1055 choline salt vs. 0.28 mcg FLUBLOK + 30 mcg TQL-1055 choline salt | 0.8924 |
| 0.56 mcg FLUBLOK + 30 mcg TQL-1055 choline salt vs. 0.14 mcg FLUBLOK + 30 mcg TQL-1055 choline salt | 0.6169 |
| 0.28 mcg FLUBLOK + 30 mcg TQL-1055 choline salt vs. 0.14 mcg FLUBLOK + 30 mcg TQL-1055 choline salt | >0.9999 |

B/Phuket

Figure 6:
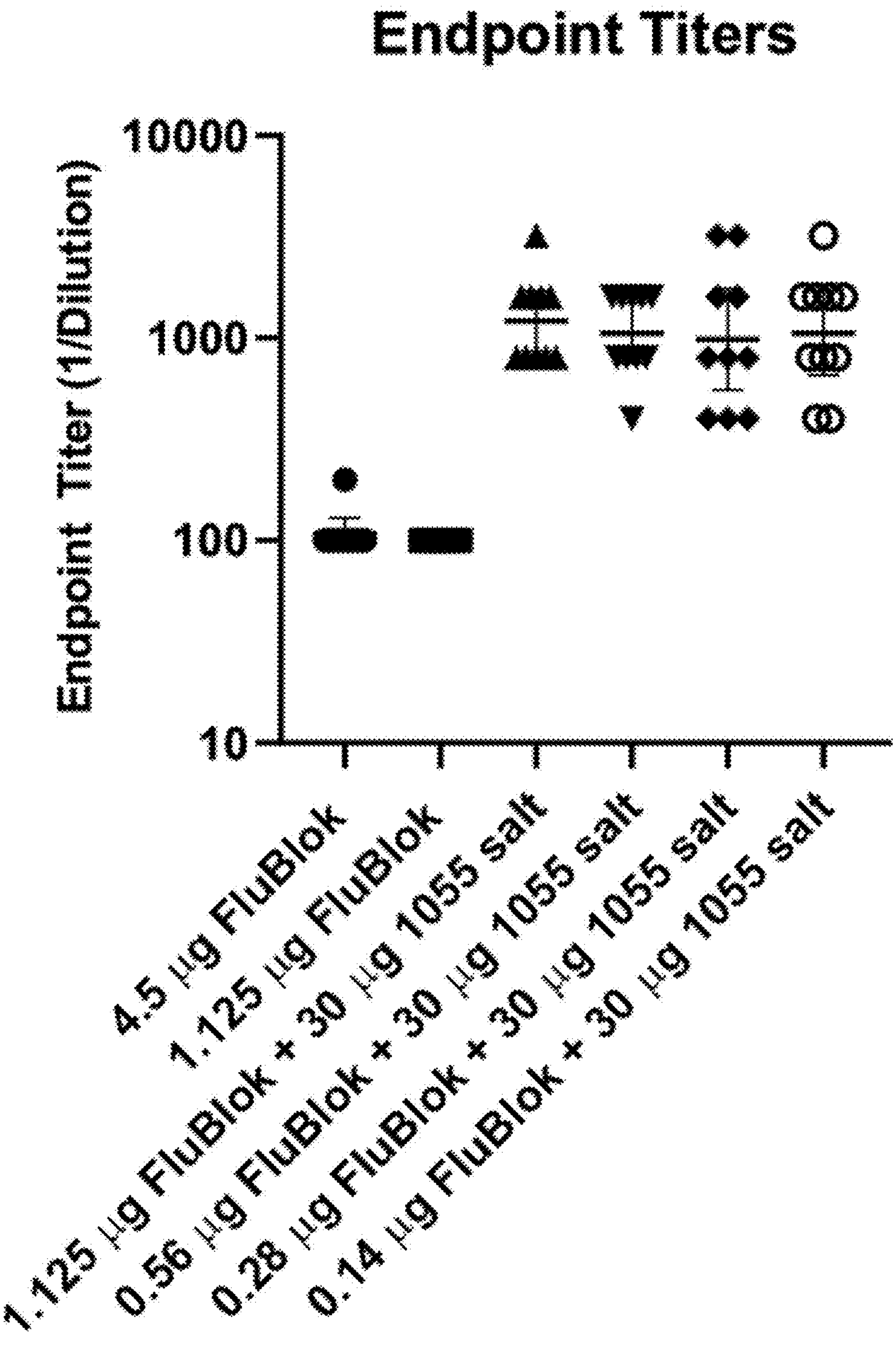
FIG. 6 depicts a chart showing post dose 1 (day 14) anti-B/Phuket IgG titers for each group shown in FIG. 1. The data corresponding to this chart are presented in Example 1 of this application.
Figure 7:
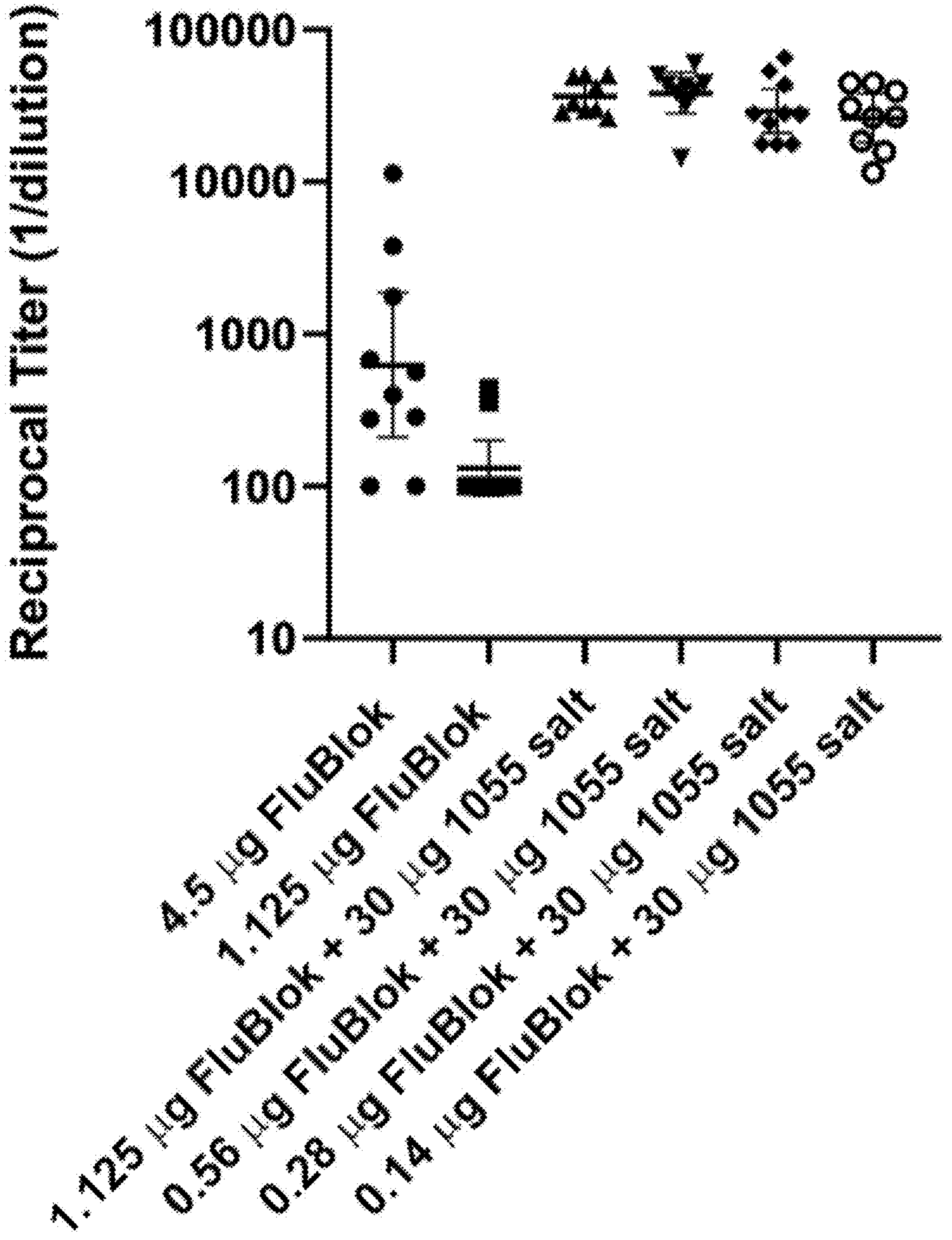
FIG. 7 depicts a chart showing post dose 2 (day 28) anti-B/Phuket IgG titers for each group shown in FIG. 1. The data corresponding to this chart are presented in Example 1 of this application.

A 2-dose series of 1.125 mcg, 0.56 mcg, 0.28 mcg, and 0.14 mcg FLUBLOK® in combination with 30 mcg of TQL-1055 choline salt elicited anti-B/Phuket antibodies in all mice at greater levels than a 2-dose series of 4.5 mcg or 1.125 mcg FLUBLOK® alone. Additionally, a single dose of 1.125 mcg, 0.56 mcg, 0.28 mcg, and 0.14 mcg FLUBLOK® in combination with 30 mcg of TQL-1055 choline salt elicited anti-B/Phuket antibodies in all mice on average at equal or greater levels than a 2-dose series of 4.5 mcg or 1.125 mcg FLUBLOK® alone. See FIGS. 6 and 7.

Figure 10:
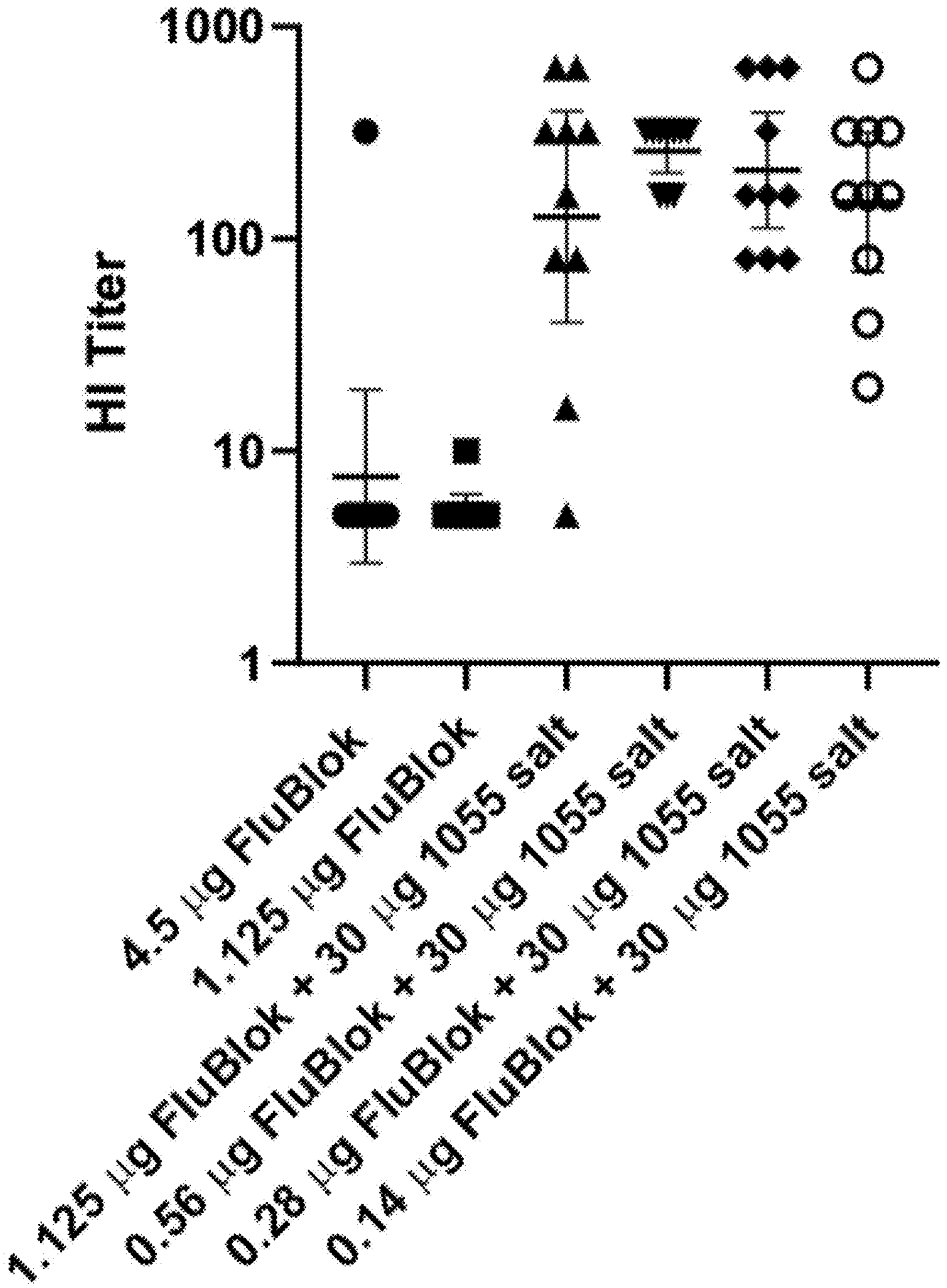
FIG. 10 depicts a chart showing post dose 2 (day 28) anti-B/Phuket Hemagglutination Inhibition (HI) titers for each group shown in FIG. 1. The data corresponding to this chart are presented in Example 1 of this application.

A 2-dose series of 1.125 mcg, 0.56 mcg, 0.28 mcg, and 0.14 mcg FLUBLOK® in combination with 30 mcg of TQL-1055 choline salt elicited B/Phuket HI titers in all mice at equal or greater levels than a 2-dose series of 4.5 mcg or 1.125 mcg FLUBLOK® alone. See FIG. 10.

Figure 13:
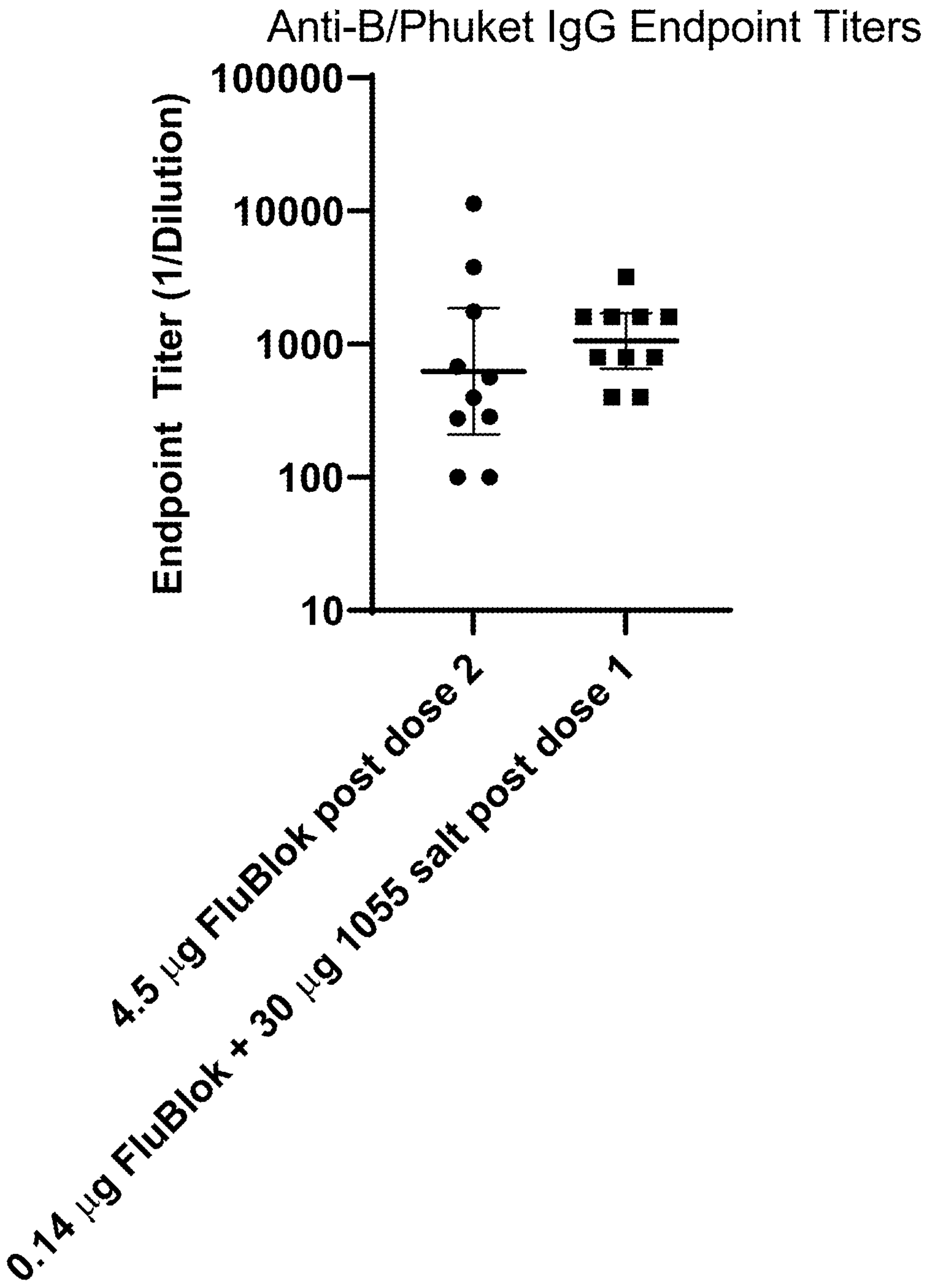
FIG. 13 depicts a chart showing low dose (0.14 mcg) FLUBLOK+30 mcg TQL-1055 choline salt induces similar anti-B/Phuket IgG titers after 1 dose compared to high dose (4.5 mcg) FLUBLOK alone after 2 doses. The data corresponding to this chart are presented in Example 1 of this application.

Low dose (0.14 mcg) FLUBLOK+30 mcg TQL-1055 choline salt induces similar anti-B/Phuket IgG titers after 1 dose compared to high dose (4.5 mcg) FLUBLOK alone after 2 doses. See FIG. 13.

Statistical analysis of the post dose 1 (day 14) anti-B/Phuket IgG titers demonstrates the following:

TABLE 1-14

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 9 | 9 | 10 | 10 | 10 | 10 |

TABLE 1-14-continued

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Geometric Mean | 108.0 | 100.0 | 1213 | 1056 | 984.9 | 1056 |
| Geometric SD factor | 1.260 | 1.000 | 1.624 | 1.624 | 2.234 | 1.954 |
| Lower 95% CI of geo. mean | 90.43 | 100.0 | 857.3 | 746.3 | 554.3 | 653.8 |
| Upper 95% CI of geo. mean | 129.0 | 100.0 | 1715 | 1493 | 1750 | 1704 |

TABLE 1-15

| Welch's ANOVA with Dunnett's T3 multiple comparisons test | Adjusted P-Value |
|---|---|
| 4.5 mcg FLUBLOK vs. 1.125 mcg FLUBLOK | 0.9908 |
| 4.5 mcg FLUBLOK vs. 1.125 mcg FLUBLOK + 30 mcg TQL-1055 choline salt | <0.0001 |
| 4.5 mcg FLUBLOK vs. 0.56 mcg FLUBLOK + 30 mcg TQL-1055 choline salt | <0.0001 |
| 4.5 mcg FLUBLOK vs. 0.28 mcg FLUBLOK + 30 mcg TQL-1055 choline salt | <0.0001 |
| 4.5 mcg FLUBLOK vs. 0.14 mcg FLUBLOK + 30 mcg TQL-1055 choline salt | <0.0001 |
| 1.125 mcg FLUBLOK vs. 1.125 mcg FLUBLOK + 30 mcg TQL-1055 choline salt | <0.0001 |
| 1.125 mcg FLUBLOK vs. 0.56 mcg FLUBLOK + 30 mcg TQL-1055 choline salt | <0.0001 |
| 1.125 mcg FLUBLOK vs. 0.28 mcg FLUBLOK + 30 mcg TQL-1055 choline salt | 0.0001 |
| 1.125 mcg FLUBLOK vs. 0.14 mcg FLUBLOK + 30 mcg TQL-1055 choline salt | <0.0001 |

TABLE 1-15-continued

| Welch's ANOVA with Dunnett's T3 multiple comparisons test | Adjusted P-Value |
|---|---|
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | 0.9998 |
| 1.125 mcg FLUBLOK + 30 mcg TQL-1055 choline salt vs. 0.14 mcg FLUBLOK + 30 mcg TQL-1055 choline salt | >0.9999 |
| 0.56 mcg FLUBLOK + 30 mcg TQL-1055 choline salt vs. 0.28 mcg FLUBLOK + 30 mcg TQL-1055 choline salt | >0.9999 |
| 0.56 mcg FLUBLOK + 30 mcg TQL-1055 choline salt vs. 0.14 mcg FLUBLOK + 30 mcg TQL-1055 choline salt | >0.9999 |
| 0.28 mcg FLUBLOK + 30 mcg TQL-1055 choline salt vs. 0.14 mcg FLUBLOK + 30 mcg TQL-1055 choline salt | >0.9999 |

Statistical analysis of the post dose 2 (day 38) anti-B/Phuket IgG titers demonstrates the following:

TABLE 1-16

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 10 | 10 | 9 | 9 | 10 | 9 |
| Geometric Mean | 625.6 | 131.8 | 36494 | 38247 | 29174 | 26180 |
| Geometric SD factor | 4.599 | 1.794 | 1.305 | 1.499 | 1.595 | 1.610 |
| Lower 95% CI of geo. mean | 210.0 | 86.77 | 29742 | 28014 | 20894 | 18151 |
| Upper 95% CI of geo. mean | 1863 | 200.2 | 44780 | 52218 | 40735 | 37760 |

TABLE 1-17

| Welch's ANOVA with Dunnett's T3 multiple comparisons test | Adjusted P-Value |
|---|---|
| 4.5 mcg FLUBLOK vs. 1.125 mcg FLUBLOK | 0.7899 |
| 4.5 mcg FLUBLOK vs. 1.125 mcg FLUBLOK + 30 mcg TQL-1055 choline salt | <0.0001 |
| 4.5 mcg FLUBLOK vs. 0.56 mcg FLUBLOK + 30 mcg TQL-1055 choline salt | 0.0001 |
| 4.5 mcg FLUBLOK vs. 0.28 mcg FLUBLOK + 30 mcg TQL-1055 choline salt | 0.0024 |
| 4.5 mcg FLUBLOK vs. 0.14 mcg FLUBLOK + 30 mcg TQL-1055 choline salt | 0.0017 |
| 1.125 mcg FLUBLOK vs. 1.125 mcg FLUBLOK + 30 mcg TQL-1055 choline salt | <0.0001 |
| 1.125 mcg FLUBLOK vs. 0.56 mcg FLUBLOK + 30 mcg TQL-1055 choline salt | 0.0001 |
| 1.125 mcg FLUBLOK vs. 0.28 mcg FLUBLOK + 30 mcg TQL-1055 choline salt | 0.0019 |
| 1.125 mcg FLUBLOK vs. 0.14 mcg FLUBLOK + 30 mcg TQL-1055 choline salt | 0.0014 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | 0.9978 |
| 1.125 mcg FLUBLOK + 30 mcg TQL-1055 choline salt vs. 0.14 mcg FLUBLOK + 30 mcg TQL-1055 choline salt | 0.7448 |
| 0.56 mcg FLUBLOK + 30 mcg TQL-1055 choline salt vs. 0.28 mcg FLUBLOK + 30 mcg TQL-1055 choline salt | 0.9556 |
| 0.56 mcg FLUBLOK + 30 mcg TQL-1055 choline salt vs. 0.14 mcg FLUBLOK + 30 mcg TQL-1055 choline salt | 0.5195 |
| 0.28 mcg FLUBLOK + 30 mcg TQL-1055 choline salt vs. 0.14 mcg FLUBLOK + 30 mcg TQL-1055 choline salt | >0.9999 |
| 4.5 mcg FLUBLOK post dose 2 vs 0.14 mcg FLUBLOK + 30 mcg TQL-1055 choline salt post dose 1 | 0.3398 |

Statistical analysis of the post dose 2 (day 28) anti-B/Phuket IgG titers demonstrates the following:

TABLE 1-18

| | 4.5 mcg FLUBLOK | 1.125 mcg FLUBLOK | 1.125 mcg FLUBLOK + 30 mcg TQL-1055 Choline Salt | 0.56 mcg FLUBLOK + 30 mcg TQL-1055 Choline Salt | 0.28 mcg FLUBLOK + 30 mcg TQL-1055 Choline Salt | 0.14 mcg FLUBLOK + 30 mcg TQL-1055 Choline Salt |
|---|---|---|---|---|---|---|
| Number of Values | 10 | 10 | 10 | 10 | 10 | 10 |
| Geometric Mean | 7.579 | 5.359 | 127.1 | 259.9 | 211.1 | 149.3 |
| Geometric SD factor | 3.725 | 1.245 | 4.951 | 1.398 | 2.403 | 2.876 |
| Lower 95% CI of geo. mean | −34.76 | 4.369 | 89.67 | 216.7 | 119.0 | 89.42 |
| Upper 95% CI of geo. mean | 107.8 | 6.631 | 426.5 | 327.3 | 473.0 | 354.6 |

TABLE 1-19

| Welch's ANOVA with Dunnett's T3 multiple comparisons test | Adjusted P-Value |
|---|---|
| 4.5 mcg FLUBLOK vs. 1.125 mcg FLUBLOK | 0.9966 |
| 4.5 mcg FLUBLOK vs. 1.125 mcg FLUBLOK + 30 mcg TQL-1055 choline salt | 0.2417 |
| 4.5 mcg FLUBLOK vs. 0.56 mcg FLUBLOK + 30 mcg TQL-1055 choline salt | 0.0003 |

TABLE 1-19-continued

| Welch's ANOVA with Dunnett's T3 multiple comparisons test | Adjusted P-Value |
|---|---|
| 4.5 mcg FLUBLOK vs. 0.28 mcg FLUBLOK + 30 mcg TQL-1055 choline salt | 0.1422 |
| 4.5 mcg FLUBLOK vs. 0.14 mcg FLUBLOK + 30 mcg TQL-1055 choline salt | 0.211 |
| 1.125 mcg FLUBLOK vs. 1.125 mcg FLUBLOK + 30 mcg TQL-1055 choline salt | 0.11 |
| 1.125 mcg FLUBLOK vs. 0.56 mcg FLUBLOK + 30 mcg TQL-1055 choline salt | <0.0001 |
| 1.125 mcg FLUBLOK vs. 0.28 mcg FLUBLOK + 30 mcg TQL-1055 choline salt | 0.0699 |
| 1.125 mcg FLUBLOK vs. 0.14 mcg FLUBLOK + 30 mcg TQL-1055 choline salt | 0.0717 |
| 1.125 mcg FLUBLOK + 30 mcg TQL-1055 choline salt vs. 0.56 mcg FLUBLOK + 30 mcg TQL-1055 choline salt | >0.9999 |
| 1.125 mcg FLUBLOK + 30 mcg TQL-1055 choline salt vs. 0.28 mcg FLUBLOK + 30 mcg TQL-1055 choline salt | >0.9999 |
| 1.125 mcg FLUBLOK + 30 mcg TQL-1055 choline salt vs. 0.14 mcg FLUBLOK + 30 mcg TQL-1055 choline salt | >0.9999 |
| 0.56 mcg FLUBLOK + 30 mcg TQL-1055 choline salt vs. 0.28 mcg FLUBLOK + 30 mcg TQL-1055 choline salt | >0.9999 |
| 0.56 mcg FLUBLOK + 30 mcg TQL-1055 choline salt vs. 0.14 mcg FLUBLOK + 30 mcg TQL-1055 choline salt | 0.9998 |
| 0.28 mcg FLUBLOK + 30 mcg TQL-1055 choline salt vs. 0.14 mcg FLUBLOK + 30 mcg TQL-1055 choline salt | >0.9999 |

Discussion:

As shown in the foregoing results and in FIGS. 1 through 13, TQL-1055 exhibits robust adjuvant activity for influenza antigens, demonstrating significant priming and dose-sparing effect. As noted above, all mice studied were previously naïve to human influenza strains. Thus, the results demonstrate TQL-1055 produces these effects even when the subject's immune system is challenged with a novel pathogen, as is the case when exposed to pandemic pathogens. The results thus suggest TQL-1055 would be particularly useful as an adjuvant in vaccines against novel pathogens, including human pandemic pathogens. Priming in particular is critical for pandemic applications, such as COVID-19, whereas dose-sparing is important for both pandemic and non-pandemic applications (e.g. COVID-19 and influenza).

Example 2—Evaluating Antibody Response of TQL-1055 Choline Salt (C.S.) and TQL-1055 Free Acid (F.A.) with SARS-CoV-2 Receptor Binding Domain (RBD)

Methods

Mice were vaccinated subcutaneously (S.C.) or intramuscularly (I.M.) with 1 mcg SARS-CoV-2 receptor binding domain (RBD) antigen. In addition to the antigen, mice received TQL-1055 C.S. or TQL-1055 F.A. at various doses (10 mcg, 30 mcg, 100 mcg). Control groups with antigen alone and antigen with 10 mcg QS-21 were used. Thirteen days after Dose 1, sera was collected and analyzed for total anti-RBD IgG. On D14, a second dose identical to the first dose was administered. Twenty-eight days after Dose 1, sera was collected and analyzed for total anti-RBD IgG.

Results

IgG Endpoint Titer Data—Subcutaneous Injection—Post Dose 1

Figure 14:
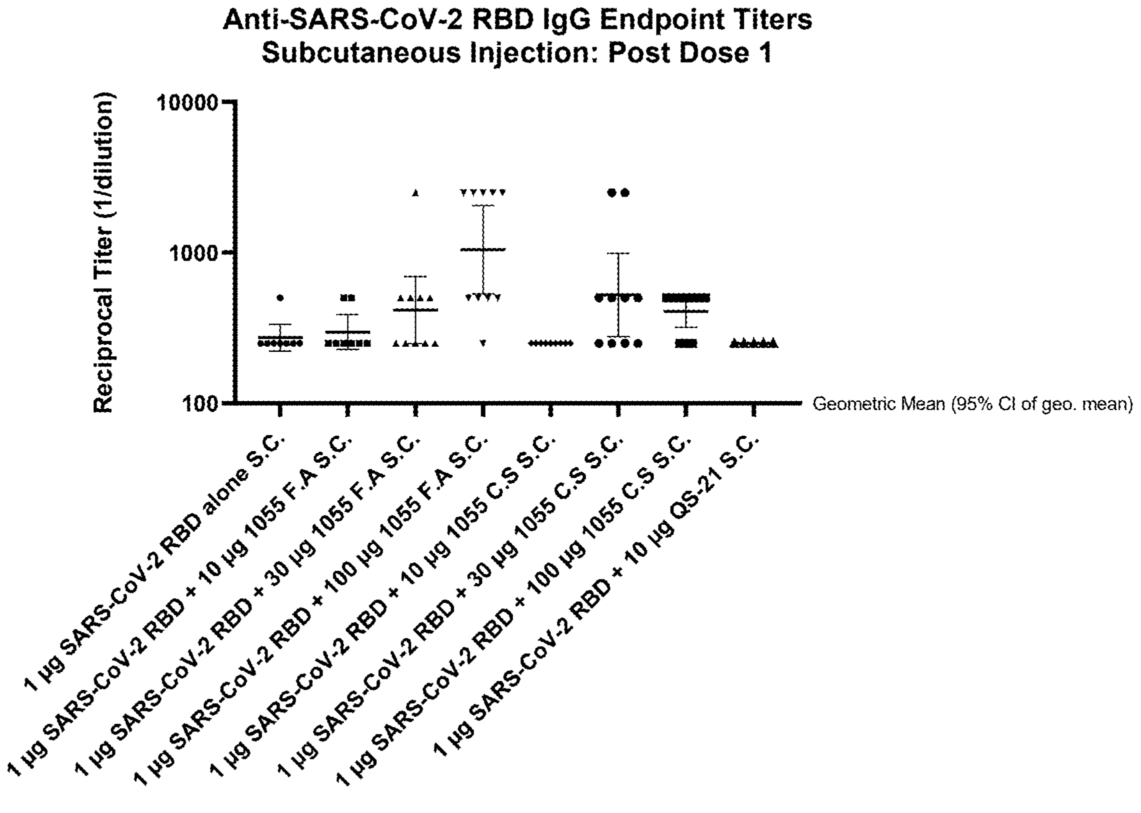
FIG. 14 depicts a chart showing anti-SARS-CoV-2 Receptor Binding Domain (RBD) IgG endpoint titers for groups of mice vaccinated with SARS-CoV-2 antigen and TQL-1055. The data corresponding to this chart are presented in Example 2 of this application.

The IgG endpoint titer data for subcutaneous injection post dose 1 is depicted in FIG. 14 and shown in the table below.

TABLE 2-1

| | 1 μg SARS-CoV-2 RBD alone S.C. | 1 μg SARS-CoV-2 RBD + 10 μg 1055 F.A S.C. | 1 μg SARS-CoV-2 RBD + 30 μg 1055 F.A S.C. | 1 μg SARS-CoV-2 RBD + 100 μg 1055 F.A S.C. | 1 μg SARS-CoV-2 RBD + 10 μg 1055 C.S S.C. | 1 μg SARS-CoV-2 RBD + 30 μg 1055 C.S S.C. | 1 μg SARS-CoV-2 RBD + 100 μg 1055 C.S S.C. | 1 μg SARS-CoV-2 RBD + 10 μg QS-21 S.C. |
|---|---|---|---|---|---|---|---|---|
| Number of values | 8 | 8 | 10 | 10 | 9 | 10 | 10 | 6 |
| Geometric mean | 272.6 | 297.3 | 415.3 | 1043 | 250.0 | 522.8 | 406.1 | 250.0 |
| Geometric SD factor | 1.278 | 1.378 | 2.052 | 2.571 | 1.000 | 2.428 | 1.398 | 1.000 |
| Lower 95% CI of geo. mean | 222.1 | 227.4 | 248.4 | 530.9 | 250.0 | 277.2 | 319.6 | 250.0 |
| Upper 95% CI of geo. mean | 334.6 | 388.8 | 694.4 | 2050 | 250.0 | 986.2 | 516.0 | 250.0 |

IgG Endpoint Titer Data—Intramuscular Injection—Post Dose 1

Figure 15:
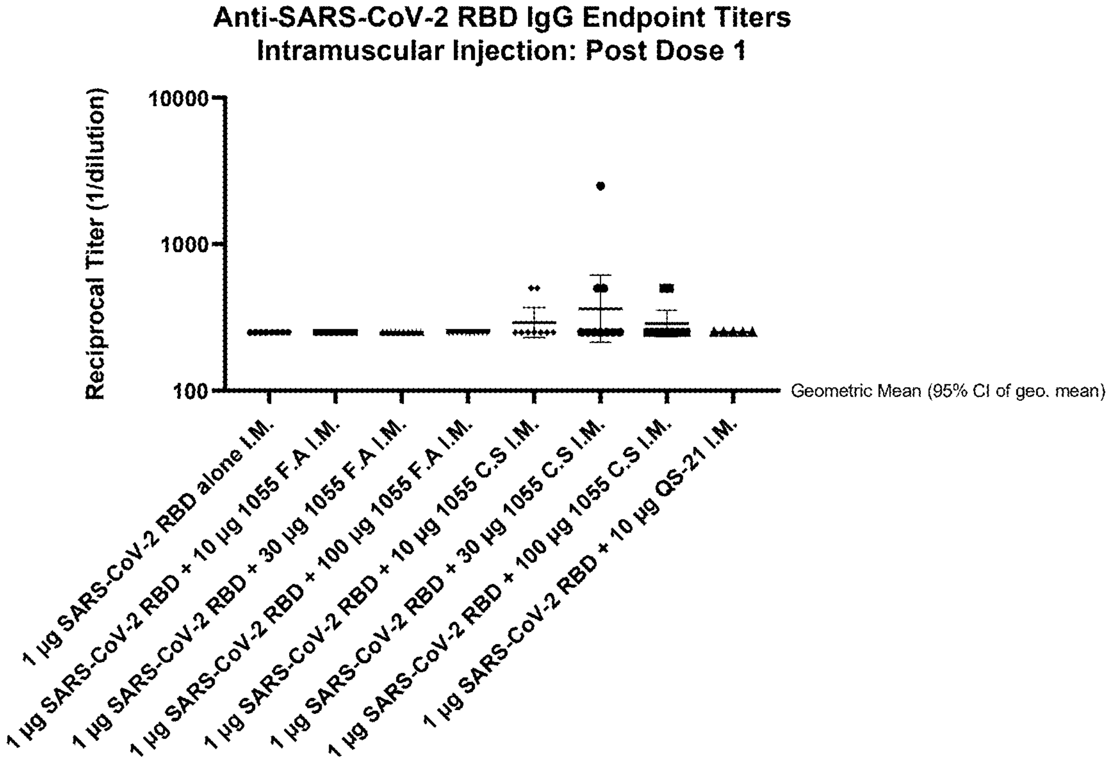
FIG. 15 depicts a chart showing anti-SARS-CoV-2 Receptor Binding Domain (RBD) IgG endpoint titers for groups of mice vaccinated with SARS-CoV-2 antigen and TQL-1055. The data corresponding to this chart are presented in Example 2 of this application.

The IgG endpoint titer data for intramuscular injection post dose 1 is depicted in FIG. 15 and shown in the table below.

TABLE 2-2

| | 1 μg SARS-CoV-2 RBD alone I.M. | 1 μg SARS-CoV-2 RBD + 10 μg 1055 F.A I.M. | 1 μg SARS-CoV-2 RBD + 30 μg 1055 F.A I.M. | 1 μg SARS-CoV-2 RBD + 100 μg 1055 F.A I.M. | 1 μg SARS-CoV-2 RBD + 10 μg 1055 C.S I.M. | 1 μg SARS-CoV-2 RBD + 30 μg 1055 C.S I.M. | 1 μg SARS-CoV-2 RBD + 100 μg 1055 C.S I.M. | 1 μg SARS-CoV-2 RBD + 10 μg QS-21 I.M. |
|---|---|---|---|---|---|---|---|---|
| Number of values | 8 | 8 | 10 | 10 | 9 | 10 | 10 | 5 |
| Geometric mean | 250.0 | 250.0 | 250.0 | 250.0 | 291.6 | 361.5 | 287.2 | 250.0 |
| Geometric SD factor | 1.000 | 1.000 | 1.000 | 1.000 | 1.358 | 2.092 | 1.339 | 1.000 |
| Lower 95% CI of geo. mean | 250.0 | 250.0 | 250.0 | 250.0 | 230.6 | 213.2 | 233.0 | 250.0 |
| Upper 95% CI of geo. mean | 250.0 | 250.0 | 250.0 | 250.0 | 368.9 | 613.0 | 354.0 | 250.0 |

IgG Endpoint Titer Data—Subcutaneous Injection—Post Dose 2

Figure 16:
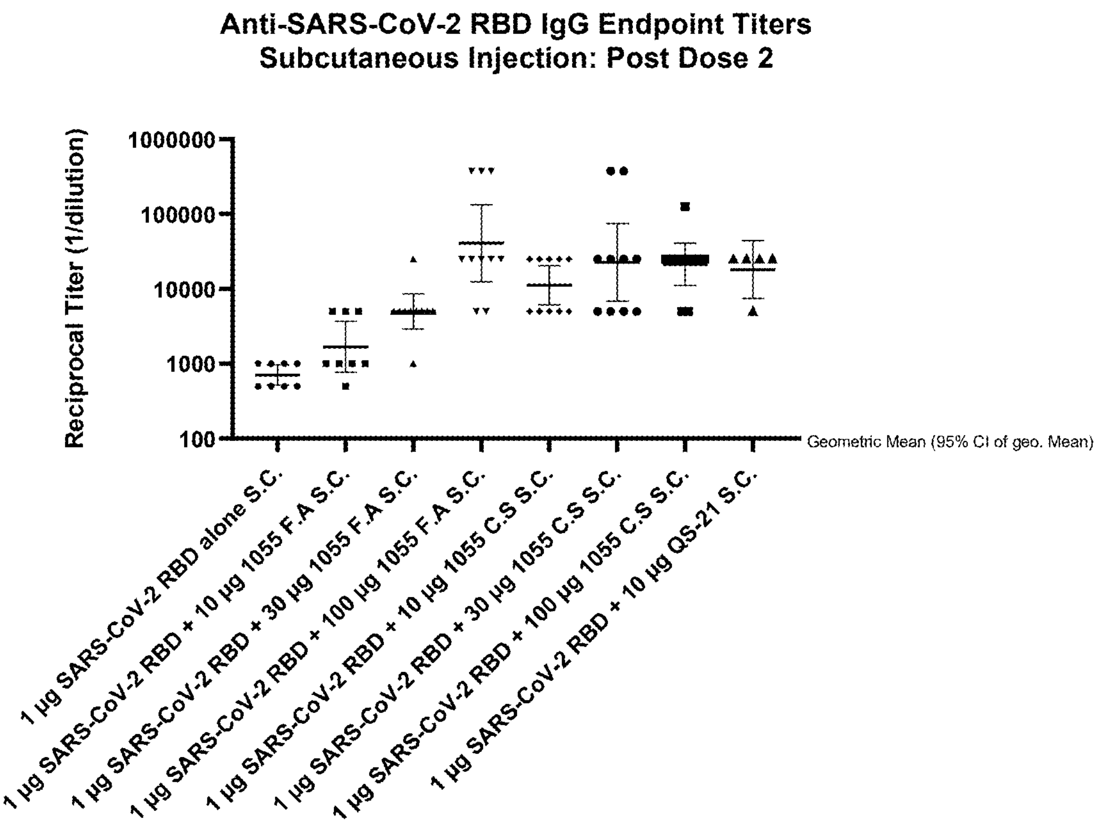
FIG. 16 depicts a chart showing anti-SARS-CoV-2 Receptor Binding Domain (RBD) IgG endpoint titers for groups of mice vaccinated with SARS-CoV-2 antigen and TQL-1055. The data corresponding to this chart are presented in Example 2 of this application.

The IgG endpoint titer data for subcutaneous injection post dose 2 is depicted in FIG. 16 and shown in the table below.

TABLE 2-3

| | 1 μg SARS-CoV-2 RBD alone S.C. | 1 μg SARS-CoV-2 RBD + 10 μg 1055 F.A S.C. | 1 μg SARS-CoV-2 RBD + 30 μg 1055 F.A S.C. | 1 μg SARS-CoV-2 RBD + 100 μg 1055 F.A S.C. | 1 μg SARS-CoV-2 RBD + 10 μg 1055 C.S S.C. | 1 μg SARS-CoV-2 RBD + 30 μg 1055 C.S S.C. | 1 μg SARS-CoV-2 RBD + 100 μg 1055 C.S S.C. | 1 μg SARS-CoV-2 RBD + 10 μg QS-21 S.C. |
|---|---|---|---|---|---|---|---|---|
| Number of values | 8 | 8 | 10 | 10 | 9 | 10 | 10 | 5 |
| Geometric mean | 707.1 | 1677 | 5000 | 40829 | 12226 | 22572 | 21283 | 18119 |
| Geometric SD factor | 1.448 | 2.546 | 2.135 | 5.255 | 2.336 | 5.281 | 2.493 | 2.054 |
| Lower 95% CI of geo. mean | 518.8 | 767.7 | 2906 | 12460 | 6370 | 6864 | 11072 | 7413 |
| Upper 95% CI of geo. mean | 963.8 | 3663 | 8604 | 133792 | 23467 | 74229 | 40914 | 44287 |

IgG Endpoint Titer Data—Intramuscular Injection—Post Dose 2

Figure 17:
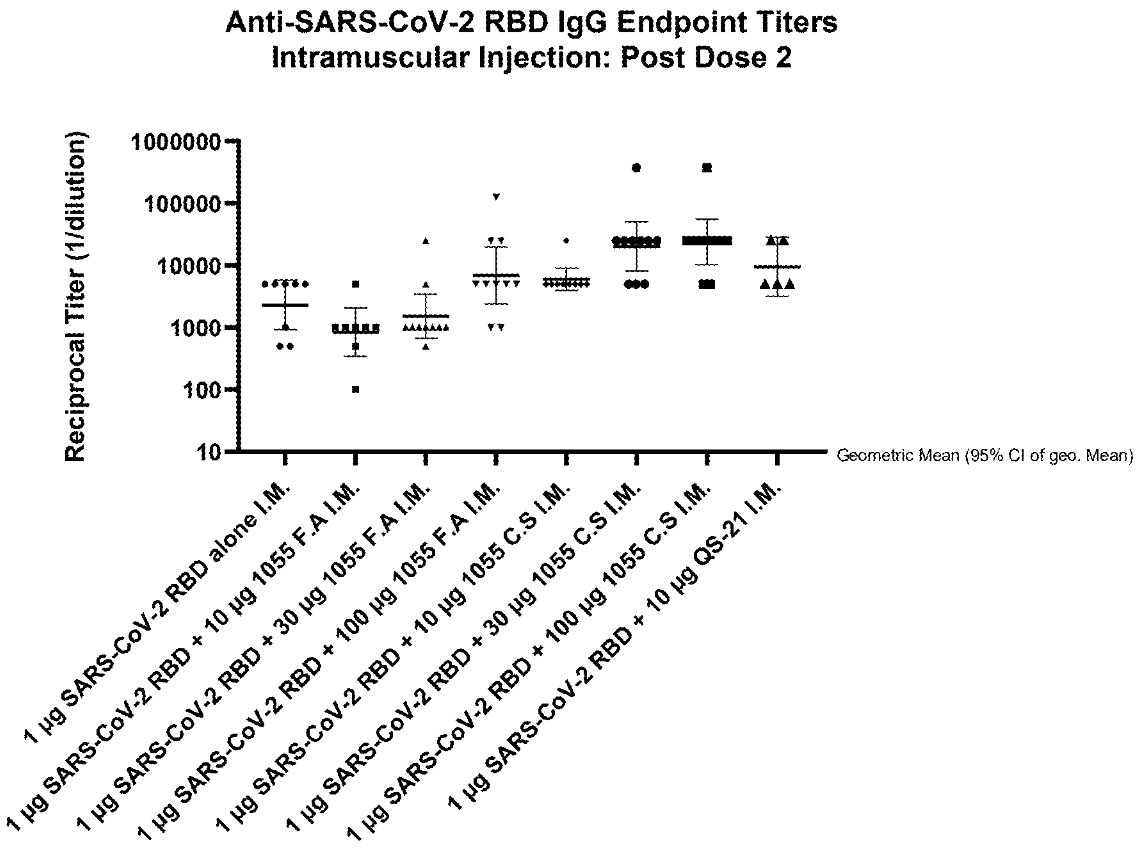
FIG. 17 depicts a chart showing anti-SARS-CoV-2 Receptor Binding Domain (RBD) IgG endpoint titers for groups of mice vaccinated with SARS-CoV-2 antigen and TQL-1055. The data corresponding to this chart are presented in Example 2 of this application.

The IgG endpoint titer data for intramuscular injection post dose 2 is depicted in FIG. 17 and shown in the table below.

TABLE 2-4

| | 1 μg SARS-CoV-2 RBD alone I.M. | 1 μg SARS-CoV-2 RBD + 10 μg 1055 F.A I.M. | 1 μg SARS-CoV-2 RBD + 30 μg 1055 F.A I.M. | 1 μg SARS-CoV-2 RBD + 100 μg 1055 F.A I.M. | 1 μg SARS-CoV-2 RBD + 10 μg 1055 C.S I.M. | 1 μg SARS-CoV-2 RBD + 30 μg 1055 C.S I.M. | 1 μg SARS-CoV-2 RBD + 100 μg 1055 C.S I.M. | 1 μg SARS-CoV-2 RBD + 10 μg QS-21 I.M. |
|---|---|---|---|---|---|---|---|---|
| Number of values | 8 | 8 | 10 | 10 | 9 | 10 | 10 | 5 |
| Geometric mean | 2299 | 840.9 | 1512 | 6899 | 5979 | 20224 | 23755 | 9518 |
| Geometric SD factor | 2.984 | 2.938 | 3.131 | 4.388 | 1.710 | 3.582 | 3.248 | 2.415 |
| Lower 95% CI of geo. mean | 921.9 | 341.5 | 668.4 | 2395 | 3959 | 8117 | 10228 | 3186 |
| Upper 95% CI of geo. mean | 5735 | 2071 | 3421 | 19872 | 9031 | 50385 | 55171 | 28439 |

Discussion:

As shown in the foregoing results and in FIGS. 14 through 17, TQL-1055 exhibits robust adjuvant activity for SARS-CoV-2 antigens. All mice studied were previously naïve to SARS-CoV-2 RBD antigen. The results thus confirm TQL-1055 would be particularly useful as an adjuvant in vaccines against novel pathogens, including human pandemic pathogens.

Example 3—Evaluating Antibody Response of TQL-1055 Choline Salt (C.S.) Adjuvanted H1N1 Influenza a Virus/SARS-CoV-2 Combined Vaccine

Methods

Mice were vaccinated intramuscularly (I.M.) with 0.1 or 1 mcg PR8 HA antigen (Influenza), 0.3 or 3 mcg FL-S (full-length S protein) antigen (SARS-CoV-2), 30 mcg TQL-1055 in situ salt (choline salt), 1 mcg PHAD (in DOPC liposomes), and combinations thereof as shown in Table 3-1 below. Control groups with antigen alone or a combination of antigens were used. Serology was performed at D1, D13, and D28 and samples were analyzed for anti-PR8 HA IgG and anti-SARS-CoV-2 FL-S IgG.

TABLE 3-1

| Grp | Mice | PR8 HA Antigen | FL-S Antigen | TQL-1055 in situ salt | PHAD |
|---|---|---|---|---|---|
| 1 | 10 | 1 mcg PR8 HA | — | — | — |
| 2 | 10 | — | 3 mcg FL-S | — | — |
| 3 | 10 | 1 mcg PR8 HA | 3 mcg FL-S | 30 mcg TQL-1055 | — |
| 4 | 10 | 0.1 mcg PR8 HA | — | 30 mcg TQL-1055 | — |
| 5 | 10 | 1 mcg PR8 HA | — | 30 mcg TQL-1055 | — |
| 6 | 10 | — | 0.3 mcg FL-S | 30 mcg TQL-1055 | — |
| 7 | 10 | — | 3 mcg FL-S | 30 mcg TQL-1055 | — |
| 8 | 10 | 0.1 mcg PR8 HA | 0.3 mcg FL-S | 30 mcg TQL-1055 | — |
| 9 | 10 | 0.1 mcg PR8 HA | 3 mcg FL-S | 30 mcg TQL-1055 | — |
| 10 | 10 | 1 mcg PR8 HA | 0.3 mcg FL-S | 30 mcg TQL-1055 | — |
| 11 | 10 | 1 mcg PR8 HA | 3 mcg FL-S | 30 mcg TQL-1055 | — |
| 12 | 10 | 0.1 mcg PR8 HA | 0.3 mcg FL-S | 30 mcg TQL-1055 | 1 mcg PHAD |
| 13 | 10 | 0.1 mcg PR8 HA | 3 mcg FL-S | 30 mcg TQL-1055 | 1 mcg PHAD |
| 14 | 10 | 1 mcg PR8 HA | 0.3 mcg FL-S | 30 mcg TQL-1055 | 1 mcg PHAD |
| 15 | 10 | 1 mcg PR8 HA | 3 mcg FL-S | 30 mcg TQL-1055 | 1 mcg PHAD |

Results

Figure 18:
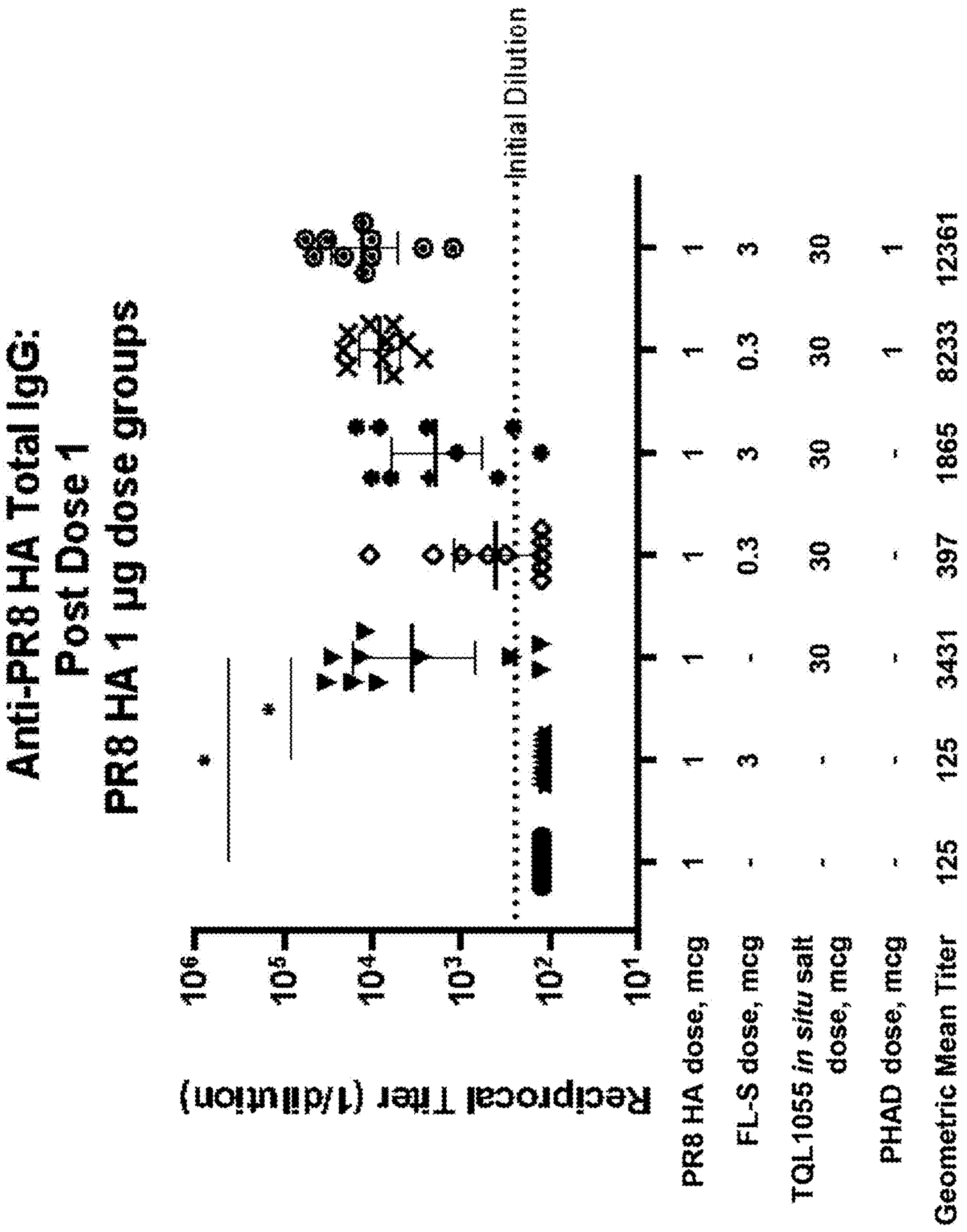
FIG. 18 depicts a chart showing anti-PR8 HA IgG endpoint titers post dose 1 (D13) for PR8 HA 1 mcg dose groups for groups of mice vaccinated with PR8 HA, FL-S, TQL-1055, and/or PHAD as shown in the figure.
Figure 19:
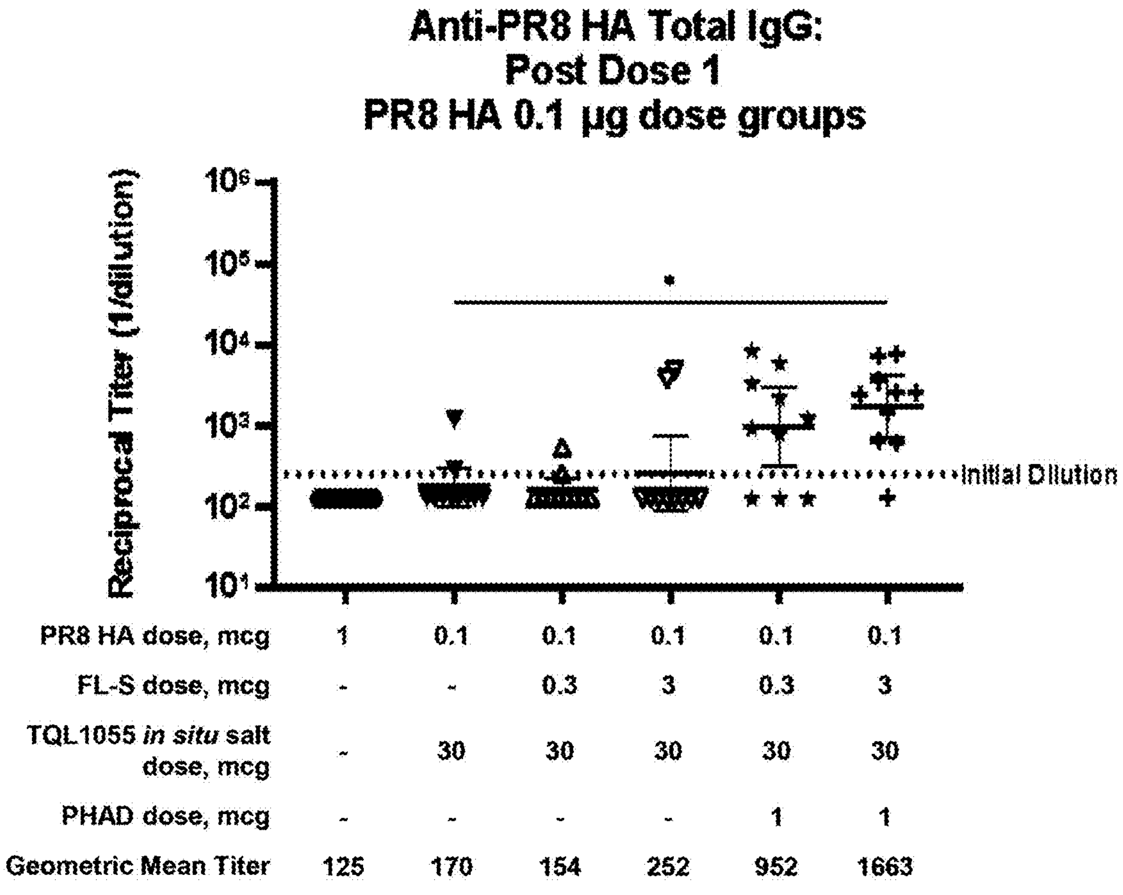
FIG. 19 depicts a chart showing anti-PR8 HA IgG endpoint titers post dose 1 (D13) for PR8 HA 0.1 mcg dose groups for groups of mice vaccinated with PR8 HA, FL-S, TQL-1055, and/or PHAD as shown in the figure.

TQL-1055 allows for vaccination with combined Influenza/SARS-CoV-2 antigens using PR8 HA and FL-S without loss of antigen-specific IgG titers. Specifically:

As shown in FIGS. 18 and 19, adding FL-S to a PR8 HA vaccine with TQL-1055 adjuvant does not significantly decrease PR8-HA specific IgG titers post dose 1.

Figure 20:
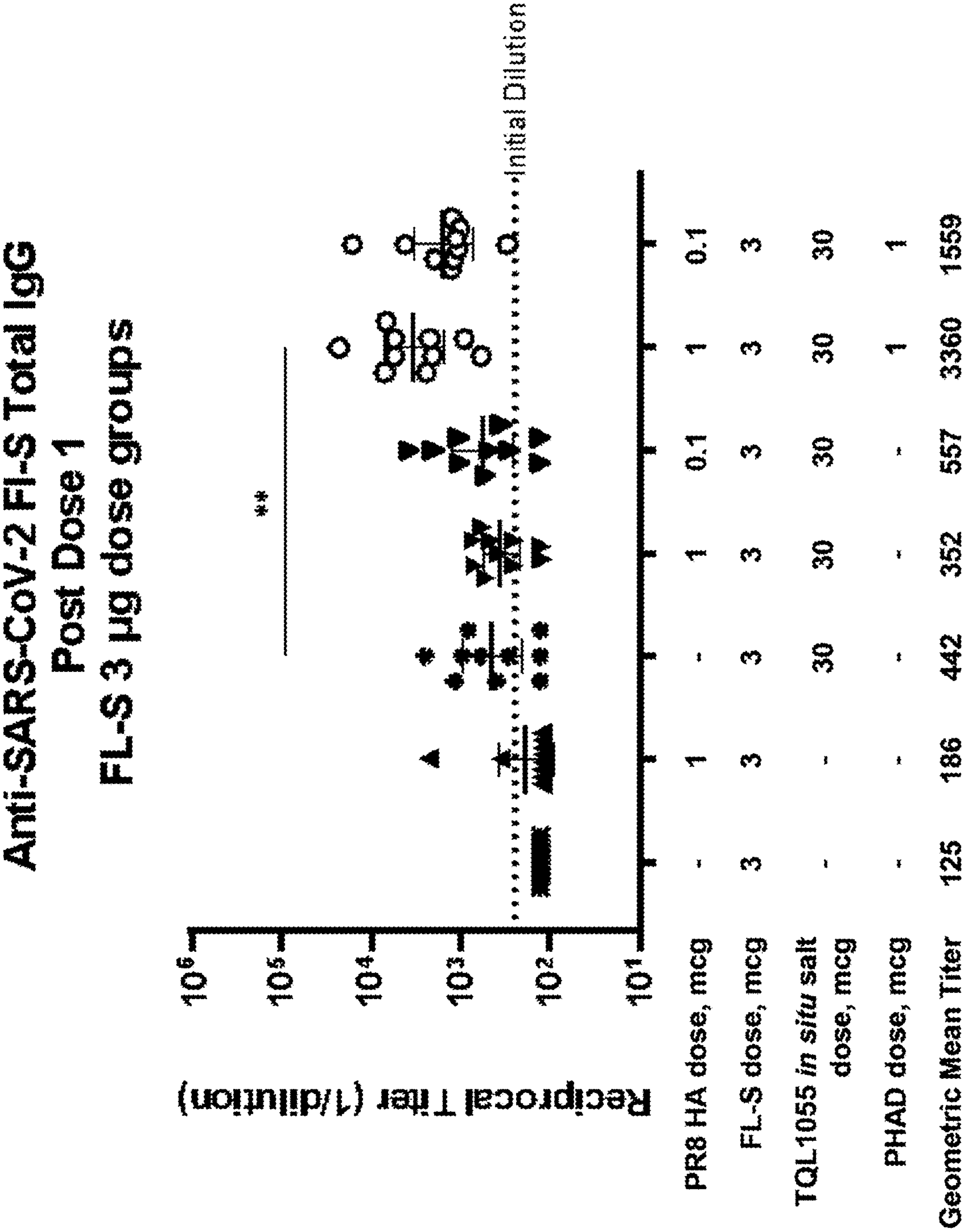
FIG. 20 depicts a chart showing anti-SARS-CoV-2 FL-S endpoint titers post dose 1 (D13) for FL-S 3 mcg dose groups for groups of mice vaccinated with PR8 HA, FL-S, TQL-1055, and/or PHAD as shown in the figure.
Figure 21:
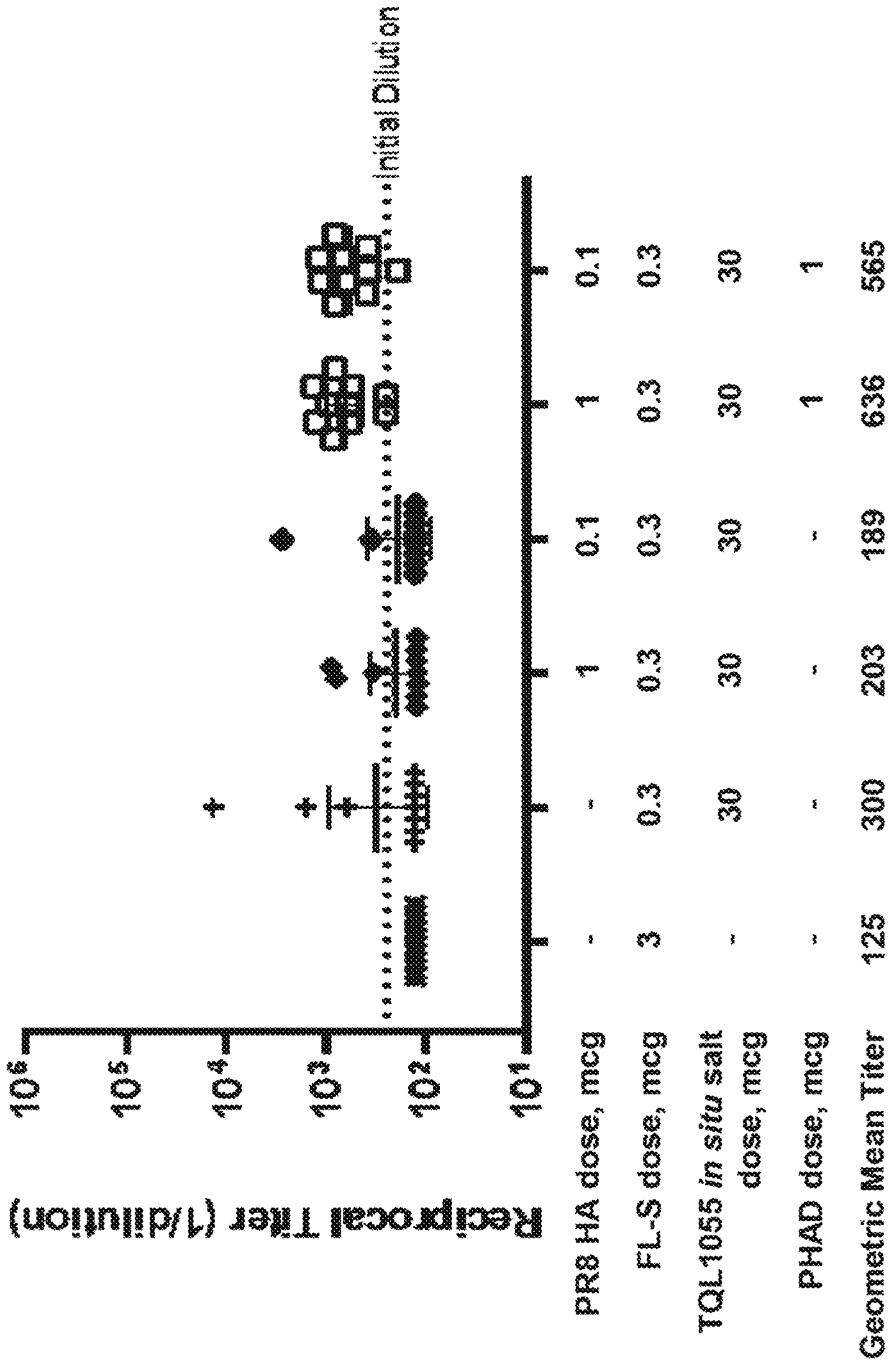
FIG. 21 depicts a chart showing anti-SARS-CoV-2 FL-S endpoint titers post dose 1 (D13) for FL-S 0.3 mcg dose groups for groups of mice vaccinated with PR8 HA, FL-S, TQL-1055, and/or PHAD as shown in the figure.

As shown in FIGS. 20 and 21, adding PR8 HA to a FL-S vaccine with TQL-1055 adjuvant does not significantly decrease FL-S specific IgG titers post dose 1.

Figure 22:
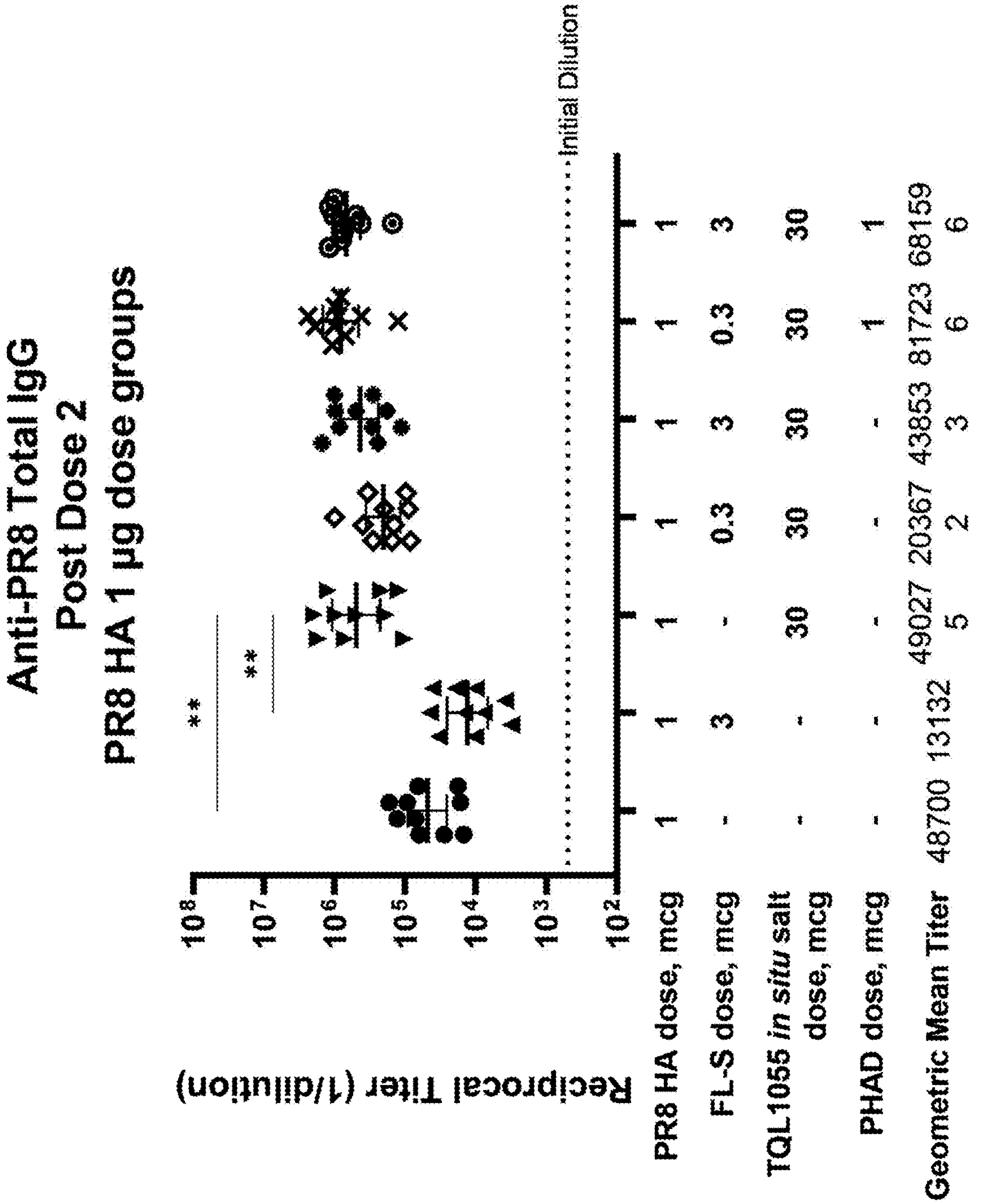
FIG. 22 depicts a chart showing anti-PR8 HA IgG endpoint titers post dose 2 (D28) for PR8 HA 1 mcg dose groups for groups of mice vaccinated with PR8 HA, FL-S, TQL-1055, and/or PHAD as shown in the figure.
Figure 23:
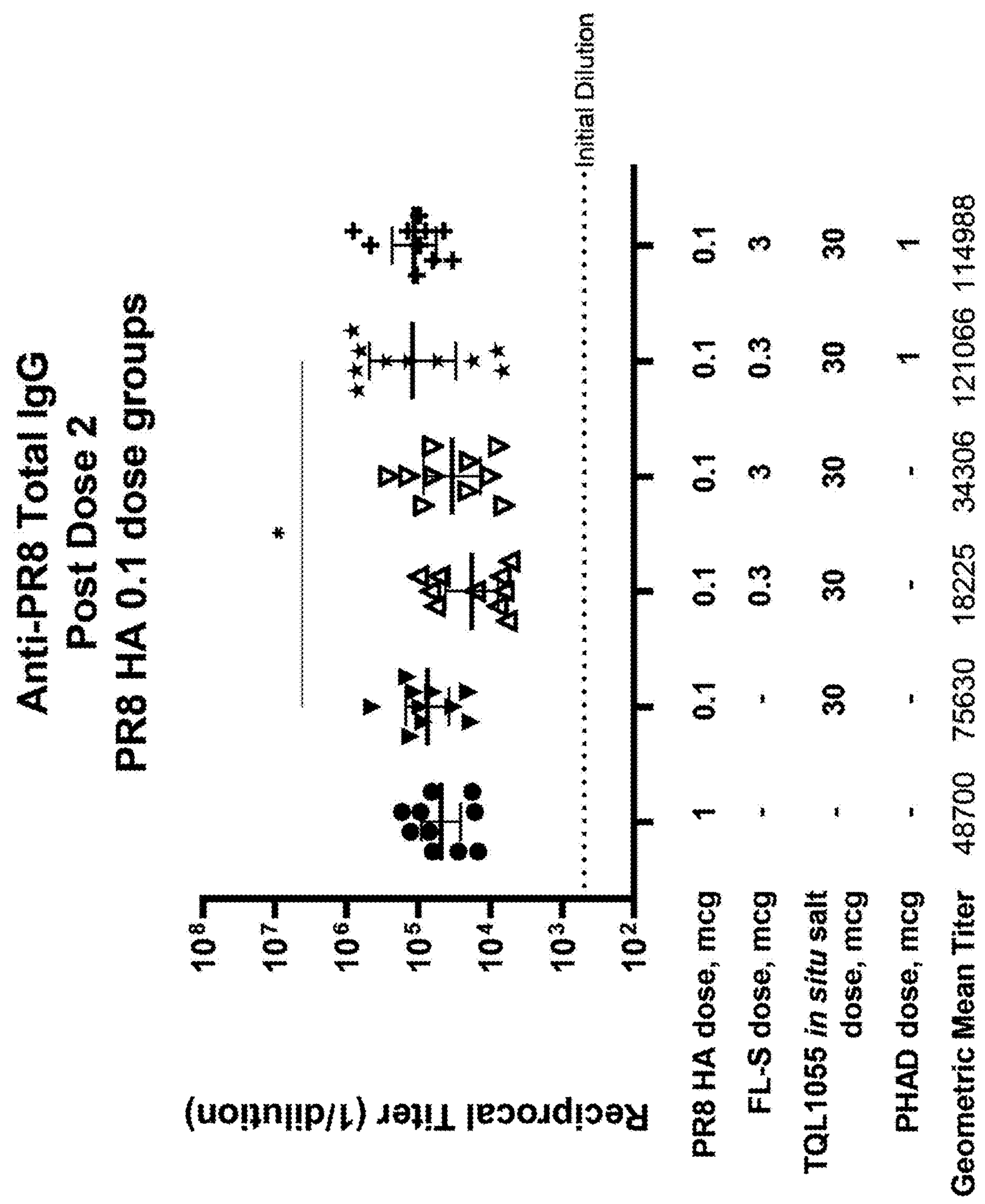
FIG. 23 depicts a chart showing anti-PR8 HA IgG endpoint titers post dose 2 (D28) for PR8 HA 0.1 mcg dose groups for groups of mice vaccinated with PR8 HA, FL-S, TQL-1055, and/or PHAD as shown in the figure.

As shown in FIGS. 22 and 23, adding FL-S to a PR8 HA vaccine with TQL-1055 adjuvant does not significantly decrease PR8-HA specific IgG titers post dose 2.

Figure 24:
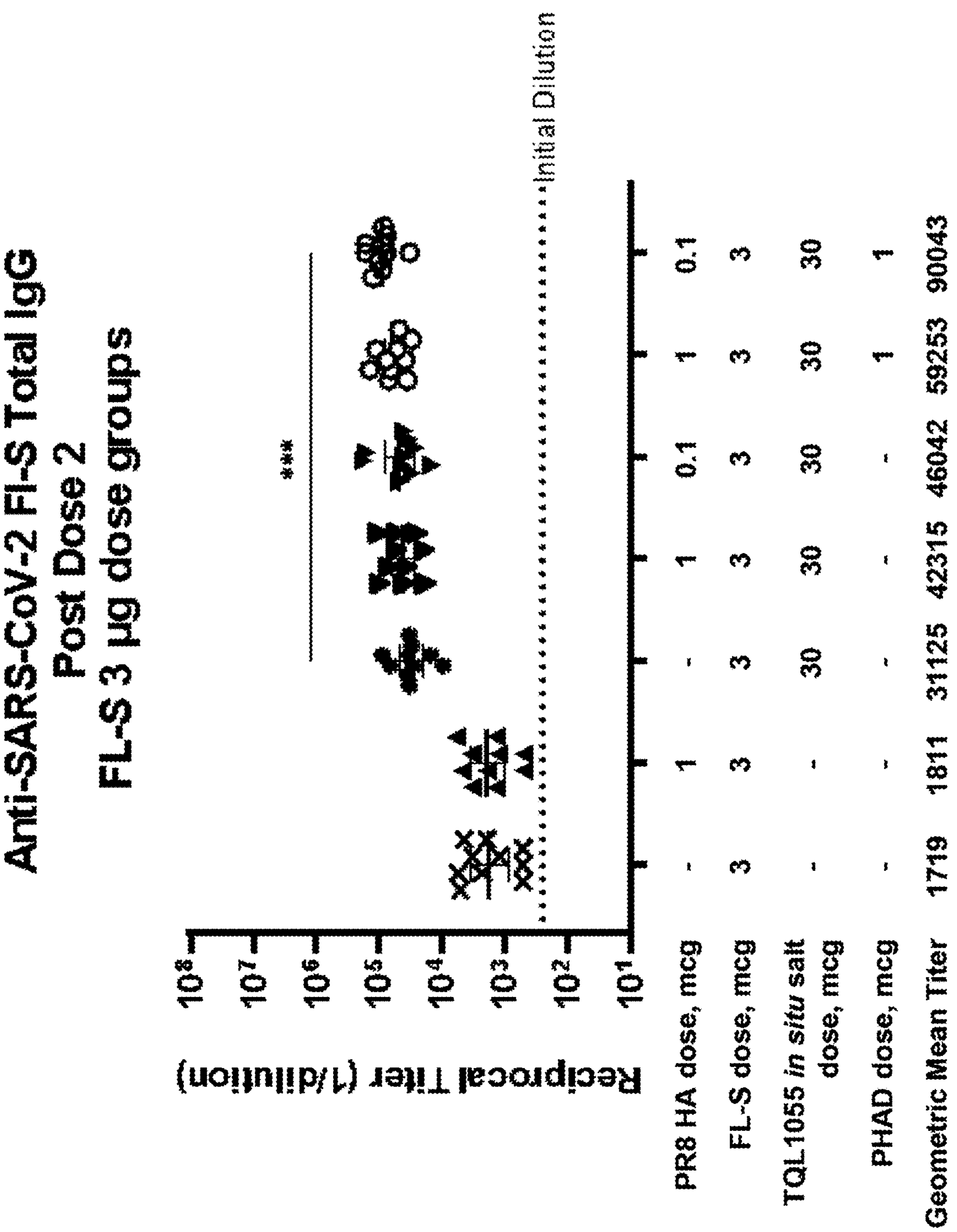
FIG. 24 depicts a chart showing anti-SARS-CoV-2 FL-S endpoint titers post dose 2 (D28) for FL-S 3 mcg dose groups for groups of mice vaccinated with PR8 HA, FL-S, TQL-1055, and/or PHAD as shown in the figure.
Figure 25:
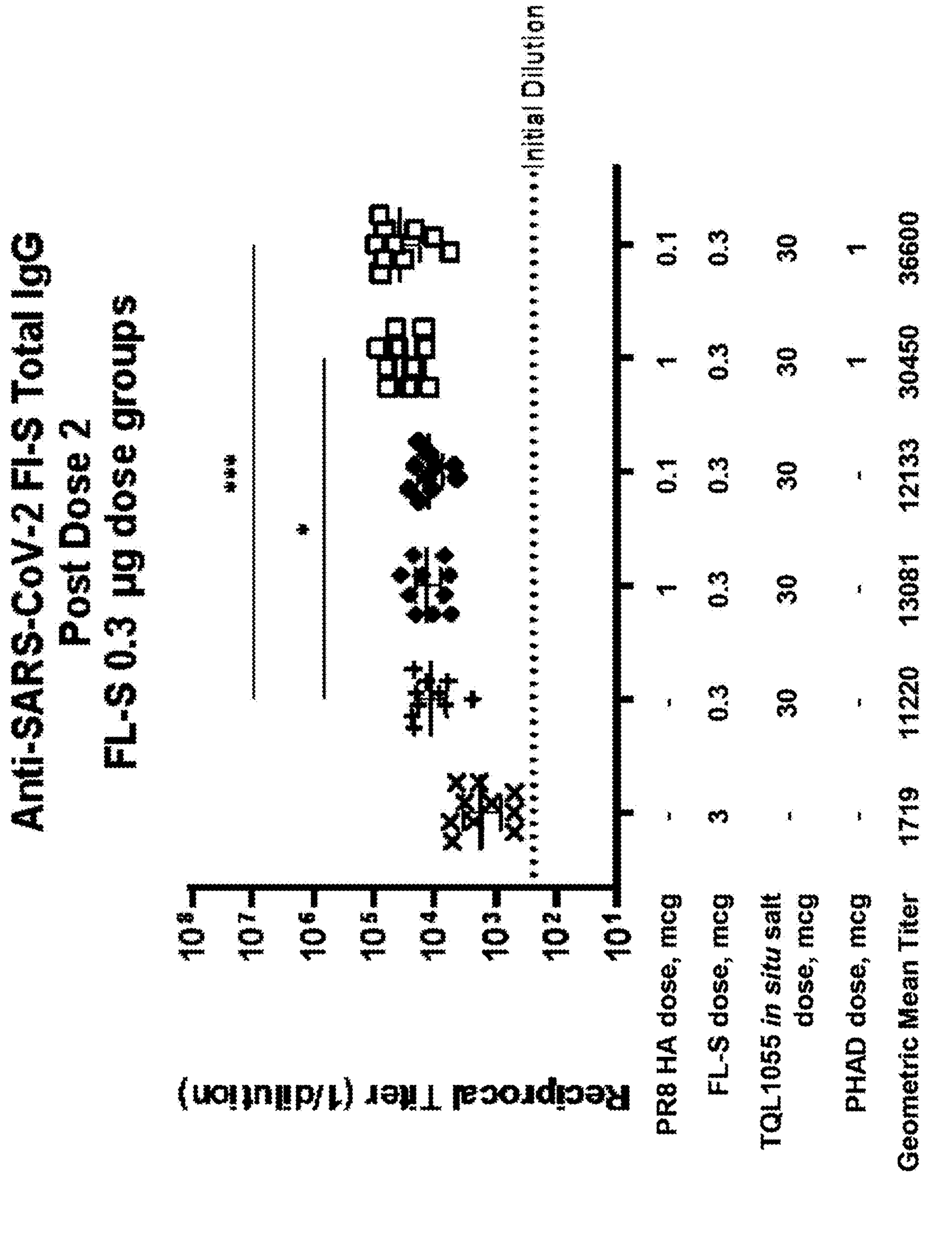
FIG. 25 depicts a chart showing anti-SARS-CoV-2 FL-S endpoint titers post dose 2 (D28) for FL-S 0.3 mcg dose groups for groups of mice vaccinated with PR8 HA, FL-S, TQL-1055, and/or PHAD as shown in the figure.

As shown in FIGS. 24 and 25, adding PR8 HA to a FL-S vaccine with TQL-1055 adjuvant does not significantly decrease FL-S specific IgG titers post dose 2.

Statistical analysis of the post dose 1 (D13) anti-PR8 HA IgG titers demonstrates the following:

TABLE 3-2

| Dunnett's multiple comparisons test | Summary | Adjusted P Value |
|---|---|---|
| 1 µg PR8 + 30 µg TQL1055 in situ salt vs. 1 µg PR8 Alone | * | 0.0324 |
| 1 µg PR8 + 30 µg TQL1055 in situ salt vs. 1 µg PR8 Alone + 3 µg Fl-S Alone | * | 0.0324 |
| 1 µg PR8 + 30 µg TQL1055 in situ salt vs. 1 µg PR8 + 0.3 µg Fl-S + 30 µg TQL1055 in situ salt | ns | 0.0764 |
| 1 µg PR8 + 30 µg TQL1055 in situ salt vs. 1 µg PR8 + 3 µg Fl-S + 30 µg TQL1055 in situ salt | ns | 0.3484 |
| 1 µg PR8 + 30 µg TQL1055 in situ salt vs. 1 µg PR8 + 0.3 µg Fl-S + 30 µg TQL1055 in situ salt + 1 µg PHAD | ns | 0.9996 |
| 1 µg PR8 + 30 µg TQL1055 in situ salt vs. 1 µg PR8 + 3 µg Fl-S + 30 µg TQL1055 in situ salt + 1 µg PHAD | ns | 0.1207 |

TABLE 3-3

| Dunnett's multiple comparisons test | Summary | Adjusted P Value |
|---|---|---|
| 0.1 µg PR8 + 30 µg TQL1055 in situ salt vs. 0.1 µg PR8 + 0.3 µg Fl-S + 30 µg TQL1055 in situ salt | ns | 0.9999 |
| 0.1 µg PR8 + 30 µg TQL1055 in situ salt vs. 0.1 µg PR8 + 3 µg Fl-S + 30 µg TQL1055 in situ salt | ns | 0.8305 |
| 0.1 µg PR8 + 30 µg TQL1055 in situ salt vs. 0.1 µg PR8 + 0.3 µg Fl-S + 30 µg TQL1055 in situ salt + 1 µg PHAD | ns | 0.0601 |
| 0.1 µg PR8 + 30 µg TQL1055 in situ salt vs. 0.1 µg PR8 + 3 µg Fl-S + 30 µg TQL1055 in situ salt + 1 µg PHAD | * | 0.0144 |

Statistical analysis of the post dose 1 (D13) anti-SARS-CoV-2 FL-S IgG titers demonstrates the following:

TABLE 3-4

| Dunnett's multiple comparisons test | Summary | Adjusted P Value |
|---|---|---|
| 3 µg Fl-S + 30 µg TQL1055 in situ salt vs. 3 µg Fl-S Alone | ns | 0.9962 |
| 3 µg Fl-S + 30 µg TQL1055 in situ salt vs. 1 µg PR8 Alone + 3 µg Fl-S Alone | ns | 0.9997 |
| 3 µg Fl-S + 30 µg TQL1055 in situ salt vs. 0.1 µg PR8 + 3 µg Fl-S + 30 µg TQL1055 in situ salt | ns | 0.9997 |
| 3 µg Fl-S + 30 µg TQL1055 in situ salt vs. 1 µg PR8 + 3 µg Fl-S + 30 µg TQL1055 in situ salt | ns | 0.9997 |

TABLE 3-4-continued

| Dunnett's multiple comparisons test | Summary | Adjusted P Value |
|---|---|---|
| 3 μg Fl-S + 30 μg TQL1055 in situ salt vs. 0.1 μg PR8 + 3 μg Fl-S + 30 μg TQL1055 in situ salt + 1 μg PHAD | ns | 0.4043 |
| 3 μg Fl-S + 30 μg TQL1055 in situ salt vs. 1 μg PR8 + 3 μg Fl-S + 30 μg TQL1055 in situ salt + 1 μg PHAD | ** | 0.0049 |

TABLE 3-5

| Dunnett's multiple comparisons test | Summary | Adjusted P Value |
|---|---|---|
| 0.3 μg Fl-S + 30 μg TQL1055 in situ salt vs. 0.1 μg PR8 + 0.3 μg Fl-S + 30 μg TQL1055 in situ salt | ns | 0.4163 |
| 0.3 μg Fl-S + 30 μg TQL1055 in situ salt vs. 1 μg PR8 + 0.3 μg Fl-S + 30 μg TQL1055 in situ salt | ns | 0.3367 |
| 0.3 μg Fl-S + 30 μg TQL1055 in situ salt vs. 0.1 μg PR8 + 0.3 μg Fl-S + 30 μg TQL1055 in situ salt + 1 μg PHAD | ns | 0.6013 |
| 0.3 μg Fl-S + 30 μg TQL1055 in situ salt vs. 1 μg PR8 + 0.3 μg Fl-S + 30 μg TQL1055 in situ salt + 1 μg PHAD | ns | 0.6716 |

Statistical analysis of the post dose 2 (D28) anti-PR8 HA IgG titers demonstrates the following:

TABLE 3-6

| Dunnett's multiple comparisons test | Summary | Adjusted P Value |
|---|---|---|
| 1 μg PR8 + 30 μg TQL1055 in situ salt vs. 1 μg PR8 Alone | ** | 0.0026 |
| 1 μg PR8 + 30 μg TQL1055 in situ salt vs. 1 μg PR8 Alone + 3 μg Fl-S Alone | ** | 0.0012 |
| 1 μg PR8 + 30 μg TQL1055 in situ salt vs. 1 μg PR8 + 0.3 μg Fl-S + 30 μg TQL1055 in situ salt | ns | 0.0571 |
| 1 μg PR8 + 30 μg TQL1055 in situ salt vs. 1 μg PR8 + 3 μg Fl-S + 30 μg TQL1055 in situ salt | ns | 0.8591 |
| 1 μg PR8 + 30 μg TQL1055 in situ salt vs. 1 μg PR8 + 0.3 μg Fl-S + 30 μg TQL1055 in situ salt + 1 μg PHAD | ns | 0.6015 |
| 1 μg PR8 + 30 μg TQL1055 in situ salt vs. 1 μg PR8 + 3 μg Fl-S + 30 μg TQL1055 in situ salt + 1 μg PHAD | ns | >0.9999 |

TABLE 3-7

| Dunnett's multiple comparisons test | Summary | Adjusted P Value |
|---|---|---|
| 0.1 μg PR8 + 30 μg TQL1055 in situ salt vs. 0.1 μg PR8 + 0.3 μg Fl-S + 30 μg TQL1055 in situ salt | ns | 0.7748 |
| 0.1 μg PR8 + 30 μg TQL1055 in situ salt vs. 0.1 μg PR8 + 3 μg Fl-S + 30 μg TQL1055 in situ salt | ns | 0.9551 |
| 0.1 μg PR8 + 30 μg TQL1055 in situ salt vs. 0.1 μg PR8 + 0.3 μg Fl-S + 30 μg TQL1055 in situ salt + 1 μg PHAD | * | 0.0464 |
| 0.1 μg PR8 + 30 μg TQL1055 in situ salt vs. 0.1 μg PR8 + 3 μg Fl-S + 30 μg TQL1055 in situ salt + 1 μg PHAD | ns | 0.7963 |

Statistical analysis of the post dose 2 (028) anti-SARS-CoV-2 FL-S IgG titers demonstrates the following:

TABLE 3-8

| Dunnett's multiple comparisons test | Summary | Adjusted P Value |
|---|---|---|
| 3 μg Fl-S + 30 μg TQL1055 in situ salt vs. 3 μg Fl-S Alone | ns | 0.0996 |
| 3 μg Fl-S + 30 μg TQL1055 in situ salt vs. 1 μg PR8 Alone + 3 μg Fl-S Alone | ns | 0.0995 |
| 3 μg Fl-S + 30 μg TQL1055 in situ salt vs. 0.1 μg PR8 + 3 μg Fl-S + 30 μg TQL1055 in situ salt | ns | 0.345 |
| 3 μg Fl-S + 30 μg TQL1055 in situ salt vs. 1 μg PR8 + 3 μg Fl-S + 30 μg TQL1055 in situ salt | ns | 0.8952 |
| 3 μg Fl-S + 30 μg TQL1055 in situ salt vs. 0.1 μg PR8 + 3 μg Fl-S + 30 μg TQL1055 in situ salt + 1 μg PHAD | *** | 0.0006 |
| 3 μg Fl-S + 30 μg TQL1055 in situ salt vs. 1 μg PR8 + 3 μg Fl-S + 30 μg TQL1055 in situ salt + 1 μg PHAD | ns | 0.2054 |

TABLE 3-9

| Dunnett's multiple comparisons test | Summary | Adjusted P Value |
|---|---|---|
| 0.3 μg Fl-S + 30 μg TQL1055 in situ salt vs. 0.1 μg PR8 + 0.3 μg Fl-S + 30 μg TQL1055 in situ salt | ns | >0.9999 |
| 0.3 μg Fl-S + 30 μg TQL1055 in situ salt vs. 1 μg PR8 + 0.3 μg Fl-S + 30 μg TQL1055 in situ salt | ns | 0.9954 |
| 0.3 μg Fl-S + 30 μg TQL1055 in situ salt vs. 0.1 μg PR8 + 0.3 μg Fl-S + 30 μg TQL1055 in situ salt + 1 μg PHAD | *** | 0.0005 |
| 0.3 μg Fl-S + 30 μg TQL1055 in situ salt vs. 1 μg PR8 + 0.3 μg Fl-S + 30 μg TQL1055 in situ salt + 1 μg PHAD | * | 0.0281 |

Discussion:

As shown in the foregoing results and in FIGS. 18 through 25, TQL-1055 exhibits robust adjuvant activity for Influenza and SARS-CoV-2 antigens. Furthermore, TQL-1055 allows for vaccination with combined Influenza/SARS-CoV-2 antigens using PR8 HA and FL-S without loss of antigen-specific IgG titers.

Example 4—Evaluation of Dose-Sparing Effect for Influenza Vaccine

Vaccination against both seasonal and pandemic influenza requires effective adjuvants to maximize the utility of limited antigen and to enhance immunogenicity in hyporesponsive at-risk populations. First-generation natural saponins are potent immuno-enhancers but are reactogenic and have supply constraints. As part of a NIH-funded project, the novel semisynthetic saponin TQL-1055 was evaluated for its potential to augment the immunogenicity of influenza antigens.

Methods

Groups of 10 $C_{57}$BL/6J mice were immunized subcutaneously (SC) with FLUBLOK® (H3N2 antigen) alone at either a 4.5 mcg or 1.1 mcg dose, or at a 1.1 mcg dose in combination with 10, 30 or 100 mcg TQL-1055 on Days 0 and 21. Sera were analyzed at days 0, 21 and 42 by ELISA for H3N2-specific IgG. Body weights were measured serially.

Results

A 2-dose series of 1.1 mcg FLUBLOK with TQL-1055 elicited anti-H3N2 antibodies in all mice. This effect was TQL-1055 dose-dependent, with GMTs of 2178 in the 10 mcg group, 13674 in the 30 mcg group, and 48959 in the 100 mcg group. The GMT in all TQL-1055 groups were higher than the GMT of 176 in the group receiving 4.5 mcg of FLUBLOK alone. See FIG. 26. Mice receiving TQL-1055 gained weight steadily after immunization, compared with a maximum weight loss of >10% in mice receiving 20 mcg of QS-21. See FIG. 27.

Figure 26:
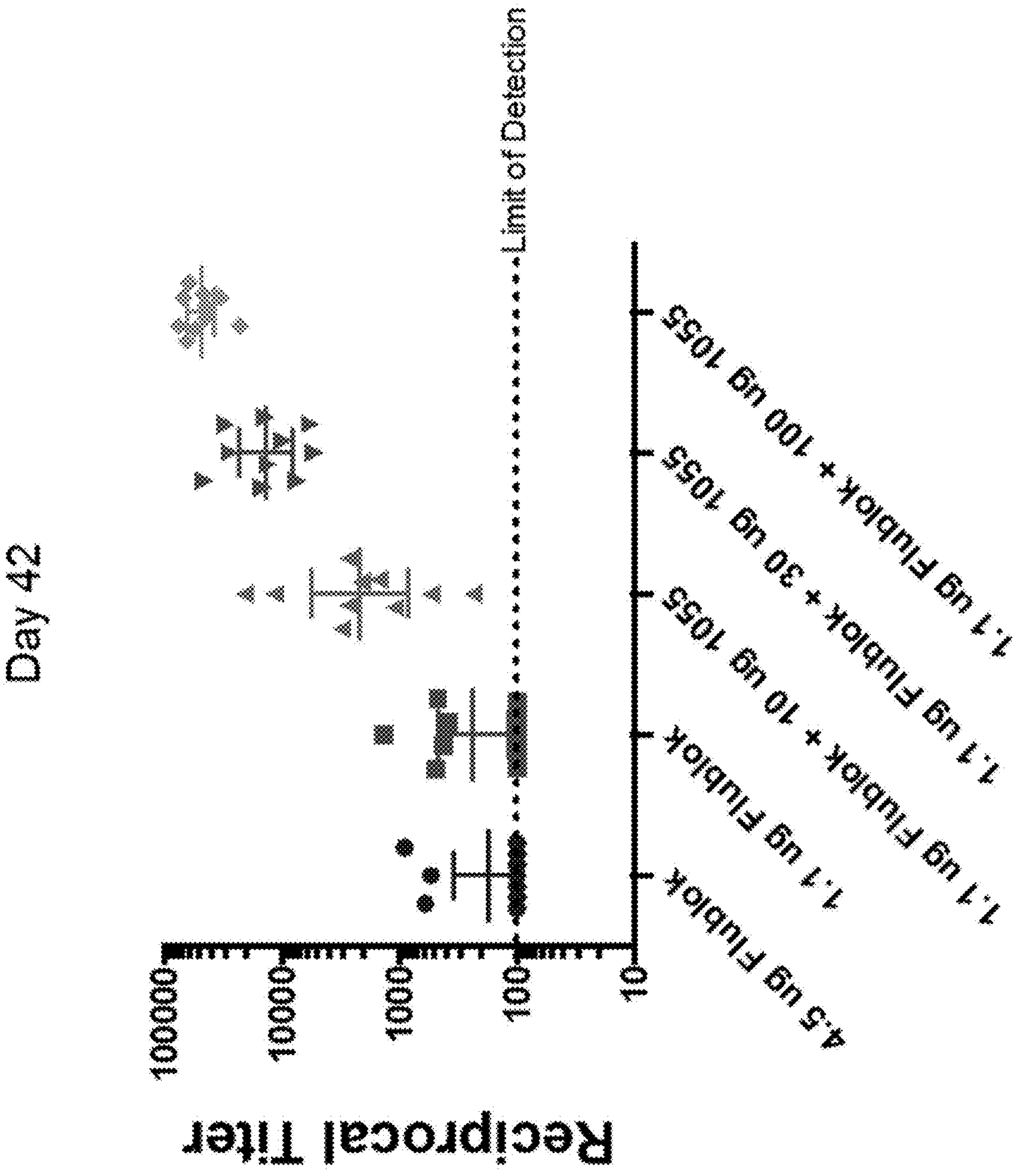
FIG. 26 depicts a graph of murine antibody response to a recombinant antigen influenza vaccine (FLUBLOK®) and demonstrates TQL-1055 exhibits superior antigen dose-sparing effects.
Figure 27:
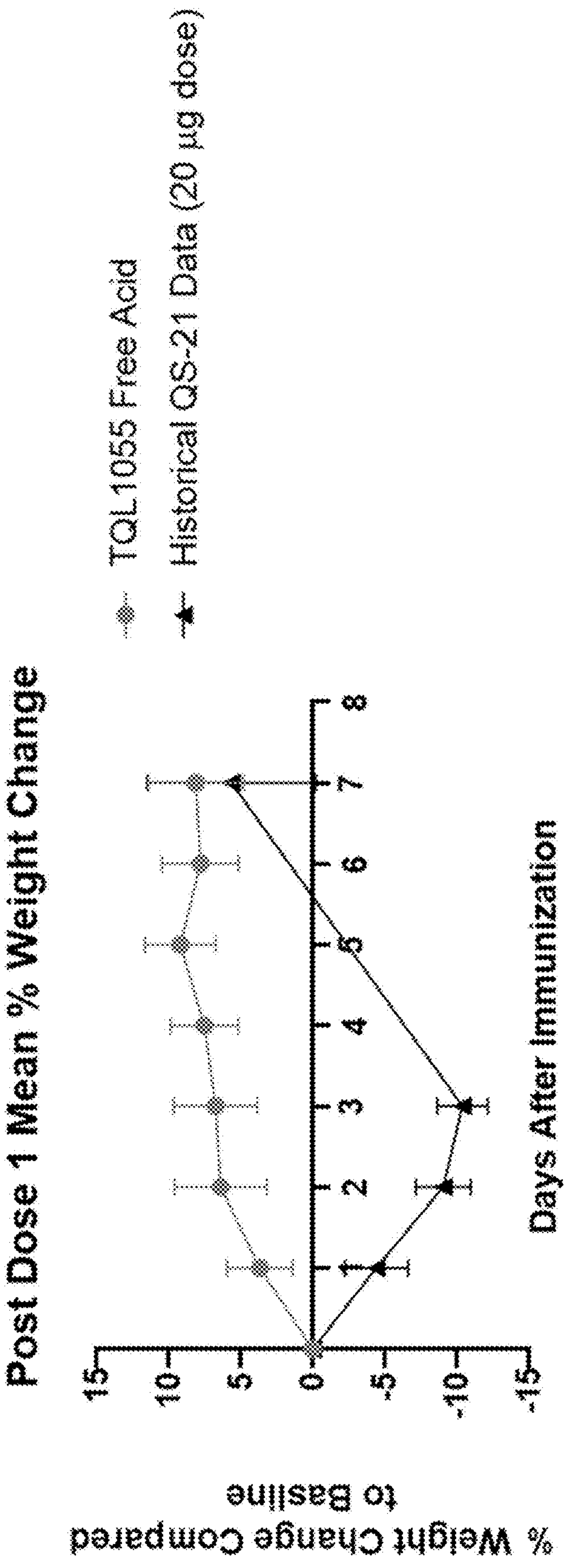
FIG. 27 depicts a graph showing murine tolerability of TQL-1055 free acid compared to QS-21.

Discussion:

As show in FIGS. 26 and 27, TQL-1055 exhibits robust adjuvant activity for influenza antigens, demonstrating an adjuvant dose-sparing effect and improved systemic tolerability compared with QS-21.

The invention claimed is:

1. A pharmaceutical composition for priming or antigen dose-sparing comprising an antigen associated with influenza; and a compound

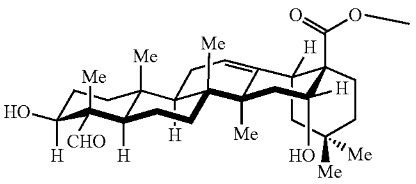

-continued

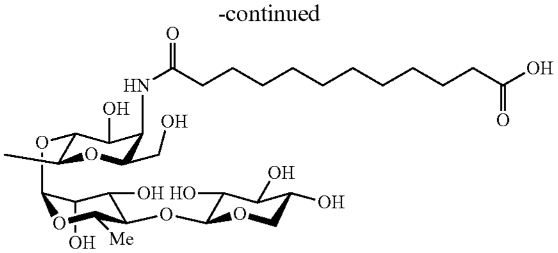

or a pharmaceutically acceptable salt thereof.

2. The pharmaceutical composition of claim 1, wherein the amount of antigen provided is less than the amount of antigen required in the absence of the compound.

3. The pharmaceutical composition of claim 1, wherein the amount of antigen provided is about 10%, 9%, 8%, 7%, 6%, 5%, 4%, or 3% the amount of antigen required in the absence of the compound.

4. The pharmaceutical composition of claim 1, further comprising an antigen associated with SARS-CoV-2 virus.

5. A method of providing a dose sparing effect, comprising providing a pharmaceutical composition according to claim 1.

6. A method of providing a vaccine priming effect, comprising providing a pharmaceutical composition according to claim 1.

7. A method of conferring resistance to an infection, the method comprising administering a pharmaceutical composition according to claim 1.

* * * * *